(12) United States Patent
Bamber et al.

(10) Patent No.: US 7,368,540 B2
(45) Date of Patent: *May 6, 2008

(54) NEMATODE NEUROMUSCULAR JUNCTION GABA RECEPTORS AND METHODS RELATED THERETO

(75) Inventors: Bruce A. Bamber, Salt Lake City, UT (US); Erik M. Jorgensen, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 124 days.

This patent is subject to a terminal disclaimer.

(21) Appl. No.: 11/241,631

(22) Filed: Sep. 30, 2005

(65) Prior Publication Data

US 2006/0020115 A1    Jan. 26, 2006

Related U.S. Application Data

(60) Division of application No. 10/156,240, filed on May 24, 2002, now Pat. No. 7,038,033, which is a continuation of application No. 09/436,063, filed on Nov. 8, 1999, now Pat. No. 6,407,210.

(60) Provisional application No. 60/107,727, filed on Nov. 9, 1998.

(51) Int. Cl.
*C07K 1/00* (2006.01)
*C07K 14/00* (2006.01)
*C07K 17/00* (2006.01)
*C07H 21/04* (2006.01)

(52) U.S. Cl. ..................... 530/350; 536/23.5

(58) Field of Classification Search ................ None
See application file for complete search history.

(56) References Cited

U.S. PATENT DOCUMENTS

| | | | | |
|---|---|---|---|---|
| 5,350,836 | A | 9/1994 | Kopchick et al. | 530/399 |
| 6,407,210 | B1 | 6/2002 | Bamber et al. | 435/7.8 |
| 2003/0065144 | A1 | 4/2003 | Bamber et al. | |

OTHER PUBLICATIONS

Amin, J., and Weiss, D. S., "Homomeric rho 1 GABA channels: activation properties and domains," Receptors and Channels, 2:227-236 (1994).
Bamber BA et al. J. Neroscience 19(13):5348-5359, Jul. 1, 1999.
Barstead, R. J., and Waterston, R. H., "The basal component of the nematode dense-body is vinculin," J. of Biol. Chem., 264(17):10177-10185 (Jun. 15, 1989).
Brenner "Errors in Genome Annotation" Trends in Genetics 15(4):132-133 (1999).
Chang et al. "Stichiometry of a Recombinant GABA Receptor" J. Neurosci. 16(17):5415-5424 (1996).
Davis et al., "Diazepam and Flurazepam: Effects on Conditioned Fear as Measured with the Potentiated Startle Paradigm," Psychopharmacology, 62(1):1-7 (1979).
Davis et al., "Pharmacological and Anatomical analysis of Fear Conditioning Using the Fear Conditioning Using the Fear-Potentiated Startle Paradigm," Behav. Neurosci., 100(6):814 (1986).
Davis, M. "The role of the amygdaia in fear-potentiated startle: implications for animal models of anxiety" *TIPS* 13(1):35-41 (Jan. 1992).
Doerks et al. "Protein Annotation: Detective Work for Function Prediction" Trends in Genetics 14(6):248-250 (1998).
Hafely, W. et al., "Recent Advances in the Molecular Pharmacology of Benzodiazepine Receptors and in the Structure-Activity Relationships of Their Agonists and Antagonists," Advances in Drug Research, Academic Press, 14:165-322 (1985).
Lister et al., "The use of a plus-maze to measure anxiety in the mouse,"Psychopharmacol 92:180-185 (1987).
Mohler, H., "GABAergic Synaptic Transmission," Arzneim.-Forsch./Drug Res., 42(1):211-214 (1992).
Ngo et al. Computational Complexity, Protein Stucture Prediction, and the Levinthal Paradox. The Protein Folding Problem and Tertiary Structure Prediction. Mertz and LeGrand Editors Birkhauser Boston (1994).
Okkema, P. G., and Fire, A., "The *Caenorhabditis elegans* NK-2 class homeoprotein CEH-22 is involved in combinatorial activation of gene expression in pharyngeal muscle," Development 120:2175-2186 (1994).
Puia et al., "Influence of Recombinant γ-Aminobutyric Acid—A Receptor Subunit Composition on the Action of Allosteric Modulators of γ-Aminobutyric Acid-Gated Cl- Currents," Molecular Pharm 39:691-696 (1991).
Skolnick, P. et al., "Nonbenzodiazepin Ligands of the Benzodiazepine Receptor," GABA and Benzodiazepine Receptors, 99-102, Squires, R., Ed. (1987).
Smith and Zhang The Challenges of Genome Sequence Annotation or "The Deveil is in the Details" *Nat Biotechnol.* 15(12):122-3 (1997).
Takada et al., "Thienylpyrazoloquinolines: Potent Agonists and Inverse Agonists to Benzodiazepine Receptors," J. Med. Chem. 31:1738-1745 (1988).
Wilson et al. "2.2 Mb of Contiguous Nucleotide Sequence from Chromosome III of *c. elegans,*" Nature 368:32-38 (1994).

*Primary Examiner*—Robert Landsman
(74) *Attorney, Agent, or Firm*—Needle & Rosenberg, PC

(57) ABSTRACT

The present invention relates to the field of GABA receptor structure and function. In one aspect, the present invention relates to impairment of the gamma-aminobutyric acid (GABA) receptors in parasitic nematodes, for the purpose of crop protection and/or soil treatment. The invention includes mutated nematode GABA receptor subunits, nematode GABA neuromuscular junction receptor complexes, nucleic acids which encode the mutated and functional receptor complexes, antibodies which selectively bind the GABA receptor complexes and/or subunits, and assays for compounds which adversely affect nematode GABA neuromuscular junction receptor function. The present invention therefore relates broadly to recombinant DNA technology, molecular biology tools, and crop protection and/or soil treatment.

9 Claims, 16 Drawing Sheets

```
UNC-49A        ------- -------    ---------- ---------- ---MARPFT LIVLLSAHLC LHVVVTQDED SHINTQL.LS SVLDRLTNRT TYDKRLRPRY   55
UNC-49B        ------- -------    ---------- ---------- ---MARPFT LIVLLSAHLC LHVVVTQDED SHINTQL.LS SVLDRLTNRT TYDKRLRPRY   55
UNC-49C        ------- -------    ---------- ---------- ---MARPFT LIVLLSAHLC LHVVVTQDED SHINTQL.LS SVLDRLTNRT TYDKRLRPRY   55
UNC-49Cshort   ------- -------    ---------- ---------- ---------- ---------- ---------- ---------- ---------- ----------
DM RDL         MSDSKMDKLA RMAPLPRTPL LTIWLAINMA LIAQETGHKR IHTVQAATGG GSMLGDVNIS AILDSFS..V SYDKRVRPNY   78
R BETA2 GABA   ------- -------    ---MWRVRKRG YFGIWSFPLI IAAVCAQSVN DPSNMSL.VK ETVDRLL..K GYDIRLRPDF   31
                                                                                    ▽                                    ▲
                                                 *        *                *
UNC-49A        GEKPVDVGIT IHVSSISAVS EVDMDFTLDF YMRQTWQDPR LAFGSLDLGL SKEIDSLTVG VDYLDRLWKP DTFFPNEKKS   135
UNC-49B        GEKPVDVGIT IHVSSISAVS EVDMDFTLDF YMRQTWQDPR LAFGSLDLGL SKEIDSLTVG VDYLDRLWKP DTFFPNEKKS   135
UNC-49C        GEKPVDVGIT IHVSSISAVS EVDMDFTLDF YMRQTWQDPR LAFGSLDLGL SKEIDSLTVG VDYLDRLWKP DTFFPNEKKS   135
UNC-49Cshort   ---------- ---------- ---------- ---------- ---------- ---------- ---------- ----------
DM RDL         GGPPVEVGVT MYVLSISSVS EVLMDFILDF YFRQFMTDPR LAYRKR.... .PGVETLSVG SEFIKNIWKP DTFFVNEKQS   153
R BETA2 GABA   GGPPVAVGMN IDIASIDMVS EVNMDYILTM YFQQAWRDKR LSYNVI.... .P..LNLTLD NRVADQLWKP DTYFLNDKKS   111
                                                 *    *                                 #

UNC-49A        FFHLATTHNS FLRIEGDGTV YTSQRLIVTA TCPMDLKLFP MDSQHCKLEI ESYGYSILDI MYVSHEKK.. .....SVSTE   208
UNC-49B        FFHLATTHNS FLRIEGDGTV YTSQRLIVTA TCPMDLKLFP MDSQHCKLEI ESYGYETKDI DYWGKKRTD LEITAVKED   214
UNC-49C        FFHLATTHNS FLRIEGDGTV YTSQRLIVTA TCPMDLKLFP MDSQHCKLEI ESYAYSTAEI EYKWCTSKEP NCSTAVKADA   215
UNC-49Cshort   ---------- ---------- ---------- ---------- -------M ESYGYSTAEI EYKWCTSKEP NCSTAVKADA   31
DM RDL         YFHIATSNE FIRVHHSGSI TRSIRLIITA SCPMNLQYFP MDRQLCHIEI ESFGYTMRDI RYFW...... R DGLSSVGMSS   228
R BETA2 GABA   FVHGVIVKNR MIRLHPDGTV LYGLRITTTA ACMMDLRRYP LDEQNCTLEI ESYGYTTDDI EFYW...... R GDDNAVTGVT   179
                                                            ├─────────BDI─────────┤
```

FIG. 4B-1

```
UNC-49A      SYELPQFVLQ SIKVVNHTQK LSSGEYSRLC WFFLFKRNIG FYIIQIYLPS VLIVIVISWVS FWLSRDATPA RVALGVTITVL   288
UNC-49B      TFQLPQFQPT LYFVNTTKAE TSSGKYVRLA LEVILVRNMG FYTMNIVIPS ILIVTISWVS FWLNREASPA RVGLGVUTVL   294
UNC-49C      NIELSSYKFT KICQKRTLAS TSSGTYSRLR VSFIFDRDSG FYFLQIFFPA SLVVVLSWIS FWINRDSAPS RTLIGTMIVL   295
UNC-49Cshort NIELSSYKFT KICQKRTLAS TSSGTYSRLR VSFIFDRDSG FYFLQIFFPA SLVVVLSWIS FWINRDSAPS RTLIGTMIVL   111
DM RDL       EVELPQFRVL GHRQRATEIN LTTGNYSRLA CEIQFVRSMG YYLIQIYIPS GLIVISWVS FWLNRNATPA RVALGVTITVL  308
R BETA2 GABA KIELPQFSIV DYKLITKKVV FSTGSYPRLS LSFKLKRNIG YFILQIYMPS ILITILSWVS FWINYDASAA RVALGIITVL  259
                                                                          ——————— M1 ——————————— ——M2— non-conserved
                                                                                        residues
                                                                                     corresponding to
                                                                                     intracellular loop
                                                                                        not shown
                    @        —BDII—
UNC-49A      TMTLMTMTN SSMPKVSYVK SIDIFLGVCF MMVFCSLLEY AAVGYISKRM KLVRARKESR MLTPLPHLES
UNC-49B      TMTLITTTN NSMPKVSYVK GLDVFLNFCF VMVFASLLEY AIVSYMNKRL VL...RREKR RKAAEQQQRN
UNC-49C      TETHLMTGTN RRLPPVAYVK AVDVFLGFCY LLVILALIEY ACVAYSKKKN EDRRRREKKT EHKPAPPTPD
UNC-49Cshort TETHLMTGTN RRLPPVAYVK AVDVFLGFCY LLVILALIEY ACVAYSKKKN EDRRRREKKT EHKPAPPTPD
DM RDL       TMTLMSSTN AALPKISYVK SIDVYLGTCF VMVFASLLEY ATVGYMAKRI QMRKQRFMAI QKIAEQKKQQ
R BETA2 GABA TMTUINTHLR ETLPKIPYVK AIDMYLMGCF VFVFMALLEY ALVNYIFFGR GPQRQKKAAE KAANANNEKM
                                             ————— M3 —————

UNC-49A      RPSNIDKYSR SLFPSIFVLF NVGYWAYFIR QSQIQEEQRN SQIL——————————————————————  487
UNC-49B      TPAKIDKLSR YGFPLSFSIF NIVYWLY....  .MKYLSL NSSDKIQEND KWQQIH————————      487
UNC-49C      SHSHIDIVSR AAFPLVFILF NTLFWLILLY KSKRLPYISE HEGDRCDAPD LH——————————       448
UNC-49Cshort SHSHIDIVSR AAFPLVFILF NTLFWLILLY KSKRLPYISE HEGDRCDAPD LH——————————       426
DM RDL       TPSDIDKYSR IVFPVCFVCF NLMYWIIYLH VSDVVADDLV LLGEE——————————————————      606
R BETA2 GABA DVNAIDRWSR IFFPVVFSFF IFFPVVFSFF NIVYWLYYVN ——————————————————————      487
                  — M4 ——
```

FIG. 4B-2

|          | M3 | | | | A | | C |
|---|---|---|---|---|---|---|---|

```
            M3                               A              C
          ─────                              *              *
UNC-49A   LLEYAAVGYISKRMKLVRARKESRMLTPLPHLESLPPKRTLSVPSYFNN............TTYRPFYSSTDQTS

UNC-49B.1 LLEYAIVSYMNKRLVLRREKRRKAAEQQQRNEMPMFNASPKAANNN...............ADLYFA
UNC-49B.1 LLEYAIVSYMNKRLVLRREKRRKAAEQQQRNEMPMFNASPKAANNN...............ADLYFA
UNC-49B.1 LLEYAIVSYMNKRLVLRREKRRKAAEQQQRNEMPMFNASPKAANNNSYEMTLMSQNSTPAKSYVQADLYFA

UNC-49C   LIEYACVAYSKKKNEDRRRREKKTEHKPAPPTPDILHDVRLAECTCNA.....................

M4
                  *              C              *           ─────
UNC-49A   NLYIPESQRTTIFSNEDAVPNELTPMLGRSNSQASVFLYQTAVISDDEFGRFWRWLRPSNIDKYSRSLFP

UNC-49B.1 GHNSSMNPLMEIPENCDCRTIPMMQHPRLVTDGAHTLWPAPFARPKKASKTCCQRWTPAKIDKLSRYGFP
UNC-49B.1 ......NPLMEIPENCDCRTIPMMQHPRLVTDGAHTLWPAPFARPKKASKTCCQRWTPAKIDKLSRYGFP
UNC-49B.1 GHNSSMNPLMEIPENCDCRTIPMMQHPRLVTDGAHTLWPAPFARPKKASKTCCQRWTPAKIDKLSRYGFP
                                        A
                                        *
UNC-49C   ....................................APTSIIAVIKQSNRFCVSHSHIDIVSRAAFP
```

FIG. 4C

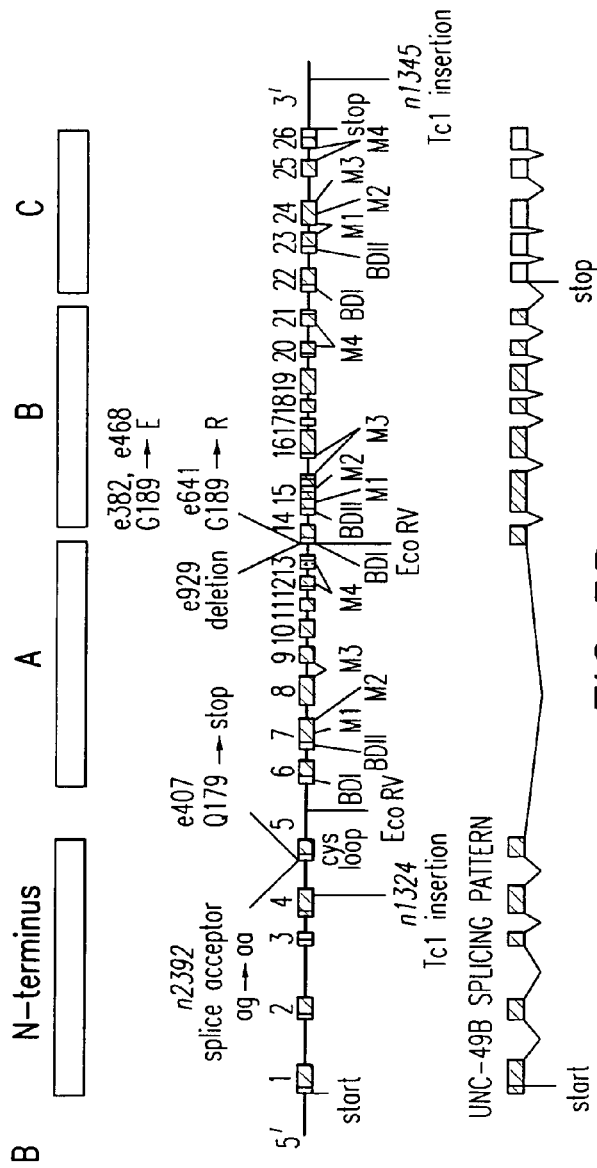

|  | GFP CONSTRUCTS | | | | | SUBUNITS | | | |
|---|---|---|---|---|---|---|---|---|---|
|  | 4kb5' | N | A | B | C | A | B | C | Cshort |
| UNC-49A::GFP |  |  | c-c  GFP |  |  | GFP | + | + | + |
| UNC-49B::GFP |  |  | c-c | GFP |  | + | GFP | + | + |
| UNC-49C::GFP |  |  | c-c |  | GFP | + | + | GFP | GFP |
| UNC-49short::GFP |  |  | c-c STOP |  | GFP | − | − | − | GFP |

FIG. 6A

UNC-49B::GFP

UNC-49C::GFP

UNC-49B::GFPΔC

UNC-49C::GFPΔB

SEQUENCE LISTING

<160> NUMBER OF SEQ ID NOS: 18

<210> SEQ ID NO 1
<211> LENGTH: 1652
<212> TYPE: PRT
<213> ORGANISM: Caenorhabditis elegans

<400> SEQUENCE: 1

```
Cys Gly Gly Ala Ala Ala Ala Ala Cys Cys Thr Cys Cys Cys Ala
  1               5                  10                  15

Ala Cys Ala Thr Thr Gly Gly Cys Thr Cys Ala Cys Ala Cys Cys Cys
                 20                  25                  30

Gly Gly Ala Thr Thr Ala Thr Gly Ala Thr Cys Thr Thr Cys Thr Gly
             35                  40                  45

Cys Thr Gly Cys Thr Cys Cys Thr Gly Cys Thr Gly Cys Thr Cys Cys
         50                  55                  60

Thr Thr Cys Thr Gly Cys Thr Gly Thr Ala Gly Thr Thr Gly Ala Gly
 65                  70                  75                  80

Ala Cys Gly Ala Ala Gly Ala Ala Gly Ala Ala Gly Ala Ala Gly Ala
                 85                  90                  95

Ala Gly Cys Thr Cys Cys Ala Thr Thr Cys Thr Cys Gly Ala Gly Ala
            100                 105                 110

Ala Ala Thr Gly Gly Cys Thr Cys Gly Thr Cys Cys Ala Thr Thr Cys
            115                 120                 125

Ala Cys Ala Cys Thr Thr Ala Thr Cys Gly Thr Ala Cys Thr Cys Cys
            130                 135                 140

Thr Cys Thr Cys Cys Gly Cys Ala Cys Ala Thr Cys Thr Gly Thr Gly
```

-continued

```
145                 150                 155                 160

Thr Cys Thr Ala Cys Ala Thr Gly Thr Gly Gly Thr Thr Gly Thr Gly
                165                 170                 175
Ala Cys Ala Cys Ala Gly Gly Ala Thr Gly Ala Gly Gly Ala Cys Thr
            180                 185                 190

Cys Ala Cys Ala Thr Ala Thr Cys Ala Ala Cys Ala Cys Thr Cys Ala
        195                 200                 205

Ala Cys Thr Cys Cys Thr Cys Thr Cys Ala Thr Cys Ala Gly Thr Thr
    210                 215                 220
Cys Thr Cys Gly Ala Thr Ala Gly Ala Cys Thr Cys Ala Cys Gly Ala
225                 230                 235                 240
Ala Thr Cys Gly Cys Ala Cys Thr Ala Cys Thr Thr Ala Thr Gly Ala
                245                 250                 255
Thr Ala Ala Ala Ala Gly Ala Thr Thr Ala Cys Gly Gly Cys Cys Cys
            260                 265                 270

Ala Gly Gly Thr Ala Thr Gly Gly Thr Gly Ala Ala Ala Ala Gly Cys
        275                 280                 285

Cys Ala Gly Thr Cys Gly Ala Cys Gly Thr Thr Gly Gly Ala Ala Thr
    290                 295                 300

Thr Ala Cys Gly Ala Thr Ala Cys Ala Cys Gly Thr Thr Thr Cys Thr
305                 310                 315                 320
Thr Cys Ala Ala Thr Cys Thr Cys Thr Gly Cys Ala Gly Thr Thr Thr
                325                 330                 335
Cys Ala Gly Ala Ala Gly Thr Thr Gly Ala Thr Ala Thr Gly Gly Ala
            340                 345                 350
Cys Thr Thr Cys Ala Cys Ala Thr Thr Ala Gly Ala Cys Thr Thr Cys
        355                 360                 365

Thr Ala Cys Ala Thr Gly Cys Gly Thr Cys Ala Ala Ala Cys Gly Thr
    370                 375                 380

Gly Gly Cys Ala Ala Gly Ala Cys Cys Cys Thr Cys Gly Ala Cys Thr
385                 390                 395                 400

Ala Gly Cys Cys Thr Thr Cys Gly Gly Ala Ala Gly Thr Cys Thr Thr
                405                 410                 415

Gly Ala Thr Thr Thr Gly Gly Gly Ala Cys Thr Thr Thr Cys Cys Ala
            420                 425                 430

Ala Ala Gly Ala Ala Ala Thr Cys Gly Ala Cys Thr Cys Ala Cys Thr
        435                 440                 445

Thr Ala Cys Cys Gly Thr Cys Gly Gly Ala Gly Thr Ala Gly Ala Cys
    450                 455                 460

Thr Ala Cys Cys Thr Gly Gly Ala Thr Ala Gly Ala Cys Thr Gly Thr
465                 470                 475                 480

Gly Gly Ala Ala Ala Cys Cys Cys Gly Ala Cys Ala Cys Gly Thr Thr
                485                 490                 495

Cys Thr Thr Cys Cys Cys Ala Ala Ala Thr Gly Ala Ala Ala Ala Gly
            500                 505                 510

Ala Ala Ala Thr Cys Ala Thr Thr Cys Thr Thr Cys Cys Ala Cys Thr
        515                 520                 525

Thr Gly Gly Cys Ala Ala Cys Cys Ala Cys Ala Cys Ala Thr Ala Ala
    530                 535                 540

Cys Thr Cys Gly Thr Thr Cys Cys Thr Thr Cys Gly Thr Ala Thr Cys
545                 550                 555                 560

Gly Ala Gly Gly Gly Thr Gly Ala Thr Gly Gly Ala Ala Cys Gly Gly
                565                 570                 575
```

-continued

Thr Thr Thr Ala Thr Ala Cys Thr Ala Gly Thr Cys Ala Ala Ala Gly
580 585 590

Ala Thr Thr Ala Ala Cys Ala Gly Thr Cys Ala Cys Thr Gly Cys Ala
595 600 605

Ala Cys Gly Thr Gly Thr Cys Cys Ala Ala Thr Gly Gly Ala Cys Cys
610 615 620

Thr Gly Ala Ala Gly Cys Thr Gly Thr Thr Cys Cys Cys Ala Ala Thr
625 630 635 640

Gly Gly Ala Cys Thr Cys Thr Cys Ala Ala Cys Ala Cys Thr Gly Thr
645 650 655

Ala Ala Ala Cys Thr Gly Gly Ala Ala Ala Thr Thr Gly Ala Ala Ala
660 665 670

Gly Cys Thr Ala Thr Gly Cys Gly Thr Ala Thr Thr Cys Gly Ala Cys
675 680 685

Gly Gly Cys Cys Gly Ala Ala Ala Thr Cys Gly Ala Gly Thr Ala Cys
690 695 700

Ala Ala Ala Thr Gly Gly Thr Gly Thr Ala Cys Gly Thr Cys Gly Ala
705 710 715 720

Ala Gly Gly Ala Gly Cys Cys Gly Ala Ala Thr Thr Gly Thr Thr Cys
725 730 735

Gly Ala Cys Ala Gly Cys Gly Gly Thr Cys Ala Ala Gly Gly Cys Cys
740 745 750

Gly Ala Cys Gly Cys Gly Ala Ala Cys Ala Thr Cys Gly Ala Ala Cys
755 760 765

Thr Gly Thr Cys Gly Ala Gly Thr Thr Ala Thr Ala Ala Ala Thr Thr
770 775 780

Cys Ala Cys Thr Ala Ala Ala Ala Thr Cys Thr Gly Cys Cys Ala Ala
785 790 795 800

Ala Ala Ala Cys Gly Gly Ala Cys Ala Cys Thr Thr Gly Cys Cys Ala
805 810 815

Gly Cys Ala Cys Thr Thr Cys Ala Thr Cys Gly Gly Gly Gly Ala Cys
820 825 830

Cys Thr Ala Cys Thr Cys Thr Cys Gly Thr Cys Thr Ala Cys Gly Gly
835 840 845

Gly Thr Thr Ala Gly Thr Thr Thr Cys Ala Thr Ala Thr Thr Thr Gly
850 855 860

Ala Thr Cys Gly Cys Gly Ala Cys Ala Gly Cys Gly Gly Cys Thr Thr
865 870 875 880

Cys Thr Ala Cys Thr Thr Thr Cys Thr Thr Cys Ala Ala Ala Thr Ala
885 890 895

Thr Thr Thr Thr Thr Cys Cys Cys Thr Gly Cys Cys Ala Gly Cys Cys
900 905 910

Thr Cys Gly Thr Cys Gly Thr Ala Gly Thr Thr Thr Thr Ala Thr Cys
915 920 925

Ala Thr Gly Gly Ala Thr Cys Thr Cys Ala Thr Thr Cys Thr Gly Gly
930 935 940

Ala Thr Cys Ala Ala Thr Cys Gly Thr Gly Ala Cys Thr Cys Gly Gly
945 950 955 960

Cys Gly Cys Cys Thr Thr Cys Gly Cys Gly Ala Ala Cys Cys Cys Thr
965 970 975

Ala Ala Thr Cys Gly Gly Thr Ala Cys Gly Ala Thr Gly Ala Cys Gly
980 985 990

-continued

```
Gly Thr Gly Cys Thr Cys Ala Thr Gly Ala Gly Ala Cys Thr Cys
        995                 1000                1005
Ala Thr Cys Thr Thr Ala Thr Gly Ala Cys Cys Gly Gly Ala Ala Cys
       1010                 1015                1020
Cys Ala Ala Thr Cys Gly Ala Cys Gly Thr Cys Thr Thr Cys Cys Ala
1025                 1030                1035                1040
Cys Cys Ala Gly Thr Thr Gly Cys Cys Thr Ala Thr Gly Thr Ala Ala
                1045                1050                1055
Ala Ala Gly Cys Cys Gly Thr Thr Gly Ala Thr Gly Thr Ala Thr Thr
        1060                1065                1070
Cys Cys Thr Cys Gly Gly Thr Thr Thr Cys Thr Gly Cys Thr Ala Thr
        1075                1080                1085
Cys Thr Thr Cys Thr Gly Gly Thr Thr Ala Thr Ala Cys Thr Gly Gly
       1090                 1095                1100
Cys Gly Thr Thr Gly Ala Thr Cys Gly Ala Gly Thr Ala Cys Gly Cys
1105                 1110                1115                1120
Cys Thr Gly Thr Gly Thr Thr Gly Cys Cys Thr Ala Cys Thr Cys Ala
                1125                1130                1135
Ala Ala Ala Ala Ala Gly Ala Ala Gly Ala Ala Cys Gly Ala Gly Gly
        1140                1145                1150
Ala Thr Cys Gly Thr Cys Gly Gly Ala Gly Ala Ala Gly Ala Gly Ala
        1155                1160                1165
Gly Ala Ala Gly Ala Ala Gly Ala Cys Gly Gly Ala Gly Cys Ala Thr
        1170                1175                1180
Ala Ala Ala Cys Cys Thr Gly Cys Thr Cys Cys Gly Cys Cys Gly Ala
1185                 1190                1195                1200
Cys Ala Cys Cys Thr Gly Ala Thr Ala Thr Thr Cys Thr Thr Cys Ala
                1205                1210                1215
Cys Gly Ala Cys Gly Thr Cys Cys Gly Cys Cys Thr Thr Gly Cys Cys
        1220                1225                1230
Gly Ala Ala Thr Gly Cys Ala Cys Ala Thr Gly Cys Ala Ala Cys Gly
         1235                1240                1245
Cys Gly Gly Cys Thr Cys Cys Ala Ala Cys Cys Thr Cys Gly Ala Thr
        1250                1255                1260
Cys Ala Thr Cys Gly Cys Cys Gly Thr Cys Ala Thr Cys Ala Ala Gly
1265                 1270                1275                1280
Cys Ala Gly Thr Cys Gly Ala Ala Thr Cys Gly Ala Thr Thr Cys Thr
         1285                1290                1295
Gly Thr Gly Thr Cys Ala Gly Thr Cys Ala Cys Ala Gly Thr Cys Ala
        1300                1305                1310
Cys Ala Thr Thr Gly Ala Cys Ala Thr Cys Gly Thr Cys Ala Gly Cys
        1315                1320                1325
Cys Gly Thr Gly Cys Cys Gly Cys Gly Thr Thr Thr Cys Cys Thr Cys
        1330                1335                1340
Thr Thr Gly Thr Thr Thr Thr Cys Ala Thr Cys Thr Gly Thr Thr
1345                 1350                1355                1360
Cys Ala Ala Cys Ala Cys Thr Cys Thr Thr Thr Cys Thr Gly Gly
                1365                1370                1375
Cys Thr Gly Ala Thr Cys Thr Ala Cys Thr Gly Thr Ala Cys Ala
         1380                1385                1390
Ala Ala Thr Cys Cys Ala Ala Gly Cys Gly Thr Cys Thr Gly Cys Cys
        1395                1400                1405
Gly Thr Ala Thr Ala Thr Thr Ala Gly Thr Gly Ala Ala Cys Ala Cys
```

-continued

Gly Ala Gly Gly Thr Gly Ala Cys Cys Thr Thr Gly Cys Gly
1425                1430                1435                1440
Ala Thr Gly Cys Thr Cys Cys Ala Gly Ala Cys Cys Thr Thr Cys Ala
        1445                1450                1455
Thr Thr Ala Ala Thr Cys Thr Cys Ala Ala Thr Cys Cys Ala Ala Cys
        1460                1465                1470
Thr Cys Cys Thr Cys Ala Thr Cys Ala Thr Thr Thr Cys Cys
    1475                1480                1485
Ala Thr Thr Thr Cys Gly Ala Ala Thr Ala Thr Cys Thr Thr
    1490                1495                1500
Thr Thr Thr Cys Thr Thr Gly Cys Ala Cys Ala Gly Ala Ala Gly Cys
1505                1510                1515                1520
Cys Thr Thr Thr Thr Thr Thr Cys Gly Thr Thr Thr Thr Thr Thr
        1525                1530                1535
Thr Thr Ala Thr Thr Gly Ala Thr Thr Thr Ala Thr Thr Thr Thr Thr
        1540                1545                1550
Ala Cys Gly Gly Ala Thr Thr Thr Thr Ala Gly Ala Thr Ala Ala
        1555                1560                1565
Thr Gly Cys Ala Cys Ala Gly Ala Thr Gly Cys Cys Thr Cys Ala Thr
1570                1575                1580
Thr Gly Cys Thr Cys Ala Ala Ala Thr Ala Ala Ala Thr Thr Thr Ala
1585                1590                1595                1600
Thr Thr Thr Thr Ala Ala Thr Thr Gly Thr Cys Gly Ala Ala Ala Ala
                1605                1610                1615
Ala Ala Ala Ala Ala Ala Ala Ala Ala Ala Ala Ala Ala Ala
            1620                1625                1630
Ala Ala Ala Ala Ala Ala Ala Ala Ala Ala Ala Ala Ala Ala
            1635                1640                1645
Ala Ala Ala Ala
    1650

<210> SEQ ID NO 2
<211> LENGTH: 1652
<212> TYPE: DNA
<213> ORGANISM: Caenorhabditis elegans

<400> SEQUENCE: 2
cggaaaaacc tccccaacat tggctcacac ccggattatg atcttctgct gctcctgctg      60
ctccttctgc tgtagttgag acgaagaaga agaagaagct ccattctcga gaaatggctc     120
gtccattcac acttatcgta ctcctctccg cacatctgtg tctacatgtg ttgtgacac      180
aggatgagga ctcacatatc aacactcaac tcctctcatc agttctcgat agactcacga     240
atcgcactac ttatgataaa agattacggc ccaggtatgg tgaaaagcca gtcgacgttg     300
gaattacgat acacgtttct tcaatctctg cagtttcaga agttgatatg gacttcacat     360
tagacttcta catgcgtcaa acgtggcaag accctcgact agccttcgga agtcttgatt     420
tgggactttc caaagaaatc gactcactta ccgtcggagt agactacctg gatagactgt     480
ggaaacccga cacgttcttc ccaaatgaaa agaaatcatt cttccacttg caaccacac      540
ataactcgtt ccttcgtatc gagggtgatg gaacggttta ctagtcaa agattaacag     600
tcactgcaac gtgtccaatg gacctgaagc tgttcccaat ggactctcaa cactgtaaac     660
tggaaattga aagctatgcg tattcgacgg ccgaaatcga gtacaaatgg tgtacgtcga     720

-continued

```
aggagccgaa ttgttcgaca gcggtcaagg ccgacgcgaa catcgaactg tcgagttata    780
aattcactaa aatctgccaa aaacggacac ttgccagcac ttcatcgggg acctactctc    840
gtctacgggt tagtttcata tttgatcgcg acagcggctt ctactttctt caaatatttt    900
tccctgccag cctcgtcgta gttttatcat ggatctcatt ctggatcaat cgtgactcgg    960
cgccttcgcg aaccctaatc ggtacgatga cggtgctcac tgagactcat cttatgaccg   1020
gaaccaatcg acgtcttcca ccagttgcct atgtaaaagc cgttgatgta ttcctcggtt   1080
tctgctatct tctggttata ctggcgttga tcgagtacgc ctgtgttgcc tactcaaaaa   1140
agaagaacga ggatcgtcgg agaagagaga agaagacgag gcataaacct gctccgccga   1200
cacctgatat tcttcacgac gtccgccttg ccgaatgcac atgcaacgcg gctccaacct   1260
cgatcatcgc cgtcatcaag cagtcgaatc gattctgtgt cagtcacagt cacattgaca   1320
tcgtcagccg tgccgcgttt cctcttgttt tcatcttgtt caacactctc ttctggctga   1380
ttctactgta caaatccaag cgtctgccgt atattagtga acacgagggt gaccgttgcg   1440
atgctccaga ccttcattaa tctcaatcca acttcctcat cattttccat ttcgaatatc   1500 tcttttctt gcacagaagc cttttttcgt ttttttttat tgatttattt ttacggattt   1560
ttagataatg cacagatgcc tcattgctca aataaattta ttttaattgt cgaaaaaaaa   1620 aaaaaaaaa aaaaaaaaaa aaaaaaaaaa aa                                  1652
```

<210> SEQ ID NO 3
<211> LENGTH: 2544
<212> TYPE: PRT
<213> ORGANISM: Caenorhabditis elegans

<400> SEQUENCE: 3

```
Ala Ala Gly Thr Thr Thr Gly Ala Gly Ala Gly Thr Gly Ala Thr Ala
  1               5                  10                  15

Thr Ala Gly Gly Ala Gly Ala Ala Ala Ala Cys Cys Thr Cys Cys
             20                  25                  30

Cys Cys Ala Ala Cys Ala Thr Thr Gly Gly Cys Thr Cys Ala Cys Ala
         35                  40                  45

Cys Cys Cys Gly Gly Ala Thr Thr Ala Thr Gly Ala Thr Cys Thr Thr
     50                  55                  60

Cys Thr Gly Cys Thr Gly Cys Thr Cys Thr Gly Cys Thr Gly Cys
 65                  70                  75                  80

Thr Cys Cys Thr Thr Cys Thr Gly Cys Thr Gly Thr Ala Gly Thr Thr
                 85                  90                  95

Gly Ala Gly Ala Cys Gly Ala Ala Gly Ala Ala Gly Ala Ala Gly Ala
            100                 105                 110

Ala Gly Ala Ala Gly Cys Thr Cys Cys Ala Thr Thr Cys Thr Cys Gly
        115                 120                 125

Ala Gly Ala Ala Ala Thr Gly Gly Cys Thr Cys Gly Thr Cys Cys Ala
    130                 135                 140

Thr Thr Cys Ala Cys Ala Cys Thr Thr Ala Thr Cys Gly Thr Ala Cys
145                 150                 155                 160

Thr Cys Cys Thr Cys Thr Cys Cys Gly Cys Ala Cys Ala Thr Cys Thr
                165                 170                 175

Gly Thr Gly Thr Cys Thr Ala Cys Ala Thr Gly Thr Gly Gly Thr Thr
            180                 185                 190

Gly Thr Gly Ala Cys Ala Cys Ala Gly Gly Ala Thr Gly Ala Gly Gly
        195                 200                 205
```

-continued

```
Ala Cys Thr Cys Ala Cys Ala Thr Ala Thr Cys Ala Ala Cys Ala Cys
    210                 215                 220
Thr Cys Ala Ala Cys Thr Cys Cys Thr Cys Thr Cys Ala Thr Cys Ala
225                 230                 235                 240

Gly Thr Thr Cys Thr Cys Gly Ala Thr Ala Gly Ala Cys Thr Cys Ala
                245                 250                 255
Cys Gly Ala Ala Thr Cys Gly Cys Ala Cys Thr Ala Cys Thr Thr Ala
            260                 265                 270

Thr Gly Ala Thr Ala Ala Ala Ala Gly Ala Thr Thr Ala Cys Gly Gly
        275                 280                 285
Cys Cys Cys Ala Gly Gly Thr Ala Thr Gly Gly Thr Gly Ala Ala Ala
    290                 295                 300
Ala Gly Cys Cys Ala Gly Thr Cys Gly Ala Cys Gly Thr Thr Gly Gly
305                 310                 315                 320
Ala Ala Thr Thr Ala Cys Gly Ala Thr Ala Cys Ala Cys Gly Thr Thr
                325                 330                 335
Thr Cys Thr Thr Cys Ala Ala Thr Cys Thr Cys Thr Gly Cys Ala Gly
            340                 345                 350
Thr Thr Thr Cys Ala Gly Ala Ala Gly Thr Thr Gly Ala Thr Ala Thr
        355                 360                 365

Gly Gly Ala Cys Thr Thr Cys Ala Cys Ala Thr Thr Ala Gly Ala Cys
    370                 375                 380

Thr Thr Cys Thr Ala Cys Ala Thr Gly Cys Gly Thr Cys Ala Ala Ala
385                 390                 395                 400

Cys Gly Thr Gly Gly Cys Ala Ala Gly Ala Cys Cys Cys Thr Cys Gly
                405                 410                 415

Ala Cys Thr Ala Gly Cys Cys Thr Thr Cys Gly Gly Ala Ala Gly Thr
            420                 425                 430

Cys Thr Thr Gly Ala Thr Thr Thr Gly Gly Gly Ala Cys Thr Thr Thr
        435                 440                 445

Cys Cys Ala Ala Ala Gly Ala Ala Ala Thr Cys Gly Ala Cys Thr Cys
    450                 455                 460

Ala Cys Thr Thr Ala Cys Cys Gly Thr Cys Gly Gly Ala Gly Thr Ala
465                 470                 475                 480

Gly Ala Cys Thr Ala Cys Cys Thr Gly Gly Ala Thr Ala Gly Ala Cys
                485                 490                 495

Thr Gly Thr Gly Gly Ala Ala Ala Cys Cys Cys Gly Ala Cys Ala Cys
            500                 505                 510

Gly Thr Thr Cys Thr Thr Cys Cys Cys Ala Ala Ala Thr Gly Ala Ala
        515                 520                 525

Ala Ala Gly Ala Ala Ala Thr Cys Ala Thr Thr Cys Thr Thr Cys Cys
    530                 535                 540

Ala Cys Thr Thr Gly Gly Cys Ala Ala Cys Cys Ala Cys Ala Cys Ala
545                 550                 555                 560

Thr Ala Ala Cys Thr Cys Gly Thr Thr Cys Cys Thr Thr Cys Gly Thr
                565                 570                 575

Ala Thr Cys Gly Ala Gly Gly Gly Thr Gly Ala Thr Gly Gly Ala Ala
            580                 585                 590

Cys Gly Gly Thr Thr Thr Ala Thr Ala Cys Thr Ala Gly Thr Cys Ala
        595                 600                 605

Ala Ala Gly Ala Thr Thr Ala Ala Cys Ala Gly Thr Cys Ala Cys Thr
    610                 615                 620

Gly Cys Ala Ala Cys Gly Thr Gly Thr Cys Cys Ala Ala Thr Gly Gly
```

-continued

```
625                 630                 635                 640

Ala Cys Cys Thr Gly Ala Ala Gly Cys Thr Gly Thr Thr Cys Cys Cys
                645                 650                 655
Ala Ala Thr Gly Gly Ala Cys Thr Cys Thr Cys Ala Ala Cys Ala Cys
            660                 665                 670

Thr Gly Thr Ala Ala Ala Cys Thr Gly Gly Ala Ala Ala Thr Thr Gly
        675                 680                 685

Ala Ala Ala Gly Cys Thr Ala Cys Gly Gly Gly Thr Ala Cys Gly Ala
    690                 695                 700

Gly Ala Cys Gly Ala Ala Ala Gly Ala Thr Ala Thr Cys Gly Ala Cys
705                 710                 715                 720

Thr Ala Cys Thr Ala Thr Thr Gly Gly Gly Gly Gly Ala Ala Gly Ala
                725                 730                 735

Ala Gly Cys Gly Gly Ala Cys Thr Gly Ala Thr Thr Thr Gly Gly Ala
            740                 745                 750

Gly Ala Thr Ala Ala Cys Gly Gly Cys Thr Gly Thr Cys Ala Ala Gly
        755                 760                 765

Thr Thr Thr Gly Ala Thr Ala Cys Cys Thr Thr Cys Cys Ala Gly Thr
    770                 775                 780

Thr Gly Cys Cys Gly Cys Ala Gly Thr Thr Thr Cys Ala Gly Cys Cys
785                 790                 795                 800

Ala Ala Cys Gly Cys Thr Gly Thr Ala Thr Thr Thr Gly Thr Gly
                805                 810                 815

Ala Ala Thr Ala Cys Ala Ala Cys Thr Ala Ala Ala Gly Cys Cys Gly
            820                 825                 830

Ala Gly Ala Cys Cys Thr Cys Ala Thr Cys Ala Gly Gly Ala Ala Ala
        835                 840                 845

Ala Thr Ala Cys Gly Thr Ala Cys Gly Cys Cys Thr Gly Gly Cys Gly
    850                 855                 860

Cys Thr Gly Gly Ala Ala Gly Thr Ala Ala Thr Ala Thr Thr Gly Gly
865                 870                 875                 880

Thr Thr Cys Gly Ala Ala Ala Thr Ala Thr Gly Gly Gly Cys Thr Thr
                885                 890                 895

Cys Thr Ala Cys Ala Cys Thr Ala Thr Gly Ala Ala Cys Ala Thr Cys
            900                 905                 910

Gly Thr Cys Ala Thr Cys Cys Cys Ala Thr Cys Cys Ala Thr Cys Cys
        915                 920                 925

Thr Gly Ala Thr Cys Gly Thr Cys Ala Cys Cys Ala Thr Ala Thr Cys
    930                 935                 940

Thr Thr Gly Gly Gly Thr Ala Thr Cys Ala Thr Thr Thr Thr Gly Gly
945                 950                 955                 960

Thr Thr Gly Ala Ala Thr Cys Gly Ala Gly Ala Ala Gly Cys Thr Thr
                965                 970                 975

Cys Gly Cys Cys Gly Gly Cys Thr Cys Gly Ala Gly Thr Thr Gly Gly
            980                 985                 990

Ala Thr Thr Gly Gly Gly Thr Gly Thr Gly Ala Cys Thr Ala Cys Thr
        995                 1000                1005

Gly Thr Gly Cys Thr Cys Ala Cys Ala Ala Thr Gly Ala Cys Ala Ala
    1010                1015                1020

Cys Thr Cys Thr Gly Ala Thr Cys Ala Cys Thr Ala Cys Ala Ala Cys
1025                1030                1035                1040

Cys Ala Ala Thr Ala Ala Thr Thr Cys Gly Ala Thr Gly Cys Cys Ala
                1045                1050                1055
```

-continued

```
Ala Ala Ala Gly Thr Gly Thr Cys Thr Thr Ala Thr Gly Thr Cys Ala
            1060                1065                1070
Ala Gly Gly Gly Thr Cys Thr Gly Gly Ala Thr Gly Thr Gly Thr Thr
        1075                1080                1085

Thr Cys Thr Thr Ala Ala Thr Thr Thr Thr Thr Gly Thr Thr Thr Cys
    1090                1095                1100

Gly Thr Ala Ala Thr Gly Gly Thr Ala Thr Thr Cys Gly Cys Cys Thr
1105                1110                1115                1120
Cys Gly Thr Thr Gly Cys Thr Cys Gly Ala Gly Thr Ala Cys Gly Cys
                1125                1130                1135

Cys Ala Thr Ala Gly Thr Ala Thr Cys Cys Thr Ala Cys Ala Thr Gly
            1140                1145                1150
Ala Ala Thr Ala Ala Ala Cys Gly Ala Cys Thr Gly Gly Thr Cys Cys
        1155                1160                1165

Thr Cys Cys Gly Ala Cys Gly Gly Gly Ala Ala Ala Ala Ala Cys Gly
    1170                1175                1180

Ala Ala Gly Ala Ala Ala Ala Gly Cys Cys Gly Cys Cys Gly Ala Ala
1185                1190                1195                1200
Cys Ala Ala Cys Ala Gly Cys Ala Gly Cys Gly Ala Ala Ala Cys Gly
                1205                1210                1215

Ala Gly Ala Thr Gly Cys Cys Ala Ala Thr Gly Thr Thr Cys Ala Ala
            1220                1225                1230

Cys Gly Cys Gly Ala Gly Cys Cys Cys Gly Ala Ala Gly Gly Cys Cys
        1235                1240                1245

Gly Cys Cys Ala Ala Thr Ala Ala Thr Ala Ala Thr Gly Cys Thr Gly
    1250                1255                1260

Ala Cys Thr Thr Gly Thr Ala Cys Thr Thr Thr Gly Cys Cys Gly Gly
1265                1270                1275                1280
Ala Cys Ala Cys Ala Ala Thr Thr Cys Cys Thr Cys Thr Ala Thr Gly
                1285                1290                1295

Ala Ala Thr Cys Cys Ala Thr Thr Gly Ala Thr Gly Gly Ala Gly Ala
            1300                1305                1310

Thr Cys Cys Cys Ala Gly Ala Ala Ala Ala Thr Thr Gly Thr Gly Ala
        1315                1320                1325

Thr Thr Gly Cys Cys Gly Gly Ala Cys Gly Ala Thr Thr Cys Cys Ala
    1330                1335                1340

Ala Thr Gly Ala Thr Gly Cys Ala Ala Cys Ala Thr Cys Cys Ala Cys
1345                1350                1355                1360

Gly Thr Cys Thr Thr Gly Thr Cys Ala Cys Ala Gly Ala Cys Gly Gly
                1365                1370                1375

Cys Gly Cys Ala Cys Ala Thr Ala Cys Gly Cys Thr Ala Thr Gly Gly
            1380                1385                1390

Cys Cys Gly Gly Cys Thr Cys Cys Ala Thr Thr Cys Gly Cys Gly Cys
        1395                1400                1405

Gly Gly Cys Cys Gly Ala Ala Ala Ala Ala Gly Gly Cys Thr Thr Cys
    1410                1415                1420

Cys Ala Ala Gly Ala Cys Ala Thr Gly Cys Thr Gly Cys Cys Ala Ala
1425                1430                1435                1440

Cys Gly Ala Thr Gly Gly Ala Cys Gly Cys Cys Thr Gly Cys Ala Ala
                1445                1450                1455

Ala Ala Ala Thr Cys Gly Ala Thr Ala Ala Gly Cys Thr Thr Ala Gly
            1460                1465                1470
```

-continued

```
Cys Cys Gly Ala Thr Ala Cys Gly Gly Thr Thr Thr Cys Cys Cys Ala
        1475                1480                1485

Thr Thr Gly Thr Cys Thr Thr Thr Cys Thr Cys Thr Ala Thr Cys Thr
    1490                1495                1500

Thr Cys Ala Ala Thr Ala Thr Ala Gly Thr Cys Thr Ala Cys Thr Gly
1505                1510                1515                1520

Gly Thr Thr Gly Thr Ala Thr Ala Thr Gly Ala Ala Ala Thr Ala Thr
                1525                1530                1535

Cys Thr Ala Ala Gly Cys Thr Thr Ala Ala Ala Cys Thr Cys Gly Thr
            1540                1545                1550

Cys Gly Gly Ala Cys Ala Ala Gly Ala Thr Cys Cys Ala Gly Gly Ala
        1555                1560                1565

Gly Ala Ala Cys Gly Ala Cys Ala Ala Gly Thr Gly Gly Cys Ala Gly
    1570                1575                1580

Cys Ala Gly Ala Thr Cys Cys Ala Cys Thr Gly Ala Thr Gly Cys Gly
1585                1590                1595                1600

Thr Ala Thr Thr Cys Gly Ala Cys Gly Gly Cys Cys Gly Ala Ala Ala
                1605                1610                1615

Thr Cys Gly Ala Gly Thr Ala Cys Ala Ala Ala Thr Gly Gly Thr Gly
            1620                1625                1630

Thr Ala Cys Gly Thr Cys Gly Ala Ala Gly Gly Ala Gly Cys Cys Gly
        1635                1640                1645

Ala Ala Thr Thr Gly Thr Thr Cys Gly Ala Cys Ala Gly Cys Gly Gly
    1650                1655                1660

Thr Cys Ala Ala Gly Gly Cys Cys Gly Ala Cys Gly Cys Gly Ala Ala
1665                1670                1675                1680

Cys Ala Thr Cys Gly Ala Ala Cys Thr Gly Thr Cys Gly Ala Gly Thr
                1685                1690                1695

Thr Ala Thr Ala Ala Ala Thr Thr Cys Ala Cys Thr Ala Ala Ala Ala
            1700                1705                1710

Thr Cys Thr Gly Cys Cys Ala Ala Ala Ala Ala Cys Gly Gly Ala Cys
        1715                1720                1725

Ala Cys Thr Thr Gly Cys Cys Ala Gly Cys Ala Cys Thr Thr Cys Ala
    1730                1735                1740

Thr Cys Gly Gly Gly Gly Ala Cys Cys Thr Ala Cys Thr Cys Thr Cys
1745                1750                1755                1760

Gly Thr Cys Thr Ala Cys Gly Gly Gly Thr Thr Ala Gly Thr Thr Thr
                1765                1770                1775

Cys Ala Thr Ala Thr Thr Thr Gly Ala Thr Cys Gly Cys Gly Ala Cys
            1780                1785                1790

Ala Gly Cys Gly Gly Cys Thr Thr Cys Thr Ala Cys Thr Thr Thr Cys
        1795                1800                1805

Thr Thr Cys Ala Ala Ala Thr Ala Thr Thr Thr Thr Thr Cys Cys Cys
    1810                1815                1820

Thr Gly Cys Cys Ala Gly Cys Cys Thr Cys Gly Thr Cys Gly Thr Ala
1825                1830                1835                1840

Gly Thr Thr Thr Thr Ala Thr Cys Ala Thr Gly Gly Ala Thr Cys Thr
                1845                1850                1855

Cys Ala Thr Thr Cys Thr Gly Gly Ala Thr Cys Ala Ala Thr Cys Gly
            1860                1865                1870

Thr Gly Ala Cys Thr Cys Gly Gly Cys Gly Cys Cys Thr Thr Cys Gly
        1875                1880                1885

Cys Gly Ala Ala Cys Cys Cys Thr Ala Ala Thr Cys Gly Gly Thr Ala
```

-continued

```
    1890                1895                1900

Cys Gly Ala Thr Gly Ala Cys Gly Gly Thr Gly Cys Thr Cys Ala Cys
1905                1910                1915                1920

Thr Gly Ala Gly Ala Cys Thr Cys Ala Thr Cys Thr Thr Ala Thr Gly
                1925                1930                1935

Ala Cys Cys Gly Gly Ala Ala Cys Cys Ala Ala Thr Cys Gly Ala Cys
            1940                1945                1950

Gly Thr Cys Thr Thr Cys Cys Ala Cys Cys Ala Gly Thr Thr Gly Cys
        1955                1960                1965

Cys Thr Ala Thr Gly Thr Ala Ala Ala Ala Gly Cys Cys Gly Thr Thr
    1970                1975                1980

Gly Ala Thr Gly Thr Ala Thr Thr Cys Cys Thr Cys Gly Gly Thr Thr
1985                1990                1995                2000

Thr Cys Thr Gly Cys Thr Ala Thr Cys Thr Thr Cys Thr Gly Gly Thr
                2005                2010                2015

Thr Ala Thr Ala Cys Thr Gly Gly Cys Gly Thr Thr Gly Ala Thr Cys
            2020                2025                2030

Gly Ala Gly Thr Ala Cys Gly Cys Cys Thr Gly Thr Gly Thr Thr Gly
        2035                2040                2045

Cys Cys Thr Ala Cys Thr Cys Ala Ala Ala Ala Ala Ala Gly Ala Ala
    2050                2055                2060

Gly Ala Ala Cys Gly Ala Gly Gly Ala Thr Cys Gly Thr Cys Gly Gly
2065                2070                2075                2080

Ala Gly Ala Ala Gly Ala Gly Ala Gly Ala Ala Gly Ala Ala Gly Ala
                2085                2090                2095

Cys Gly Gly Ala Gly Cys Ala Thr Ala Ala Ala Cys Cys Thr Gly Cys
            2100                2105                2110

Thr Cys Cys Gly Cys Cys Gly Ala Cys Ala Cys Cys Thr Gly Ala Thr
        2115                2120                2125

Ala Thr Thr Cys Thr Thr Cys Ala Cys Gly Ala Cys Gly Thr Cys Cys
    2130                2135                2140

Gly Cys Cys Thr Thr Gly Cys Cys Gly Ala Ala Thr Gly Cys Ala Cys
2145                2150                2155                2160

Ala Thr Gly Cys Ala Ala Cys Gly Cys Gly Gly Cys Thr Cys Cys Ala
                2165                2170                2175

Ala Cys Cys Thr Cys Gly Ala Thr Cys Ala Thr Cys Gly Cys Cys Gly
            2180                2185                2190

Thr Cys Ala Thr Cys Ala Ala Gly Cys Ala Gly Thr Cys Gly Ala Ala
        2195                2200                2205

Thr Cys Gly Ala Thr Thr Cys Thr Gly Thr Gly Thr Cys Ala Gly Thr
    2210                2215                2220

Cys Ala Cys Ala Gly Thr Cys Ala Cys Ala Thr Thr Gly Ala Cys Ala
2225                2230                2235                2240

Thr Cys Gly Thr Cys Ala Gly Cys Cys Gly Thr Gly Cys Cys Gly Cys
                2245                2250                2255

Gly Thr Thr Thr Cys Cys Thr Cys Thr Thr Gly Thr Thr Thr Thr Cys
            2260                2265                2270

Ala Thr Cys Thr Thr Gly Thr Thr Cys Ala Ala Cys Ala Cys Thr Cys
        2275                2280                2285

Thr Cys Thr Thr Cys Thr Gly Gly Cys Thr Gly Ala Thr Thr Cys Thr
    2290                2295                2300

Ala Cys Thr Gly Thr Ala Cys Ala Ala Ala Thr Cys Cys Ala Ala Gly
2305                2310                2315                2320
```

-continued

Cys Gly Thr Cys Thr Gly Cys Cys Gly Thr Ala Thr Ala Thr Ala
                2325                2330                2335
Gly Thr Gly Ala Ala Cys Ala Cys Gly Ala Gly Gly Thr Gly Ala
                2340                2345                2350
Cys Cys Gly Thr Thr Gly Cys Gly Ala Thr Gly Cys Thr Cys Ala
                2355                2360                2365
Gly Ala Cys Cys Thr Thr Cys Ala Thr Ala Thr Cys Thr Cys
        2370                2375                2380
Ala Ala Thr Cys Cys Ala Ala Cys Thr Cys Cys Thr Cys Ala Thr
2385                2390                2395                2400
Cys Ala Thr Thr Thr Thr Cys Cys Ala Thr Thr Cys Gly Ala Ala
                2405                2410                2415
Thr Ala Thr Cys Thr Cys Thr Thr Thr Thr Cys Thr Thr Gly Cys
                2420                2425                2430
Ala Cys Ala Gly Ala Ala Gly Cys Cys Thr Thr Thr Thr Thr Cys
                2435                2440                2445
Gly Thr Thr Thr Thr Thr Thr Thr Ala Thr Thr Gly Ala Thr
                2450                2455                2460
Thr Thr Ala Thr Thr Thr Thr Thr Ala Cys Gly Gly Ala Thr Thr Thr
2465                2470                2475                2480
Thr Thr Ala Gly Ala Thr Ala Ala Thr Gly Cys Ala Cys Ala Gly Ala
                2485                2490                2495
Thr Gly Cys Cys Thr Cys Ala Thr Thr Gly Cys Thr Cys Ala Ala Ala
                2500                2505                2510
Thr Ala Ala Ala Thr Thr Thr Ala Thr Thr Thr Thr Ala Ala Thr Thr
                2515                2520                2525
Ala Ala Ala Ala Ala Ala Ala Ala Ala Ala Ala Ala Ala Ala Ala
                2530                2535                2540

<210> SEQ ID NO 4
<211> LENGTH: 2544
<212> TYPE: DNA
<213> ORGANISM: Caenorhabditis elegans

<400> SEQUENCE: 4
aagtttgaga gtgatatagg agaaaaacct ccccaacatt ggctcacacc cggattatga      60
tcttctgctg ctcctgctgc tccttctgct gtagttgaga cgaagaagaa gaagaagctc     120
cattctcgag aaatggctcg tccattcaca cttatcgtac tcctctccgc acatctgtgt     180
ctacatgtgg ttgtgacaca ggatgaggac tcacatatca acactcaact cctctcatca     240
gttctcgata gactcacgaa tcgcactact tatgataaaa gattacggcc caggtatggt     300
gaaaagccag tcgacgttgg aattacgata cacgtttctt caatctctgc agtttcagaa     360
gttgatatgg acttcacatt agacttctac atgcgtcaaa cgtggcaaga ccctcgacta     420
gccttcggaa gtcttgattt gggactttcc aaagaaatcg actcacttac cgtcggagta     480
gactacctgg atagactgtg gaaacccgac acgttcttcc caaatgaaaa gaaatcattc     540
ttccacttgg caaccacaca taactcgttc cttcgtatcg agggtgatgg aacggtttat     600
actagtcaaa gattaacagt cactgcaacg tgtccaatgg acctgaagct gttcccaatg     660
gactctcaac actgtaaact ggaaattgaa agctacgggt acgagacgaa agatatcgac     720
tactattggg ggaagaagcg gactgatttg gagataacgg ctgtcaagtt tgataccttc     780
cagttgccgc agtttcagcc aacgctgtat tttgtgaata caactaaagc cgagacctca     840

-continued

```
tcaggaaaat acgtacgcct ggcgctggaa gtaatattgg ttcgaaatat gggcttctac      900
actatgaaca tcgtcatccc atccatcctg atcgtcacca tatcttgggt atcattttgg     960
ttgaatcgag aagcttcgcc ggctcgagtt ggattgggtg tgactactgt gctcacaatg    1020
acaactctga tcactacaac caataattcg atgccaaaag tgtcttatgt caagggtctg    1080
gatgtgtttc ttaattttg tttcgtaatg gtattcgcct cgttgctcga gtacgccata     1140
gtatcctaca tgaataaacg actggtcctc cgacgggaaa aacgaagaaa agccgccgaa    1200
caacagcagc gaaacgagat gccaatgttc aacgcgagcc cgaaggccgc caataataat    1260
gctgacttgt actttgccgg acacaattcc tctatgaatc cattgatgga gatcccagaa    1320
aattgtgatt gccggacgat tccaatgatg caacatccac gtcttgtcac agacggcgca    1380
catacgctat ggccggctcc attcgcgcgg ccgaaaaagg cttccaagac atgctgccaa    1440
cgatggacgc ctgcaaaaat cgataagctt agccgatacg gtttcccatt gtctttctct    1500
atcttcaata tagtctactg gttgtatatg aaatatctaa gcttaaactc gtcggacaag    1560
atccaggaga acgacaagtg gcagcagatc cactgatgcg tattcgacgg ccgaaatcga    1620
gtacaaatgg tgtacgtcga aggagccgaa ttgttcgaca gcggtcaagg ccgacgcgaa    1680
catcgaactg tcgagttata aattcactaa aatctgccaa aaacggacac ttgccagcac    1740
ttcatcgggg acctactctc gtctacgggt tagtttcata tttgatcgcg acagcggctt    1800
ctactttctt caaatatttt tccctgccag cctcgtcgta gttttatcat ggatctcatt    1860
ctggatcaat cgtgactcgg cgccttcgcg aaccctaatc ggtacgatga cggtgctcac    1920
tgagactcat cttatgaccg gaaccaatcg acgtcttcca ccagttgcct atgtaaaagc    1980
cgttgatgta ttcctcggtt tctgctatct tctggttata ctggcgttga tcgagtacgc    2040
ctgtgttgcc tactcaaaaa agaagaacga ggatcgtcgg agaagagaga agaagacgga    2100
gcataaacct gctccgccga cacctgatat tcttcacgac gtccgccttg ccgaatgcac    2160
atgcaacgcg gctccaacct cgatcatcgc cgtcatcaag cagtcgaatc gattctgtgt    2220
cagtcacagt cacattgaca tcgtcagccg tgccgcgttt cctcttgttt tcatcttgtt    2280
caacactctc ttctggctga ttctactgta caaatccaag cgtctgccgt atattagtga    2340
acacgagggt gaccgttgcg atgctccaga cctttcattaa tctcaatcca acttcctcat    2400
cattttccat ttcgaatatc tcttttttctt gcacagaagc cttttttcgt ttttttttat    2460
tgatttattt ttacggattt ttagataatg cacagatgcc tcattgctca aataaattta    2520
ttttaattaa aaaaaaaaaa aaaa                                           2544
```

<210> SEQ ID NO 5
<211> LENGTH: 1917
<212> TYPE: PRT
<213> ORGANISM: Caenorhabditis elegans

<400> SEQUENCE: 5

```
Gly Ala Thr Cys Cys Cys Ala Gly Cys Gly Cys Thr Cys Cys
 1               5                  10                  15

Cys Cys Gly Thr Thr Ala Cys Cys Thr Cys Gly Thr Gly Thr Thr
                20                  25                  30

Cys Thr Cys Cys Gly Thr Gly Thr Thr Gly Gly Cys Thr Cys Ala Ala
            35                  40                  45

Cys Thr Thr Gly Thr Gly Cys Gly Thr Gly Thr Thr Thr Thr Ala Cys
        50                  55                  60

Ala Thr Cys Thr Cys Thr Cys Thr Gly Thr Cys Thr Cys Thr Cys Thr
```

-continued

```
 65                  70                  75                  80

Cys Thr Cys Ala Thr Cys Ala Thr Cys Ala Thr Cys Ala Thr Cys Thr
                85                  90                  95

Thr Ala Thr Thr Cys Thr Gly Thr Gly Cys Thr Cys Cys Cys Gly Cys
            100                 105                 110

Thr Ala Ala Cys Cys Gly Ala Thr Thr Gly Gly Cys Thr Cys Ala Thr
        115                 120                 125

Thr Cys Thr Cys Thr Thr Cys Gly Gly Cys Thr Cys Thr Thr Gly Thr
    130                 135                 140

Cys Ala Cys Thr Ala Ala Cys Gly Ala Ala Thr Cys Gly Cys Thr Thr
145                 150                 155                 160
Thr Thr Cys Ala Cys Ala Cys Ala Gly Ala Gly Thr Gly Ala Thr Ala
                165                 170                 175

Thr Ala Gly Gly Ala Gly Ala Ala Ala Ala Ala Cys Cys Thr Cys Cys
            180                 185                 190

Cys Cys Ala Ala Cys Ala Thr Thr Gly Gly Cys Thr Cys Ala Cys Ala
        195                 200                 205

Cys Cys Cys Gly Gly Ala Thr Thr Ala Thr Gly Ala Thr Cys Thr Thr
    210                 215                 220

Cys Thr Gly Cys Thr Gly Cys Thr Cys Cys Thr Gly Cys Thr Gly Cys
225                 230                 235                 240

Thr Cys Cys Thr Thr Cys Thr Gly Cys Thr Gly Thr Ala Gly Thr Thr
                245                 250                 255
Gly Ala Gly Ala Cys Gly Ala Ala Gly Ala Ala Gly Ala Ala Gly Ala
            260                 265                 270

Ala Gly Ala Ala Gly Cys Thr Cys Cys Ala Thr Thr Cys Thr Cys Gly
        275                 280                 285

Ala Gly Ala Ala Ala Thr Gly Gly Cys Thr Cys Gly Thr Cys Cys Ala
    290                 295                 300

Thr Thr Cys Ala Cys Ala Cys Thr Thr Ala Thr Cys Gly Thr Ala Cys
305                 310                 315                 320
Thr Cys Cys Thr Cys Thr Cys Cys Gly Cys Ala Cys Ala Thr Cys Thr
                325                 330                 335
Gly Thr Gly Thr Cys Thr Ala Cys Ala Thr Gly Thr Gly Gly Thr Thr
            340                 345                 350

Gly Thr Gly Ala Cys Ala Cys Ala Gly Gly Ala Thr Gly Ala Gly Gly
        355                 360                 365

Ala Cys Thr Cys Ala Cys Ala Thr Ala Thr Cys Ala Ala Cys Ala Cys
    370                 375                 380

Thr Cys Ala Ala Cys Thr Cys Cys Thr Cys Thr Cys Ala Thr Cys Ala
385                 390                 395                 400
Gly Thr Thr Cys Thr Cys Gly Ala Thr Ala Gly Ala Cys Thr Cys Ala
                405                 410                 415
Cys Gly Ala Ala Thr Cys Gly Cys Ala Cys Thr Ala Cys Thr Thr Ala
            420                 425                 430

Thr Gly Ala Thr Ala Ala Ala Ala Gly Ala Thr Thr Ala Cys Gly Gly
        435                 440                 445

Cys Cys Cys Ala Gly Gly Thr Ala Thr Gly Gly Thr Gly Ala Ala Ala
    450                 455                 460

Ala Gly Cys Cys Ala Gly Thr Cys Gly Ala Cys Gly Thr Thr Gly Gly
465                 470                 475                 480

Ala Ala Thr Thr Ala Cys Gly Ala Thr Ala Cys Ala Cys Gly Thr Thr
                485                 490                 495
```

-continued

```
Thr Cys Thr Thr Cys Ala Ala Thr Cys Thr Cys Thr Gly Cys Ala Gly
            500                 505                 510

Thr Thr Thr Cys Ala Gly Ala Ala Gly Thr Thr Gly Ala Thr Ala Thr
        515                 520                 525

Gly Gly Ala Cys Thr Thr Cys Ala Cys Ala Thr Thr Ala Gly Ala Cys
    530                 535                 540

Thr Thr Cys Thr Ala Cys Ala Thr Gly Cys Gly Thr Cys Ala Ala Ala
545                 550                 555                 560

Cys Gly Thr Gly Gly Cys Ala Ala Gly Ala Cys Cys Cys Thr Cys Gly
                565                 570                 575

Ala Cys Thr Ala Gly Cys Cys Thr Thr Cys Gly Gly Ala Ala Gly Thr
            580                 585                 590

Cys Thr Thr Gly Ala Thr Thr Thr Gly Gly Gly Ala Cys Thr Thr Thr
        595                 600                 605

Cys Cys Ala Ala Ala Gly Ala Ala Ala Thr Cys Gly Ala Cys Thr Cys
    610                 615                 620

Ala Cys Thr Thr Ala Cys Cys Gly Thr Cys Gly Gly Ala Gly Thr Ala
625                 630                 635                 640

Gly Ala Cys Thr Ala Cys Cys Thr Gly Gly Ala Thr Ala Gly Ala Cys
                645                 650                 655

Thr Gly Thr Gly Gly Ala Ala Ala Cys Cys Cys Gly Ala Cys Ala Cys
            660                 665                 670

Gly Thr Thr Cys Thr Thr Cys Cys Cys Ala Ala Ala Thr Gly Ala Ala
        675                 680                 685

Ala Ala Gly Ala Ala Ala Thr Cys Ala Thr Thr Cys Thr Thr Cys Cys
    690                 695                 700

Ala Cys Thr Thr Gly Gly Cys Ala Ala Cys Cys Ala Cys Ala Cys Ala
705                 710                 715                 720

Thr Ala Ala Cys Thr Cys Gly Thr Thr Cys Cys Thr Thr Cys Gly Thr
                725                 730                 735

Ala Thr Cys Gly Ala Gly Gly Gly Thr Gly Ala Thr Gly Gly Ala Ala
            740                 745                 750

Cys Gly Gly Thr Thr Thr Ala Thr Ala Cys Thr Ala Gly Thr Cys Ala
        755                 760                 765

Ala Ala Gly Ala Thr Thr Ala Ala Cys Ala Gly Thr Cys Ala Cys Thr
    770                 775                 780

Gly Cys Ala Ala Cys Gly Thr Gly Thr Cys Cys Ala Ala Thr Gly Gly
785                 790                 795                 800

Ala Cys Cys Thr Gly Ala Ala Gly Cys Thr Gly Thr Thr Cys Cys Cys
                805                 810                 815

Ala Ala Thr Gly Gly Ala Cys Thr Cys Thr Cys Ala Ala Cys Ala Cys
            820                 825                 830

Thr Gly Thr Ala Ala Ala Cys Thr Gly Gly Ala Ala Ala Thr Thr Gly
        835                 840                 845

Ala Ala Ala Gly Cys Thr Ala Cys Gly Gly Cys Thr Ala Cys Ala Gly
    850                 855                 860

Thr Ala Thr Cys Cys Thr Cys Gly Ala Cys Ala Thr Thr Ala Thr Gly
865                 870                 875                 880

Thr Ala Cys Gly Thr Gly Thr Cys Gly Cys Ala Cys Gly Ala Gly Ala
                885                 890                 895

Ala Gly Ala Ala Gly Thr Cys Cys Gly Thr Gly Thr Cys Cys Ala Cys
            900                 905                 910
```

-continued

Cys Gly Ala Gly Thr Cys Thr Thr Ala Thr Gly Ala Gly Thr Thr Gly
            915                 920                 925

Cys Cys Gly Cys Ala Gly Thr Thr Gly Thr Ala Cys Thr Thr Cys
        930                 935                 940

Ala Gly Thr Cys Thr Ala Thr Cys Ala Ala Gly Gly Thr Cys Gly Thr
945                 950                 955                 960

Cys Ala Ala Thr Cys Ala Thr Ala Cys Gly Cys Ala Ala Ala Gly
            965                 970                 975

Cys Thr Thr Ala Gly Thr Thr Cys Ala Gly Gly Ala Gly Ala Ala Thr
            980                 985                 990

Ala Thr Thr Cys Cys Cys Gly Cys Cys Thr Thr Thr Gly Cys Thr Gly
            995                 1000                1005

Gly Thr Thr Cys Thr Thr Cys Cys Thr Ala Thr Cys Ala Ala Gly
        1010                1015                1020

Cys Gly Thr Ala Ala Cys Ala Thr Cys Gly Gly Cys Thr Thr Cys Thr
1025                1030                1035                1040

Ala Cys Ala Thr Cys Ala Thr Cys Cys Ala Ala Ala Thr Ala Thr Ala
                1045                1050                1055

Thr Cys Thr Ala Cys Cys Ala Cys Thr Gly Thr Cys Cys Thr Gly
1060 1065 1070

Ala Thr Thr Gly Thr Cys Gly Thr Cys Ala Thr Cys Thr Cys Ala Thr
1075 1080 1085

Gly Gly Gly Thr Ala Thr Cys Thr Thr Thr Thr Thr Gly Gly Thr Thr
1090 1095 1100

Gly Ala Gly Cys Cys Gly Cys Gly Ala Thr Gly Cys Gly Ala Cys Ala
1105 1110 1115 1120

Cys Cys Gly Gly Cys Ala Ala Gly Ala Gly Thr Thr Gly Cys Thr Cys
1125 1130 1135

Thr Cys Gly Gly Ala Gly Thr Cys Ala Cys Cys Ala Cys Thr Gly Thr
1140 1145 1150

Gly Cys Thr Cys Ala Cys Ala Ala Thr Gly Ala Cys Thr Ala Cys Thr
1155 1160 1165

Thr Thr Gly Ala Thr Gly Ala Cys Cys Ala Thr Gly Ala Cys Thr Ala
1170 1175 1180

Ala Thr Ala Gly Thr Thr Cys Ala Ala Thr Gly Cys Cys Ala Ala Ala
1185 1190 1195 1200

Ala Gly Thr Gly Thr Cys Ala Thr Ala Thr Gly Thr Gly Ala Ala Ala
1205 1210 1215

Ala Gly Thr Ala Thr Cys Gly Ala Thr Ala Thr Ala Thr Thr Thr Cys
1220 1225 1230

Thr Ala Gly Gly Thr Gly Thr Cys Thr Gly Cys Thr Thr Cys Ala Thr
1235 1240 1245

Gly Ala Thr Gly Gly Thr Ala Thr Thr Cys Thr Gly Thr Thr Cys Ala
1250 1255 1260

Cys Thr Thr Cys Thr Ala Gly Ala Ala Thr Ala Cys Gly Cys Cys Gly
1265 1270 1275 1280

Cys Cys Gly Thr Cys Gly Gly Ala Thr Ala Cys Ala Thr Cys Ala Gly
1285 1290 1295

Cys Ala Ala Ala Cys Gly Gly Ala Thr Gly Ala Ala Gly Cys Thr Thr
1300 1305 1310

Gly Thr Cys Cys Gly Ala Gly Cys Cys Ala Gly Ala Ala Ala Ala Gly
1315 1320 1325

Ala Ala Thr Cys Thr Cys Gly Ala Ala Thr Gly Cys Thr Gly Ala Cys

-continued

```
                1330                1335                1340
Cys Cys Cys Thr Thr Ala Cys Cys Ala Cys Ala Thr Cys Thr Thr
1345                1350                1355                1360
Gly Ala Gly Thr Cys Thr Cys Thr Thr Cys Cys Thr Cys Cys Ala Ala
                1365                1370                1375
Ala Ala Cys Gly Thr Ala Cys Thr Cys Thr Ala Thr Cys Cys Gly Thr
            1380                1385                1390
Thr Cys Cys Cys Thr Cys Gly Thr Ala Thr Thr Cys Ala Ala Cys
        1395                1400                1405
Ala Ala Cys Ala Cys Cys Ala Cys Gly Thr Ala Cys Cys Gly Cys Cys
    1410                1415                1420
Cys Gly Thr Thr Thr Thr Ala Cys Thr Cys Gly Thr Cys Cys Ala Cys
1425                1430                1435                1440
Cys Gly Ala Thr Cys Ala Ala Ala Cys Gly Thr Cys Cys Ala Ala Cys
                1445                1450                1455
Cys Thr Gly Thr Ala Cys Ala Thr Thr Cys Cys Gly Gly Ala Gly Thr
            1460                1465                1470
Cys Gly Cys Ala Gly Cys Gly Cys Ala Cys Gly Ala Cys Gly Ala Thr
        1475                1480                1485
Thr Thr Thr Cys Thr Cys Ala Ala Ala Thr Gly Ala Gly Gly Ala Thr
    1490                1495                1500
Gly Cys Ala Gly Thr Gly Cys Cys Gly Ala Ala Thr Gly Ala Ala Cys
1505                1510                1515                1520
Thr Ala Ala Cys Thr Cys Cys Ala Ala Thr Gly Cys Thr Cys Gly Gly
                1525                1530                1535
Ala Cys Gly Gly Ala Gly Thr Ala Ala Cys Thr Cys Ala Cys Ala Ala
            1540                1545                1550
Gly Cys Ala Thr Cys Cys Gly Thr Ala Thr Thr Cys Thr Gly Thr
        1555                1560                1565
Ala Thr Cys Ala Gly Ala Cys Gly Gly Cys Thr Gly Thr Ala Ala Thr
    1570                1575                1580
Ala Thr Cys Cys Gly Ala Thr Gly Ala Cys Gly Ala Gly Thr Thr Cys
1585                1590                1595                1600
Gly Gly Ala Ala Gly Ala Thr Thr Cys Thr Gly Gly Cys Gly Thr Thr
                1605                1610                1615
Gly Gly Cys Thr Cys Cys Gly Ala Cys Cys Ala Thr Cys Cys Ala Ala
            1620                1625                1630
Cys Ala Thr Thr Gly Ala Cys Ala Ala Gly Thr Ala Cys Thr Cys Ala
        1635                1640                1645
Cys Gly Cys Thr Cys Ala Cys Thr Gly Thr Thr Cys Cys Cys Ala Thr
    1650                1655                1660
Cys Thr Ala Thr Thr Thr Thr Gly Thr Gly Cys Thr Cys Thr Thr
1665                1670                1675                1680
Cys Ala Ala Cys Gly Thr Cys Gly Gly Cys Thr Ala Cys Thr Gly Gly
                1685                1690                1695
Gly Cys Cys Thr Ala Cys Thr Cys Ala Thr Cys Cys Gly Gly Cys
            1700                1705                1710
Ala Gly Ala Gly Cys Cys Ala Gly Ala Thr Thr Cys Ala Gly Gly Ala
        1715                1720                1725
Ala Gly Ala Gly Cys Ala Ala Cys Gly Gly Ala Ala Cys Ala Gly Thr
    1730                1735                1740
Cys Ala Ala Ala Thr Thr Cys Thr Cys Thr Ala Ala Thr Thr Thr Cys
1745                1750                1755                1760
```

-continued

```
Thr Gly Ala Thr Cys Ala Cys Ala Cys Cys Ala Cys Thr Cys Cys Thr
                1765                1770                1775

Cys Ala Thr Cys Thr Cys Ala Thr Thr Cys Thr Ala Thr Thr Gly Thr
            1780                1785                1790

Ala Gly Cys Cys Thr Thr Thr Thr Thr Thr Thr Thr Thr Cys Gly Ala
        1795                1800                1805

Ala Thr Cys Ala Thr Thr Thr Cys Thr Gly Ala Ala Thr Ala Thr Cys
    1810                1815                1820
Thr Cys Thr Thr Ala Thr Cys Thr Thr Cys Thr Cys Ala Ala Ala Gly
1825                1830                1835                1840
Ala Thr Gly Gly Cys Ala Thr Cys Gly Cys Cys Thr Ala Ala Cys Cys
                1845                1850                1855

Ala Cys Cys Cys Cys Cys Cys Ala Cys Thr Thr Ala Gly Cys Ala Cys
            1860                1865                1870

Ala Cys Ala Ala Ala Ala Ala Thr Gly Cys Thr Cys Thr Cys Thr Thr
        1875                1880                1885

Cys Thr Ala Gly Ala Ala Thr Thr Thr Gly Thr Thr Gly Ala Gly Ala
    1890                1895                1900
Ala Cys Gly Gly Ala Gly Ala Cys Ala Cys Cys Gly Ala
1905                1910                1915
```

<210> SEQ ID NO 6
<211> LENGTH: 1917
<212> TYPE: DNA
<213> ORGANISM: Caenorhabditis elegans

<400> SEQUENCE: 6

```
gatccccagc gcctccccgt tacctctgtg ttctccgtgt tggctcaact tgtgcgtgtt      60
ttacatctct ctgtctctct ctcatcatca tcatcttatt ctgtgctccc gctaaccgat     120
tggctcattc tcttcggctc ttgtcactaa cgaatcgctt ttcacacaga gtgatatagg     180
agaaaaacct ccccaacatt ggctcacacc cggattatga tcttctgctg ctcctgctgc     240
tccttctgct gtagttgaga cgaagaagaa gaagaagctc cattctcgag aaatggctcg     300
tccattcaca cttatcgtac tcctctccgc acatctgtgt ctacatgtgg ttgtgacaca     360
ggatgaggac tcacatatca acactcaact cctctcatca gttctcgata gactcacgaa     420
tcgcactact tatgataaaa gattacggcc caggtatggt gaaaagccag tcgacgttgg     480
aattacgata cacgtttctt caatctctgc agtttcagaa gttgatatgg acttcacatt     540
agacttctac atgcgtcaaa cgtggcaaga ccctcgacta gccttcggaa gtcttgattt     600
gggactttcc aaagaaatcg actcacttac cgtcggagta gactacctgg atagactgtg     660

gaaacccgac acgttcttcc caaatgaaaa gaaatcattc ttccacttgg caaccacaca     720
taactcgttc cttcgtatcg agggtgatgg aacggtttat actagtcaaa gattaacagt     780
cactgcaacg tgtccaatgg acctgaagct gttcccaatg gactctcaac actgtaaact     840
ggaaattgaa agctacggct acagtatcct cgacattatg tacgtgtcgc acgagaagaa     900
gtccgtgtcc accgagtctt atgagttgcc gcagtttgta cttcagtcta tcaaggtcgt     960
caatcatacg caaaagctta gttcaggaga atattcccgc ctttgctggt tcttcctatt    1020
caagcgtaac atcggcttct acatcatcca aatatatcta ccatctgtcc tgattgtcgt    1080
catctcatgg gtatcttttt ggttgagccg cgatgcgaca ccggcaagag ttgctctcgg    1140
agtcaccact gtgctcacaa tgactacttt gatgaccatg actaatagtt caatgccaaa    1200
```

```
agtgtcatat gtgaaaagta tcgatatatt tctaggtgtc tgcttcatga tggtattctg   1260
ttcacttcta gaatacgccg ccgtcggata catcagcaaa cggatgaagc ttgtccgagc   1320
cagaaaagaa tctcgaatgc tgacccctt accacatctt gagtctcttc ctccaaaacg   1380
tactctatcc gttccctcgt atttcaacaa caccacgtac cgcccgtttt actcgtccac   1440
cgatcaaacg tccaacctgt acattccgga gtcgcagcgc acgacgattt tctcaaatga   1500
ggatgcagtg ccgaatgaac taactccaat gctcggacgg agtaactcac aagcatccgt   1560
atttctgtat cagacggctg taatatccga tgacgagttc ggaagattct ggcgttggct   1620
ccgaccatcc aacattgaca agtactcacg ctcactgttc ccatctattt ttgtgctctt   1680
caacgtcggc tactgggcct acttcatccg gcagagccag attcaggaag agcaacggaa   1740
cagtcaaatt ctctaatttc tgatcacacc actcctcatc tcattctatt gtagccttt    1800 ttttcgaat catttctgaa tatctcttat cttctcaaag atggcatcgc ctaaccaccc    1860
cccacttagc acacaaaaat gctctcttct agaatttgtt gagaacggag acaccga      1917
```

<210> SEQ ID NO 7
<211> LENGTH: 2508
<212> TYPE: PRT
<213> ORGANISM: Caenorhabditis elegans

<400> SEQUENCE: 7

```
Ala Ala Gly Thr Thr Gly Ala Gly Ala Thr Gly Ala Thr Ala
  1               5                  10                  15

Thr Ala Gly Gly Ala Gly Ala Ala Ala Ala Cys Cys Thr Cys Cys
                 20                  25                  30

Cys Cys Ala Ala Cys Ala Thr Thr Gly Gly Cys Thr Cys Ala Cys Ala
         35                  40                  45

Cys Cys Cys Gly Gly Ala Thr Thr Ala Thr Gly Ala Thr Cys Thr Thr
     50                  55                  60

Cys Thr Gly Cys Thr Gly Cys Thr Cys Cys Gly Cys Thr Gly Cys
 65                  70                  75                  80

Thr Cys Cys Thr Thr Cys Thr Gly Cys Thr Gly Thr Ala Gly Thr Thr
                 85                  90                  95

Gly Ala Gly Ala Cys Gly Ala Ala Gly Ala Ala Gly Ala Ala Gly Ala
                100                 105                 110

Ala Gly Ala Ala Gly Cys Thr Cys Cys Ala Thr Thr Cys Thr Cys Gly
        115                 120                 125

Ala Gly Ala Ala Ala Thr Gly Gly Cys Thr Cys Gly Thr Cys Cys Ala
    130                 135                 140

Thr Thr Cys Ala Cys Ala Cys Thr Thr Ala Thr Cys Gly Thr Ala Cys
145                 150                 155                 160

Thr Cys Cys Thr Cys Thr Cys Cys Gly Cys Ala Cys Thr Cys Thr
                165                 170                 175

Gly Thr Gly Thr Cys Thr Ala Cys Ala Thr Gly Thr Gly Gly Thr Thr
                180                 185                 190

Gly Thr Gly Ala Cys Ala Cys Ala Gly Gly Ala Thr Gly Ala Gly Gly
        195                 200                 205

Ala Cys Thr Cys Ala Cys Ala Thr Ala Thr Cys Ala Ala Cys Ala Cys
    210                 215                 220

Thr Cys Ala Ala Cys Thr Cys Cys Cys Thr Cys Ala Thr Cys Ala
225                 230                 235                 240

Gly Thr Thr Cys Thr Cys Gly Ala Thr Ala Gly Ala Cys Thr Cys Ala
                245                 250                 255
```

-continued

```
Cys Gly Ala Ala Thr Cys Gly Cys Ala Cys Thr Ala Cys Thr Thr Ala
            260                 265                 270

Thr Gly Ala Thr Ala Ala Ala Ala Gly Ala Thr Thr Ala Cys Gly Gly
        275                 280                 285
Cys Cys Cys Ala Gly Gly Thr Ala Thr Gly Gly Thr Gly Ala Ala Ala
    290                 295                 300

Ala Gly Cys Cys Ala Gly Thr Cys Gly Ala Cys Gly Thr Thr Gly Gly
305                 310                 315                 320
Ala Ala Thr Thr Ala Cys Gly Ala Thr Ala Cys Ala Cys Gly Thr Thr
                325                 330                 335
Thr Cys Thr Thr Cys Ala Ala Thr Cys Thr Cys Thr Gly Cys Ala Gly
            340                 345                 350

Thr Thr Thr Cys Ala Gly Ala Ala Gly Thr Thr Gly Ala Thr Ala Thr
        355                 360                 365

Gly Gly Ala Cys Thr Thr Cys Ala Cys Ala Thr Thr Ala Gly Ala Cys
    370                 375                 380

Thr Thr Cys Thr Ala Cys Ala Thr Gly Cys Gly Thr Cys Ala Ala Ala
385                 390                 395                 400

Cys Gly Thr Gly Gly Cys Ala Ala Gly Ala Cys Cys Cys Thr Cys Gly
                405                 410                 415
Ala Cys Thr Ala Gly Cys Cys Thr Thr Cys Gly Gly Ala Ala Gly Thr
            420                 425                 430

Cys Thr Thr Gly Ala Thr Thr Thr Gly Gly Gly Ala Cys Thr Thr Thr
        435                 440                 445

Cys Cys Ala Ala Ala Gly Ala Ala Ala Thr Cys Gly Ala Cys Thr Cys
    450                 455                 460

Ala Cys Thr Thr Ala Cys Cys Gly Thr Cys Gly Gly Ala Gly Thr Ala
465                 470                 475                 480
Gly Ala Cys Thr Ala Cys Cys Thr Gly Gly Ala Thr Ala Gly Ala Cys
                485                 490                 495
Thr Gly Thr Gly Gly Ala Ala Ala Cys Cys Cys Gly Ala Cys Ala Cys
            500                 505                 510

Gly Thr Thr Cys Thr Thr Cys Cys Cys Ala Ala Ala Thr Gly Ala Ala
        515                 520                 525
Ala Ala Gly Ala Ala Ala Thr Cys Ala Thr Thr Cys Thr Thr Cys Cys
    530                 535                 540

Ala Cys Thr Thr Gly Gly Cys Ala Ala Cys Cys Ala Cys Ala Cys Ala
545                 550                 555                 560

Thr Ala Ala Cys Thr Cys Gly Thr Thr Cys Cys Thr Thr Cys Gly Thr
                565                 570                 575

Ala Thr Cys Gly Ala Gly Gly Gly Thr Gly Ala Thr Gly Gly Ala Ala
            580                 585                 590

Cys Gly Gly Thr Thr Thr Ala Thr Ala Cys Thr Ala Gly Thr Cys Ala
        595                 600                 605

Ala Ala Gly Ala Thr Thr Ala Ala Cys Ala Gly Thr Cys Ala Cys Thr
    610                 615                 620

Gly Cys Ala Ala Cys Gly Thr Gly Thr Cys Cys Ala Ala Thr Gly Gly
625                 630                 635                 640

Ala Cys Cys Thr Gly Ala Ala Gly Cys Thr Gly Thr Thr Cys Cys Cys
                645                 650                 655

Ala Ala Thr Gly Gly Ala Cys Thr Cys Thr Cys Ala Ala Cys Ala Cys
            660                 665                 670
```

-continued

```
Thr Gly Thr Ala Ala Ala Cys Thr Gly Gly Ala Ala Thr Thr Gly
        675                 680                 685
Ala Ala Ala Gly Cys Thr Ala Cys Gly Gly Gly Thr Ala Cys Gly Ala
690                 695                 700
Gly Ala Cys Gly Ala Ala Ala Gly Ala Thr Ala Thr Cys Gly Ala Cys
705                 710                 715                 720
Thr Ala Cys Thr Ala Thr Gly Gly Gly Gly Ala Ala Gly Ala
                    725                 730                 735
Ala Gly Cys Gly Gly Ala Cys Thr Gly Ala Thr Thr Gly Gly Ala
                740                 745                 750
Gly Ala Thr Ala Ala Cys Gly Gly Cys Thr Gly Thr Cys Ala Ala Gly
                755                 760                 765
Thr Thr Thr Gly Ala Thr Ala Cys Cys Thr Thr Cys Cys Ala Gly Thr
770                 775                 780
Thr Gly Cys Cys Gly Cys Ala Gly Thr Thr Cys Ala Gly Cys Cys
785                 790                 795                 800
Ala Ala Cys Gly Cys Thr Gly Thr Ala Thr Thr Thr Gly Thr Gly
                805                 810                 815
Ala Ala Thr Ala Cys Ala Ala Cys Thr Ala Ala Ala Gly Cys Cys Gly
                820                 825                 830
Ala Gly Ala Cys Cys Thr Cys Ala Thr Cys Ala Gly Gly Ala Ala Ala
                835                 840                 845
Ala Thr Ala Cys Gly Thr Ala Cys Gly Cys Cys Thr Gly Gly Cys Gly
                850                 855                 860
Cys Thr Gly Gly Ala Ala Gly Thr Ala Ala Thr Ala Thr Thr Gly Gly
865                 870                 875                 880
Thr Thr Cys Gly Ala Ala Ala Thr Ala Thr Gly Gly Gly Cys Thr Thr
                885                 890                 895
Cys Thr Ala Cys Ala Cys Thr Ala Thr Gly Ala Ala Cys Ala Thr Cys
                    900                 905                 910
Gly Thr Cys Ala Thr Cys Cys Ala Thr Cys Cys Ala Thr Cys Cys
                    915                 920                 925
Thr Gly Ala Thr Cys Gly Thr Cys Ala Cys Cys Ala Thr Ala Thr Cys
    930                 935                 940
Thr Thr Gly Gly Gly Thr Ala Thr Cys Ala Thr Thr Thr Thr Gly Gly
945                 950                 955                 960
Thr Thr Gly Ala Ala Thr Cys Gly Ala Gly Ala Ala Gly Cys Thr Thr
                965                 970                 975
Cys Gly Cys Cys Gly Gly Cys Thr Cys Gly Ala Gly Thr Thr Gly Gly
                980                 985                 990
Ala Thr Thr Gly Gly Gly Thr Gly Thr Gly Ala Cys Thr Ala Cys Thr
                995                 1000                1005
Gly Thr Gly Cys Thr Cys Ala Cys Ala Ala Thr Gly Ala Cys Ala Ala
    1010                1015                1020
Cys Thr Cys Thr Gly Ala Thr Cys Ala Cys Thr Ala Cys Ala Ala Cys
1025                1030                1035                1040
Cys Ala Ala Thr Ala Ala Thr Thr Cys Gly Ala Thr Gly Cys Cys Ala
                1045                1050                1055
Ala Ala Ala Gly Thr Gly Thr Cys Thr Thr Ala Thr Gly Thr Cys Ala
                1060                1065                1070
Ala Gly Gly Gly Thr Cys Thr Gly Gly Ala Thr Gly Thr Gly Thr Thr
                1075                1080                1085
Thr Cys Thr Thr Ala Ala Thr Thr Thr Thr Thr Gly Thr Thr Thr Cys
```

-continued

```
    1090                1095                1100

Gly Thr Ala Ala Thr Gly Gly Thr Ala Thr Thr Cys Gly Cys Cys Thr
1105                1110                1115                1120

Cys Gly Thr Thr Gly Cys Thr Cys Gly Ala Gly Thr Ala Cys Gly Cys
                1125                1130                1135

Cys Ala Thr Ala Gly Thr Ala Thr Cys Cys Thr Ala Cys Ala Thr Gly
            1140                1145                1150

Ala Ala Thr Ala Ala Ala Cys Gly Ala Cys Thr Gly Gly Thr Cys Cys
        1155                1160                1165

Thr Cys Cys Gly Ala Cys Gly Gly Gly Ala Ala Ala Ala Ala Cys Gly
    1170                1175                1180

Ala Ala Gly Ala Ala Ala Ala Gly Cys Cys Gly Cys Cys Gly Ala Ala
1185                1190                1195                1200

Cys Ala Ala Cys Ala Gly Cys Ala Gly Cys Gly Ala Ala Ala Cys Gly
                1205                1210                1215

Ala Gly Ala Thr Gly Cys Cys Ala Ala Thr Gly Thr Thr Cys Ala Ala
            1220                1225                1230

Cys Gly Cys Gly Ala Gly Cys Cys Cys Gly Ala Ala Gly Gly Cys Cys
        1235                1240                1245

Gly Cys Cys Ala Ala Thr Ala Ala Thr Ala Ala Thr Ala Ala Thr Cys
    1250                1255                1260

Cys Ala Thr Thr Gly Ala Thr Gly Gly Ala Gly Ala Thr Cys Cys Cys
1265                1270                1275                1280

Ala Gly Ala Ala Ala Ala Thr Thr Gly Thr Gly Ala Thr Thr Gly Cys
                1285                1290                1295

Cys Gly Gly Ala Cys Gly Ala Thr Thr Cys Cys Ala Ala Thr Gly Ala
            1300                1305                1310

Thr Gly Cys Ala Ala Cys Ala Thr Cys Cys Ala Cys Gly Thr Cys Thr
        1315                1320                1325

Thr Gly Thr Cys Ala Cys Ala Gly Ala Cys Gly Gly Cys Gly Cys Ala
    1330                1335                1340

Cys Ala Thr Ala Cys Gly Cys Thr Ala Thr Gly Gly Cys Cys Gly Gly
1345                1350                1355                1360

Cys Thr Cys Cys Ala Thr Thr Cys Gly Cys Gly Cys Gly Gly Cys Cys
                1365                1370                1375

Gly Ala Ala Ala Ala Ala Gly Gly Cys Thr Thr Cys Cys Ala Ala Gly
            1380                1385                1390

Ala Cys Ala Thr Gly Cys Thr Gly Cys Cys Ala Ala Cys Gly Ala Thr
        1395                1400                1405

Gly Gly Ala Cys Gly Cys Cys Thr Gly Cys Ala Ala Ala Ala Ala Thr
    1410                1415                1420

Cys Gly Ala Thr Ala Ala Gly Cys Thr Thr Ala Gly Cys Cys Gly Ala
1425                1430                1435                1440

Thr Ala Cys Gly Gly Thr Thr Thr Cys Cys Cys Ala Thr Thr Gly Thr
                1445                1450                1455

Cys Thr Thr Thr Cys Thr Cys Thr Ala Thr Cys Thr Thr Cys Ala Ala
            1460                1465                1470

Thr Ala Thr Ala Gly Thr Cys Thr Ala Cys Thr Gly Gly Thr Thr Gly
        1475                1480                1485

Thr Ala Thr Ala Thr Gly Ala Ala Ala Thr Ala Thr Cys Thr Ala Ala
    1490                1495                1500

Gly Cys Thr Thr Ala Ala Ala Cys Thr Cys Gly Thr Cys Gly Gly Ala
1505                1510                1515                1520
```

-continued

Cys Ala Ala Gly Ala Thr Cys Ala Gly Gly Ala Gly Ala Ala Cys
                1525                1530                1535

Gly Ala Cys Ala Ala Gly Thr Gly Gly Cys Ala Gly Cys Ala Gly Ala
            1540                1545                1550

Thr Cys Cys Ala Cys Thr Gly Ala Thr Gly Cys Gly Thr Ala Thr Thr
            1555                1560                1565

Cys Gly Ala Cys Gly Gly Cys Cys Gly Ala Ala Ala Thr Cys Gly Ala
            1570                1575                1580

Gly Thr Ala Cys Ala Ala Ala Thr Gly Gly Thr Gly Thr Ala Cys Gly
1585                1590                1595                1600

Thr Cys Gly Ala Ala Gly Gly Ala Gly Cys Cys Gly Ala Ala Thr Thr
            1605                1610                1615

Gly Thr Thr Cys Gly Ala Cys Ala Gly Cys Gly Gly Thr Cys Ala Ala
            1620                1625                1630

Gly Gly Cys Cys Gly Ala Cys Gly Cys Gly Ala Ala Cys Ala Thr Cys
            1635                1640                1645

Gly Ala Ala Cys Thr Gly Thr Cys Gly Ala Gly Thr Thr Ala Thr Ala
            1650                1655                1660

Ala Ala Thr Thr Cys Ala Cys Thr Ala Ala Ala Ala Thr Cys Thr Gly
1665                1670                1675                1680

Cys Cys Ala Ala Ala Ala Ala Cys Gly Gly Ala Cys Ala Cys Thr Thr
            1685                1690                1695

Gly Cys Cys Ala Gly Cys Ala Cys Thr Thr Cys Ala Thr Cys Gly Gly
            1700                1705                1710

Gly Gly Ala Cys Cys Thr Ala Cys Thr Cys Thr Cys Gly Thr Cys Thr
            1715                1720                1725

Ala Cys Gly Gly Gly Thr Thr Ala Gly Thr Thr Thr Cys Ala Thr Ala
            1730                1735                1740

Thr Thr Thr Gly Ala Thr Cys Gly Cys Gly Ala Cys Ala Gly Cys Gly
1745                1750                1755                1760

Gly Cys Thr Thr Cys Thr Ala Cys Thr Thr Cys Thr Thr Cys Ala
            1765                1770                1775

Ala Ala Thr Ala Thr Thr Thr Thr Cys Cys Cys Thr Gly Cys Cys
            1780                1785                1790

Ala Gly Cys Cys Thr Cys Gly Thr Cys Gly Thr Ala Gly Thr Thr Thr
            1795                1800                1805

Thr Ala Thr Cys Ala Thr Gly Gly Ala Thr Cys Thr Cys Ala Thr Thr
            1810                1815                1820

Cys Thr Gly Gly Ala Thr Cys Ala Ala Thr Cys Gly Thr Gly Ala Cys
1825                1830                1835                1840

Thr Cys Gly Gly Cys Gly Cys Cys Thr Thr Cys Gly Cys Gly Ala Ala
            1845                1850                1855

Cys Cys Cys Thr Ala Ala Thr Cys Gly Gly Thr Ala Cys Gly Ala Thr
            1860                1865                1870

Gly Ala Cys Gly Gly Thr Gly Cys Thr Cys Ala Cys Thr Gly Ala Gly
            1875                1880                1885

Ala Cys Thr Cys Ala Thr Cys Thr Thr Ala Thr Gly Ala Cys Cys Gly
            1890                1895                1900

Gly Ala Ala Cys Cys Ala Ala Thr Cys Gly Ala Cys Gly Thr Cys Thr
1905                1910                1915                1920

Thr Cys Cys Ala Cys Cys Ala Gly Thr Thr Gly Cys Cys Thr Ala Thr
            1925                1930                1935

-continued

```
Gly Thr Ala Ala Ala Ala Gly Cys Cys Gly Thr Thr Gly Ala Thr Gly
            1940                1945                1950

Thr Ala Thr Thr Cys Cys Thr Cys Gly Gly Thr Thr Thr Cys Thr Gly
        1955                1960                1965

Cys Thr Ala Thr Cys Thr Thr Cys Thr Gly Gly Thr Thr Ala Thr Ala
    1970                1975                1980

Cys Thr Gly Gly Cys Gly Thr Thr Gly Ala Thr Cys Gly Ala Gly Thr
1985                1990                1995                2000
Ala Cys Gly Cys Cys Thr Gly Thr Gly Thr Thr Gly Cys Cys Thr Ala
                2005                2010                2015

Cys Thr Cys Ala Ala Ala Ala Ala Ala Gly Ala Ala Gly Ala Ala Cys
            2020                2025                2030
Gly Ala Gly Gly Ala Thr Cys Gly Thr Cys Gly Gly Ala Gly Ala Ala
        2035                2040                2045

Gly Ala Gly Ala Gly Ala Ala Gly Ala Ala Gly Ala Cys Gly Gly Ala
    2050                2055                2060

Gly Cys Ala Thr Ala Ala Ala Cys Cys Thr Gly Cys Thr Cys Cys Gly
2065                2070                2075                2080
Cys Cys Gly Ala Cys Ala Cys Cys Thr Gly Ala Thr Ala Thr Thr Cys
                2085                2090                2095

Thr Thr Cys Ala Cys Gly Ala Cys Gly Thr Cys Cys Gly Cys Cys Thr
            2100                2105                2110
Thr Gly Cys Cys Gly Ala Ala Thr Gly Cys Ala Cys Ala Thr Gly Cys
        2115                2120                2125

Ala Ala Cys Gly Cys Gly Gly Cys Thr Cys Cys Ala Ala Cys Cys Thr
    2130                2135                2140

Cys Gly Ala Thr Cys Ala Thr Cys Gly Cys Cys Gly Thr Cys Ala Thr
2145                2150                2155                2160

Cys Ala Ala Gly Cys Ala Gly Thr Cys Gly Ala Ala Thr Cys Gly Ala
                2165                2170                2175

Thr Thr Cys Thr Gly Thr Gly Thr Cys Ala Gly Thr Cys Ala Cys Ala
            2180                2185                2190

Gly Thr Cys Ala Cys Ala Thr Thr Gly Ala Cys Ala Thr Cys Gly Thr
        2195                2200                2205

Cys Ala Gly Cys Cys Gly Thr Gly Cys Cys Gly Cys Gly Thr Thr Thr
    2210                2215                2220

Cys Cys Thr Cys Thr Thr Gly Thr Thr Thr Thr Cys Ala Thr Cys Thr
2225                2230                2235                2240

Thr Gly Thr Thr Cys Ala Ala Cys Ala Cys Thr Cys Thr Cys Thr Thr
                2245                2250                2255

Cys Thr Gly Gly Cys Thr Gly Ala Thr Thr Cys Thr Ala Cys Thr Gly
            2260                2265                2270

Thr Ala Cys Ala Ala Ala Thr Cys Cys Ala Ala Gly Cys Gly Thr Cys
        2275                2280                2285

Thr Gly Cys Cys Gly Thr Ala Thr Ala Thr Thr Ala Gly Thr Gly Ala
    2290                2295                2300

Ala Cys Ala Cys Gly Ala Gly Gly Gly Thr Gly Ala Cys Cys Gly Thr
2305                2310                2315                2320

Thr Gly Cys Gly Ala Thr Gly Cys Thr Cys Cys Ala Gly Ala Cys Cys
                2325                2330                2335

Thr Thr Cys Ala Thr Thr Ala Ala Thr Cys Thr Cys Ala Ala Thr Cys
            2340                2345                2350

Cys Ala Ala Cys Thr Thr Cys Cys Thr Cys Ala Thr Cys Ala Thr Thr
```

-continued

```
                    2355                2360                2365
Thr Thr Cys Cys Ala Thr Thr Cys Gly Ala Ala Thr Ala Thr Cys
    2370                2375                2380
Thr Cys Thr Thr Thr Thr Thr Cys Thr Thr Gly Cys Ala Cys Ala Gly
2385                2390                2395                2400
Ala Ala Gly Cys Cys Thr Thr Thr Thr Thr Cys Gly Thr Thr Thr
            2405                2410                2415
Thr Thr Thr Thr Thr Thr Ala Thr Gly Ala Thr Thr Thr Ala Thr
                2420                2425                2430
Thr Thr Thr Thr Ala Cys Gly Gly Ala Thr Thr Thr Thr Ala Gly
        2435                2440                2445
Ala Thr Ala Ala Thr Gly Cys Ala Cys Ala Gly Ala Thr Gly Cys Cys
2450                2455                2460
Thr Cys Ala Thr Thr Gly Cys Thr Cys Ala Ala Ala Thr Ala Ala Ala
2465                2470                2475                2480
Thr Thr Thr Ala Thr Thr Thr Thr Ala Ala Thr Thr Ala Ala Ala
            2485                2490                2495
Ala Ala Ala Ala Ala Ala Ala Ala Ala Ala Ala Ala
        2500                2505

<210> SEQ ID NO 8
<211> LENGTH: 2508
<212> TYPE: DNA
<213> ORGANISM: Caenorhabditis elegans

<400> SEQUENCE: 8
aagtttgaga gtgatatagg agaaaaacct ccccaacatt ggctcacacc cggattatga    60
tcttctgctg ctcctgctgc tccttctgct gtagttgaga cgaagaagaa gaagaagctc   120
cattctcgag aaatggctcg tccattcaca cttatcgtac tcctctccgc acatctgtgt   180
ctacatgtgg ttgtgacaca ggatgaggac tcacatatca acactcaact cctctcatca   240
gttctcgata gactcacgaa tcgcactact tatgataaaa gattacggcc caggtatggt   300
gaaaagccag tcgacgttgg aattacgata cacgtttctt caatctctgc agtttcagaa   360
gttgatatgg acttcacatt agacttctac atgcgtcaaa cgtggcaaga ccctcgacta   420
gccttcggaa gtcttgattt gggactttcc aaagaaatcg actcacttac cgtcggagta   480
gactacctgg atagactgtg aaacccgac acgttcttcc caaatgaaaa gaaatcattc   540
ttccacttgg caaccacaca taactcgttc cttcgtatcg agggtgatgg aacggtttat   600
actagtcaaa gattaacagt cactgcaacg tgtccaatgg acctgaagct gttcccaatg   660
gactctcaac actgtaaact ggaaattgaa agctacgggt acgagacgaa agatatcgac   720
tactattggg ggaagaagcg gactgatttg gagataacgg ctgtcaagtt tgataccttc   780
cagttgccgc agtttcagcc aacgctgtat tttgtgaata caactaaagc cgagacctca   840
tcaggaaaat acgtacgcct ggcgctggaa gtaatattgg ttcgaaatat gggcttctac   900
actatgaaca tcgtcatccc atccatcctg atcgtcacca tatcttgggt atcattttgg   960
ttgaatcgag aagcttcgcc ggctcgagtt ggattgggtg tgactactgt gctcacaatg  1020
acaactctga tcactacaac caataattcg atgccaaaag tgtcttatgt caagggtctg  1080
gatgtgtttc ttaatttttg tttcgtaatg gtattcgcct cgttgctcga gtacgccata  1140
gtatcctaca tgaataaacg actggtcctc cgacgggaaa acgaagaaa agccgccgaa  1200 caacagcagc gaaacgagat gccaatgttc aacgcgagcc cgaaggccgc caataataat  1260
```

```
aatccattga tggagatccc agaaaattgt gattgccgga cgattccaat gatgcaacat   1320
ccacgtcttg tcacagacgg cgcacatacg ctatggccgg ctccattcgc gcggccgaaa   1380
aaggcttcca agacatgctg ccaacgatgg acgcctgcaa aaatcgataa gcttagccga   1440
tacggtttcc cattgtcttt ctctatcttc aatatagtct actggttgta tatgaaatat   1500
ctaagcttaa actcgtcgga caagatccag gagaacgaca agtggcagca gatccactga   1560
tgcgtattcg acggccgaaa tcgagtacaa atggtgtacg tcgaaggagc cgaattgttc   1620
gacagcggtc aaggccgacg cgaacatcga actgtcgagt tataaattca ctaaaatctg   1680
ccaaaaacgg acacttgcca gcacttcatc ggggacctac tctcgtctac gggttagttt   1740
catatttgat cgcgacagcg gcttctactt tcttcaaata tttttccctg ccagcctcgt   1800
cgtagtttta tcatggatct cattctggat caatcgtgac tcggcgcctt cgcgaaccct   1860
aatcggtacg atgacggtgc tcactgagac tcatcttatg accggaacca atcgacgtct   1920
tccaccagtt gccatgtaa aagccgttga tgtattcctc ggtttctgct atcttctggt   1980
tatactggcg ttgatcgagt acgcctgtgt tgcctactca aaaagaaga acgaggatcg   2040 tcggagaaga gagaagaaga cggagcataa acctgctccg ccgacacctg atattcttca   2100
cgacgtccgc cttgccgaat gcacatgcaa cgcggctcca acctcgatca tcgccgtcat   2160
caagcagtcg aatcgattct gtgtcagtca cagtcacatt gacatcgtca gccgtgccgc   2220
gtttcctctt gttttcatct tgttcaacac tctcttctgg ctgattctac tgtacaaatc   2280
caagcgtctg ccgtatatta gtgaacacga gggtgaccgt tgcgatgctc cagaccttca   2340
ttaatctcaa tccaacttcc tcatcatttt ccatttcgaa tatctctttt tcttgcacag   2400 aagcctttt tcgttttttt ttattgattt attttacgg attttagat aatgcacaga   2460 tgcctcattg ctcaaataaa tttattttaa ttaaaaaaaa aaaaaaaa   2508
```

<210> SEQ ID NO 9  
<211> LENGTH: 2601  
<212> TYPE: PRT  
<213> ORGANISM: Caenorhabditis elegans

<400> SEQUENCE: 9

```
Ala Ala Gly Thr Thr Gly Ala Gly Ala Gly Thr Gly Ala Thr Ala
 1               5                  10                  15

Thr Ala Gly Gly Ala Gly Ala Ala Ala Ala Cys Cys Thr Cys Cys
                20                  25                  30

Cys Cys Ala Ala Cys Ala Thr Thr Gly Gly Cys Thr Cys Ala Cys Ala
            35                  40                  45

Cys Cys Cys Gly Gly Ala Thr Thr Ala Thr Gly Ala Thr Cys Thr Thr
        50                  55                  60

Cys Thr Gly Cys Thr Gly Cys Thr Cys Cys Thr Gly Cys Thr Gly Cys
 65                  70                  75                  80

Thr Cys Cys Thr Thr Cys Thr Gly Cys Thr Gly Thr Ala Gly Thr Thr
                85                  90                  95

Gly Ala Gly Ala Cys Gly Ala Ala Gly Ala Ala Gly Ala Ala Gly Ala
                100                 105                 110

Ala Gly Ala Ala Gly Cys Thr Cys Cys Ala Thr Cys Thr Cys Gly
            115                 120                 125

Ala Gly Ala Ala Ala Thr Gly Gly Cys Thr Cys Gly Thr Cys Cys Ala
        130                 135                 140

Thr Thr Cys Ala Cys Ala Cys Thr Thr Ala Thr Cys Gly Thr Ala Cys
145                 150                 155                 160
```

-continued

```
Thr Cys Cys Thr Cys Thr Cys Cys Gly Cys Ala Cys Ala Thr Cys Thr
                165                 170                 175
Gly Thr Gly Thr Cys Thr Ala Cys Ala Thr Gly Thr Gly Gly Thr Thr
            180                 185                 190
Gly Thr Gly Ala Cys Ala Cys Ala Gly Gly Ala Thr Gly Ala Gly Gly
        195                 200                 205
Ala Cys Thr Cys Ala Cys Ala Thr Ala Thr Cys Ala Ala Cys Ala Cys
    210                 215                 220
Thr Cys Ala Ala Cys Thr Cys Cys Thr Cys Thr Cys Ala Thr Cys Ala
225                 230                 235                 240
Gly Thr Thr Cys Thr Cys Gly Ala Thr Ala Gly Ala Cys Thr Cys Ala
                245                 250                 255
Cys Gly Ala Ala Thr Cys Gly Cys Ala Cys Thr Ala Cys Thr Thr Ala
            260                 265                 270

Thr Gly Ala Thr Ala Ala Ala Ala Gly Ala Thr Thr Ala Cys Gly Gly
        275                 280                 285

Cys Cys Cys Ala Gly Gly Thr Ala Thr Gly Gly Thr Gly Ala Ala Ala
    290                 295                 300
Ala Gly Cys Cys Ala Gly Thr Cys Gly Ala Cys Gly Thr Thr Gly Gly
305                 310                 315                 320
Ala Ala Thr Thr Ala Cys Gly Ala Thr Ala Cys Ala Cys Gly Thr Thr
                325                 330                 335
Thr Cys Thr Thr Cys Ala Ala Thr Cys Thr Cys Thr Gly Cys Ala Gly
            340                 345                 350

Thr Thr Thr Cys Ala Gly Ala Ala Gly Thr Thr Gly Ala Thr Ala Thr
        355                 360                 365

Gly Gly Ala Cys Thr Thr Cys Ala Cys Ala Thr Thr Ala Gly Ala Cys
    370                 375                 380

Thr Thr Cys Thr Ala Cys Ala Thr Gly Cys Gly Thr Cys Ala Ala Ala
385                 390                 395                 400

Cys Gly Thr Gly Gly Cys Ala Ala Gly Ala Cys Cys Cys Thr Cys Gly
                405                 410                 415

Ala Cys Thr Ala Gly Cys Cys Thr Thr Cys Gly Gly Ala Ala Gly Thr
            420                 425                 430

Cys Thr Thr Gly Ala Thr Thr Thr Gly Gly Gly Ala Cys Thr Thr Thr
        435                 440                 445

Cys Cys Ala Ala Ala Gly Ala Ala Ala Thr Cys Gly Ala Cys Thr Cys
    450                 455                 460

Ala Cys Thr Thr Ala Cys Cys Gly Thr Cys Gly Gly Ala Gly Thr Ala
465                 470                 475                 480

Gly Ala Cys Thr Ala Cys Cys Thr Gly Gly Ala Thr Ala Gly Ala Cys
                485                 490                 495

Thr Gly Thr Gly Gly Ala Ala Ala Cys Cys Cys Gly Ala Cys Ala Cys
            500                 505                 510

Gly Thr Thr Cys Thr Thr Cys Cys Cys Ala Ala Ala Thr Gly Ala Ala
        515                 520                 525

Ala Ala Gly Ala Ala Ala Thr Cys Ala Thr Thr Cys Thr Thr Cys Cys
    530                 535                 540

Ala Cys Thr Thr Gly Gly Cys Ala Ala Cys Cys Ala Cys Ala Cys Ala
545                 550                 555                 560

Thr Ala Ala Cys Thr Cys Gly Thr Thr Cys Cys Thr Thr Cys Gly Thr
                565                 570                 575
```

-continued

```
Ala Thr Cys Gly Ala Gly Gly Thr Gly Ala Thr Gly Gly Ala Ala
                580                 585                 590
Cys Gly Gly Thr Thr Thr Ala Thr Ala Cys Thr Ala Gly Thr Cys Ala
            595                 600                 605
Ala Ala Gly Ala Thr Thr Ala Ala Cys Ala Gly Thr Cys Ala Cys Thr
            610                 615                 620
Gly Cys Ala Ala Cys Gly Thr Gly Thr Cys Cys Ala Ala Thr Gly Gly
625                 630                 635                 640
Ala Cys Cys Thr Gly Ala Ala Gly Cys Thr Gly Thr Cys Cys Cys
            645                 650                 655
Ala Ala Thr Gly Gly Ala Cys Thr Cys Thr Cys Ala Ala Cys Ala Cys
            660                 665                 670
Thr Gly Thr Ala Ala Ala Cys Thr Gly Gly Ala Ala Ala Thr Thr Gly
            675                 680                 685
Ala Ala Ala Gly Cys Thr Ala Cys Gly Gly Gly Thr Ala Cys Gly Ala
            690                 695                 700
Gly Ala Cys Gly Ala Ala Ala Gly Ala Thr Ala Thr Cys Gly Ala Cys
705                 710                 715                 720
Thr Ala Cys Thr Ala Thr Gly Gly Gly Gly Gly Ala Ala Gly Ala
            725                 730                 735
Ala Gly Cys Gly Gly Ala Cys Thr Gly Ala Thr Thr Gly Gly Ala
            740                 745                 750
Gly Ala Thr Ala Ala Cys Gly Gly Cys Thr Gly Thr Cys Ala Ala Gly
            755                 760                 765
Thr Thr Thr Gly Ala Thr Ala Cys Cys Thr Cys Cys Ala Gly Thr
            770                 775                 780
Thr Gly Cys Cys Gly Cys Ala Gly Thr Thr Thr Cys Ala Gly Cys Cys
785                 790                 795                 800
Ala Ala Cys Gly Cys Thr Gly Thr Ala Thr Thr Thr Gly Thr Gly
            805                 810                 815
Ala Ala Thr Ala Cys Ala Ala Cys Thr Ala Ala Gly Cys Cys Gly
            820                 825                 830
Ala Gly Ala Cys Cys Thr Cys Ala Thr Cys Ala Gly Ala Ala Ala
            835                 840                 845
Ala Thr Ala Cys Gly Thr Ala Cys Gly Cys Thr Gly Gly Cys Gly
            850                 855                 860
Cys Thr Gly Gly Ala Ala Gly Thr Ala Ala Thr Ala Thr Gly Gly
865                 870                 875                 880
Thr Thr Cys Gly Ala Ala Ala Thr Ala Thr Gly Gly Gly Cys Thr Thr
            885                 890                 895
Cys Thr Ala Cys Ala Cys Thr Ala Thr Gly Ala Ala Cys Ala Thr Cys
            900                 905                 910
Gly Thr Cys Ala Thr Cys Cys Ala Thr Cys Cys Ala Thr Cys Cys
            915                 920                 925
Thr Gly Ala Thr Cys Gly Thr Cys Ala Cys Cys Ala Thr Ala Thr Cys
            930                 935                 940
Thr Thr Gly Gly Gly Thr Ala Thr Cys Ala Thr Thr Thr Gly Gly
945                 950                 955                 960
Thr Thr Gly Ala Ala Thr Cys Gly Ala Gly Ala Ala Gly Cys Thr Thr
            965                 970                 975
Cys Gly Cys Cys Gly Gly Cys Thr Cys Gly Ala Gly Thr Thr Gly Gly
            980                 985                 990
Ala Thr Thr Gly Gly Gly Thr Gly Thr Gly Ala Cys Thr Ala Cys Thr
```

-continued

```
                995                 1000                1005
Gly Thr Gly Cys Thr Cys Ala Cys Ala Ala Thr Gly Ala Cys Ala Ala
            1010                1015                1020
Cys Thr Cys Thr Gly Ala Thr Cys Ala Cys Thr Ala Cys Ala Ala Cys
1025                1030                1035                1040
Cys Ala Ala Thr Ala Ala Thr Thr Cys Gly Ala Thr Gly Cys Cys Ala
                1045                1050                1055
Ala Ala Ala Gly Thr Gly Thr Cys Thr Thr Ala Thr Gly Thr Cys Ala
            1060                1065                1070
Ala Gly Gly Gly Thr Cys Thr Gly Gly Ala Thr Gly Thr Gly Thr Thr
        1075                1080                1085
Thr Cys Thr Thr Ala Ala Thr Thr Thr Thr Gly Thr Thr Thr Cys
    1090                1095                1100
Gly Thr Ala Ala Thr Gly Gly Thr Ala Thr Thr Cys Gly Cys Cys Thr
1105                1110                1115                1120
Cys Gly Thr Thr Gly Cys Thr Cys Gly Ala Gly Thr Ala Cys Gly Cys
            1125                1130                1135
Cys Ala Thr Ala Gly Thr Ala Thr Cys Cys Thr Ala Cys Ala Thr Gly
            1140                1145                1150
Ala Ala Thr Ala Ala Ala Cys Gly Ala Cys Thr Gly Gly Thr Cys Cys
        1155                1160                1165
Thr Cys Cys Gly Ala Cys Gly Gly Ala Ala Ala Ala Cys Gly Gly
    1170                1175                1180
Ala Ala Gly Ala Ala Ala Ala Gly Cys Cys Gly Cys Cys Gly Ala Ala
1185                1190                1195                1200
Cys Ala Ala Cys Ala Gly Cys Ala Gly Cys Gly Ala Ala Ala Cys Gly
            1205                1210                1215
Ala Gly Ala Thr Gly Cys Cys Ala Ala Thr Gly Thr Thr Cys Ala Ala
        1220                1225                1230
Cys Gly Cys Gly Ala Gly Cys Cys Gly Ala Ala Gly Gly Cys Cys
    1235                1240                1245
Gly Cys Cys Ala Ala Thr Ala Ala Thr Ala Ala Thr Thr Cys Ala Thr
        1250                1255                1260
Ala Cys Gly Ala Ala Ala Thr Gly Ala Cys Ala Cys Thr Thr Ala Thr
1265                1270                1275                1280
Gly Thr Cys Gly Cys Ala Ala Ala Ala Thr Thr Cys Gly Ala Cys Gly
            1285                1290                1295
Cys Cys Thr Gly Cys Cys Ala Ala Ala Ala Gly Cys Thr Ala Thr Gly
        1300                1305                1310
Thr Ala Cys Ala Gly Gly Cys Thr Gly Ala Cys Thr Thr Gly Thr Ala
    1315                1320                1325
Cys Thr Thr Thr Gly Cys Cys Gly Gly Ala Cys Ala Cys Ala Ala Thr
    1330                1335                1340
Thr Cys Cys Thr Cys Thr Ala Thr Gly Ala Ala Thr Cys Cys Ala Thr
1345                1350                1355                1360
Thr Gly Ala Thr Gly Gly Ala Gly Ala Thr Cys Cys Cys Ala Gly Ala
            1365                1370                1375
Ala Ala Ala Thr Thr Gly Thr Gly Ala Thr Gly Cys Cys Gly Gly
        1380                1385                1390
Ala Cys Gly Ala Thr Thr Cys Cys Ala Ala Thr Gly Ala Thr Gly Cys
    1395                1400                1405
Ala Ala Cys Ala Thr Cys Cys Ala Cys Gly Thr Cys Thr Thr Gly Thr
    1410                1415                1420
```

-continued

Cys Ala Cys Ala Gly Ala Cys Gly Gly Cys Gly Cys Ala Cys Ala Thr
1425                1430                1435                1440

Ala Cys Gly Cys Thr Ala Thr Gly Gly Cys Cys Gly Gly Cys Thr Cys
                1445                1450                1455

Cys Ala Thr Thr Cys Gly Cys Gly Cys Gly Gly Cys Cys Gly Ala Ala
            1460                1465                1470

Ala Ala Ala Gly Gly Cys Thr Thr Cys Cys Ala Ala Gly Ala Cys Ala
        1475                1480                1485

Thr Gly Cys Thr Gly Cys Cys Ala Ala Cys Gly Ala Thr Gly Gly Ala
    1490                1495                1500

Cys Gly Cys Cys Thr Gly Cys Ala Ala Ala Ala Thr Cys Gly Ala
1505                1510                1515                1520

Thr Ala Ala Gly Cys Thr Thr Ala Gly Cys Cys Gly Ala Thr Ala Cys
                1525                1530                1535

Gly Gly Thr Thr Thr Cys Cys Ala Thr Thr Gly Thr Cys Thr Thr
            1540                1545                1550

Thr Cys Thr Cys Thr Ala Thr Cys Thr Thr Cys Ala Ala Thr Ala Thr
        1555                1560                1565

Ala Gly Thr Cys Thr Ala Cys Thr Gly Gly Thr Thr Gly Thr Ala Thr
    1570                1575                1580

Ala Thr Gly Ala Ala Ala Thr Ala Thr Cys Thr Ala Ala Gly Cys Thr
1585                1590                1595                1600

Thr Ala Ala Ala Cys Thr Cys Gly Thr Cys Gly Gly Ala Cys Ala Ala
                1605                1610                1615

Gly Ala Thr Cys Cys Ala Gly Gly Ala Gly Ala Ala Cys Gly Ala Cys
            1620                1625                1630

Ala Ala Gly Thr Gly Gly Cys Ala Gly Cys Ala Gly Ala Thr Cys Cys
        1635                1640                1645

Ala Cys Thr Gly Ala Thr Gly Cys Gly Thr Ala Thr Thr Cys Gly Ala
    1650                1655                1660

Cys Gly Gly Cys Gly Ala Ala Ala Thr Cys Gly Ala Gly Thr Ala
1665                1670                1675                1680

Cys Ala Ala Ala Thr Gly Gly Thr Gly Thr Ala Cys Gly Thr Cys Gly
                1685                1690                1695

Ala Ala Gly Gly Ala Gly Cys Cys Gly Ala Ala Thr Thr Gly Thr Thr
            1700                1705                1710

Cys Gly Ala Cys Ala Gly Cys Gly Gly Thr Cys Ala Ala Gly Gly Cys
        1715                1720                1725

Cys Gly Ala Cys Gly Cys Gly Ala Ala Cys Ala Thr Cys Gly Ala Ala
    1730                1735                1740

Cys Thr Gly Thr Cys Gly Ala Gly Thr Thr Ala Thr Ala Ala Ala Thr
1745                1750                1755                1760

Thr Cys Ala Cys Thr Ala Ala Ala Thr Cys Thr Gly Cys Cys Ala
                1765                1770                1775

Ala Ala Ala Ala Cys Gly Gly Ala Cys Ala Cys Thr Gly Cys Cys
            1780                1785                1790

Ala Gly Cys Ala Cys Thr Thr Cys Ala Thr Cys Gly Gly Gly Gly Ala
        1795                1800                1805

Cys Cys Thr Ala Cys Thr Cys Thr Cys Gly Thr Cys Thr Ala Cys Gly
    1810                1815                1820

Gly Gly Thr Thr Ala Gly Thr Thr Thr Cys Ala Thr Ala Thr Thr
1825                1830                1835                1840

-continued

```
Gly Ala Thr Cys Gly Cys Gly Ala Cys Ala Gly Cys Gly Gly Cys Thr
                1845                1850                1855
Thr Cys Thr Ala Cys Thr Thr Thr Cys Thr Thr Cys Ala Ala Ala Thr
            1860                1865                1870

Ala Thr Thr Thr Thr Thr Cys Cys Cys Thr Gly Cys Cys Ala Gly Cys
        1875                1880                1885

Cys Thr Cys Gly Thr Cys Gly Thr Ala Gly Thr Thr Thr Thr Ala Thr
    1890                1895                1900

Cys Ala Thr Gly Gly Ala Thr Cys Thr Cys Ala Thr Thr Cys Thr Gly
1905                1910                1915                1920
Gly Ala Thr Cys Ala Ala Thr Cys Gly Thr Gly Ala Cys Thr Cys Gly
                1925                1930                1935

Gly Cys Gly Cys Cys Thr Thr Cys Gly Cys Gly Ala Ala Cys Cys Cys
            1940                1945                1950

Thr Ala Ala Thr Cys Gly Gly Thr Ala Cys Gly Ala Thr Gly Ala Cys
        1955                1960                1965

Gly Gly Thr Gly Cys Thr Cys Ala Cys Thr Gly Ala Gly Ala Cys Thr
    1970                1975                1980

Cys Ala Thr Cys Thr Thr Ala Thr Gly Ala Cys Cys Gly Gly Ala Ala
1985                1990                1995                2000
Cys Cys Ala Ala Thr Cys Gly Ala Cys Gly Thr Cys Thr Thr Cys Cys
                2005                2010                2015
Ala Cys Cys Ala Gly Thr Thr Gly Cys Cys Thr Ala Thr Gly Thr Ala
            2020                2025                2030

Ala Ala Ala Gly Cys Cys Gly Thr Thr Gly Ala Thr Gly Thr Ala Thr
        2035                2040                2045

Thr Cys Cys Thr Cys Gly Gly Thr Thr Thr Cys Thr Gly Cys Thr Ala
    2050                2055                2060

Thr Cys Thr Thr Cys Thr Gly Gly Thr Thr Ala Thr Ala Cys Thr Gly
2065                2070                2075                2080
Gly Cys Gly Thr Thr Gly Ala Thr Cys Gly Ala Gly Thr Ala Cys Gly
                2085                2090                2095
Cys Cys Thr Gly Thr Gly Thr Thr Gly Cys Cys Thr Ala Cys Thr Cys
            2100                2105                2110

Ala Ala Ala Ala Ala Ala Gly Ala Ala Gly Ala Ala Cys Gly Ala Gly
        2115                2120                2125

Gly Ala Thr Cys Gly Thr Cys Gly Gly Ala Gly Ala Ala Gly Ala Gly
    2130                2135                2140

Ala Gly Ala Ala Gly Ala Ala Gly Ala Cys Gly Gly Ala Gly Cys Ala
2145                2150                2155                2160

Thr Ala Ala Ala Cys Cys Thr Gly Cys Thr Cys Cys Gly Cys Cys Gly
                2165                2170                2175

Ala Cys Ala Cys Cys Thr Gly Ala Thr Ala Thr Thr Cys Thr Thr Cys
            2180                2185                2190

Ala Cys Gly Ala Cys Gly Thr Cys Cys Gly Cys Cys Thr Thr Gly Cys
        2195                2200                2205

Cys Gly Ala Ala Thr Gly Cys Ala Cys Ala Thr Gly Cys Ala Ala Cys
    2210                2215                2220

Gly Cys Gly Gly Cys Thr Cys Cys Ala Ala Cys Cys Thr Cys Gly Ala
2225                2230                2235                2240

Thr Cys Ala Thr Cys Gly Cys Cys Gly Thr Cys Ala Thr Cys Ala Ala
                2245                2250                2255

Gly Cys Ala Gly Thr Cys Gly Ala Ala Thr Cys Gly Ala Thr Thr Cys
```

2260                2265                2270
Thr Gly Thr Gly Thr Cys Ala Gly Thr Cys Ala Cys Ala Gly Thr Cys
        2275                2280                2285
Ala Cys Ala Thr Thr Gly Ala Cys Ala Thr Cys Gly Thr Cys Ala Gly
        2290                2295                2300
Cys Cys Gly Thr Gly Cys Cys Gly Cys Gly Thr Thr Cys Cys Thr
2305                2310                2315                2320
Cys Thr Thr Gly Thr Thr Thr Thr Cys Ala Thr Cys Thr Thr Gly Thr
                2325                2330                2335
Thr Cys Ala Ala Cys Ala Cys Thr Cys Thr Cys Thr Cys Thr Gly
        2340                2345                2350
Gly Cys Thr Gly Ala Thr Thr Cys Thr Ala Cys Thr Gly Thr Ala Cys
        2355                2360                2365
Ala Ala Ala Thr Cys Cys Ala Ala Gly Cys Gly Thr Cys Thr Gly Cys
        2370                2375                2380
Cys Gly Thr Ala Thr Ala Thr Thr Ala Gly Thr Gly Ala Ala Cys Ala
2385                2390                2395                2400
Cys Gly Ala Gly Gly Gly Thr Gly Ala Cys Cys Gly Thr Thr Gly Cys
        2405                2410                2415
Gly Ala Thr Gly Cys Thr Cys Cys Ala Gly Ala Cys Cys Thr Thr Cys
        2420                2425                2430
Ala Thr Thr Ala Ala Thr Cys Thr Cys Ala Ala Thr Cys Cys Ala Ala
        2435                2440                2445
Cys Thr Thr Cys Cys Thr Cys Ala Thr Cys Ala Thr Thr Thr Cys
        2450                2455                2460
Cys Ala Thr Thr Thr Cys Gly Ala Ala Thr Ala Thr Cys Thr Cys Thr
2465                2470                2475                2480
Thr Thr Thr Thr Cys Thr Thr Gly Cys Ala Cys Ala Gly Ala Ala Gly
                2485                2490                2495
Cys Cys Thr Thr Thr Thr Thr Cys Gly Thr Thr Thr Thr Thr Thr
        2500                2505                2510
Thr Thr Thr Ala Thr Thr Gly Ala Thr Thr Ala Thr Thr Thr Thr
        2515                2520                2525
Thr Ala Cys Gly Gly Ala Thr Thr Thr Thr Ala Gly Ala Thr Ala
        2530                2535                2540
Ala Thr Gly Cys Ala Cys Ala Gly Ala Thr Gly Cys Cys Thr Cys Ala
2545                2550                2555                2560
Thr Thr Gly Cys Thr Cys Ala Ala Ala Thr Ala Ala Ala Thr Thr Thr
                2565                2570                2575
Ala Thr Thr Thr Thr Ala Ala Thr Thr Ala Ala Ala Ala Ala Ala
        2580                2585                2590
Ala Ala Ala Ala Ala Ala Ala Ala Ala
        2595                2600

<210> SEQ ID NO 10
<211> LENGTH: 2601
<212> TYPE: DNA
<213> ORGANISM: Caenorhabditis elegans

<400> SEQUENCE: 10
aagtttgaga gtgatatagg agaaaaacct ccccaacatt ggctcacacc cggattatga     60
tcttctgctg ctcctgctgc tccttctgct gtagttgaga cgaagaagaa gaagaagctc    120
cattctcgag aaatggctcg tccattcaca cttatcgtac tcctctccgc acatctgtgt    180

-continued

```
ctacatgtgg ttgtgacaca ggatgaggac tcacatatca acactcaact cctctcatca      240
gttctcgata gactcacgaa tcgcactact tatgataaaa gattacggcc caggtatggt      300
gaaaagccag tcgacgttgg aattacgata cacgtttctt caatctctgc agtttcagaa      360
gttgatatgg acttcacatt agacttctac atgcgtcaaa cgtggcaaga ccctcgacta      420
gccttcggaa gtcttgattt gggactttcc aaagaaatcg actcacttac cgtcggagta      480
gactacctgg atagactgtg gaaacccgac acgttcttcc caaatgaaaa gaaatcattc      540
ttccacttgg caaccacaca taactcgttc cttcgtatcg agggtgatgg aacggtttat      600
actagtcaaa gattaacagt cactgcaacg tgtccaatgg acctgaagct gttcccaatg      660
gactctcaac actgtaaact ggaaattgaa agctacgggt acgagacgaa agatatcgac      720
tactattggg ggaagaagcg gactgatttg gagataacgg ctgtcaagtt tgataccttc      780
cagttgccgc agtttcagcc aacgctgtat tttgtgaata caactaaagc cgagacctca      840
tcaggaaaat acgtacgcct ggcgctggaa gtaatattgg ttcgaaatat gggcttctac      900
actatgaaca tcgtcatccc atccatcctg atcgtcacca tatcttgggt atcattttgg      960
ttgaatcgag aagcttcgcc ggctcgagtt ggattgggtg tgactactgt gctcacaatg     1020
acaactctga tcactacaac caataattcg atgccaaaag tgtcttatgt caagggtctg     1080
gatgtgtttc ttaatttttg tttcgtaatg gtattcgcct cgttgctcga gtacgccata     1140
gtatcctaca tgaataaacg actggtcctc cgacgggaaa aacgaagaaa agccgccgaa     1200
caacagcagc gaaacgagat gccaatgttc aacgcgagcc cgaaggccgc caataataat     1260
tcatacgaaa tgacacttat gtcgcaaaat tcgacgcctg ccaaaagcta tgtacaggct     1320
gacttgtact ttgccggaca caattcctct atgaatccat tgatggagat cccagaaaat     1380
tgtgattgcc ggacgattcc aatgatgcaa catccacgtc ttgtcacaga cggcgcacat     1440
acgctatggc cggctccatt cgcgcggccg aaaaaggctt ccaagacatg ctgccaacga     1500
tggacgcctg caaaaatcga taagcttagc cgatacggtt tcccattgtc tttctctatc     1560
ttcaatatag tctactggtt gtatatgaaa tatctaagct taaactcgtc ggacaagatc     1620
caggagaacg acaagtggca gcagatccac tgatgcgtat tcgacggccg aaatcgagta     1680
caaatggtgt acgtcgaagg agccgaattg ttcgacagcg gtcaaggccg acgcgaacat     1740
cgaactgtcg agttataaat tcactaaaat ctgccaaaaa cggacacttg ccagcacttc     1800
atcggggacc tactctcgtc tacgggttag tttcatattt gatcgcgaca gcggcttcta     1860 cttcttcaa atattttccc ctgccagcct cgtcgtagtt ttatcatgga tctcattctg     1920
gatcaatcgt gactcggcgc cttcgcgaac cctaatcggt acgatgacgg tgctcactga     1980
gactcatctt atgaccggaa ccaatcgacg tcttccacca gttgcctatg taaaagccgt     2040
tgatgtattc ctcggtttct gctatcttct ggttatactg gcgttgatcg agtacgcctg     2100
tgttgcctac tcaaaaaaga agaacgagga tcgtcggaga agagagaaga agacgggagca    2160 taaacctgct ccgccgacac ctgatattct tcacgacgtc cgccttgccg aatgcacatg     2220
caacgcggct ccaacctcga tcatcgccgt catcaagcag tcgaatcgat tctgtgtcag     2280
tcacagtcac attgacatcg tcagccgtgc cgcgtttcct cttgttttca tcttgttcaa     2340
cactctcttc tggctgattc tactgtacaa atccaagcgt ctgccgtata ttagtgaaca     2400
cgagggtgac cgttgcgatg ctccagacct tcattaatct caatccaact tcctcatcat     2460
tttccatttc gaatatctct tttttcttgca cagaagcctt ttttcgtttt ttttattga     2520 tttattttta cggattttta gataatgcac agatgcctca ttgctcaaat aaatttattt     2580
```
taattaaaaa aaaaaaaaaa a 2601

<210> SEQ ID NO 11
<211> LENGTH: 1128
<212> TYPE: PRT
<213> ORGANISM: Caenorhabditis elegans

<400> SEQUENCE: 11

Cys Gly Thr Thr Thr Thr Thr Thr Thr Thr Thr Thr Thr Thr Thr
1               5                   10                  15

Thr Gly Cys Ala Thr Thr Thr Thr Cys Ala Ala Ala Ala Ala
            20                  25                  30

Ala Ala Ala Ala Ala Ala Ala Thr Thr Ala Ala Gly Cys Thr Ala
        35                  40                  45

Gly Thr Ala Gly Thr Cys Thr Gly Thr Ala Thr Thr Cys Thr Gly
    50                  55                  60

Thr Thr Gly Cys Thr Thr Thr Cys Thr Thr Thr Cys Thr Cys Gly
65                  70                  75                  80

Thr Cys Gly Thr Cys Gly Thr Gly Cys Thr Thr Cys Cys Thr Cys
                85                  90                  95

Ala Thr Cys Ala Ala Cys Ala Thr Ala Gly Ala Thr Ala Gly Ala Thr
            100                 105                 110

Thr Cys Ala Ala Cys Cys Gly Cys Thr Ala Ala Cys Cys Thr
        115                 120                 125

Gly Thr Gly Thr Cys Ala Thr Cys Ala Thr Cys Cys Ala Ala
    130                 135                 140

Cys Cys Cys Ala Cys Cys Ala Ala Cys Cys Ala Thr Gly Ala Ala Gly
145                 150                 155                 160

Cys Cys Cys Ala Ala Thr Gly Thr Gly Thr Cys Ala Gly Ala Thr
                165                 170                 175

Gly Cys Gly Thr Ala Thr Thr Cys Gly Ala Cys Gly Gly Cys Gly
            180                 185                 190

Ala Ala Ala Thr Cys Gly Ala Gly Thr Ala Cys Ala Ala Ala Thr Gly
        195                 200                 205

Gly Thr Gly Thr Ala Cys Gly Thr Cys Gly Ala Ala Gly Gly Ala Gly
    210                 215                 220

Cys Cys Gly Ala Ala Thr Thr Gly Thr Thr Cys Gly Ala Cys Ala Gly
225                 230                 235                 240

Cys Gly Gly Thr Cys Ala Ala Gly Gly Cys Cys Gly Ala Cys Gly Cys
                245                 250                 255

Gly Ala Ala Cys Ala Thr Cys Gly Ala Ala Cys Thr Gly Thr Cys Gly
            260                 265                 270

Ala Gly Thr Thr Ala Thr Ala Ala Thr Thr Cys Ala Cys Thr Ala
        275                 280                 285

Ala Ala Ala Thr Cys Thr Gly Cys Cys Ala Ala Ala Ala Cys Gly
    290                 295                 300

Gly Ala Cys Ala Cys Thr Thr Gly Cys Ala Gly Cys Ala Cys Thr
305                 310                 315                 320

Thr Cys Ala Thr Cys Gly Gly Gly Ala Cys Cys Thr Ala Cys Thr
                325                 330                 335

Cys Thr Cys Gly Thr Cys Thr Ala Cys Gly Gly Thr Thr Ala Gly
            340                 345                 350

Thr Thr Thr Cys Ala Thr Ala Thr Thr Gly Ala Thr Cys Gly Cys
        355                 360                 365

-continued

```
Gly Ala Cys Ala Gly Cys Gly Gly Cys Thr Thr Cys Thr Ala Cys Thr
    370                 375                 380

Thr Thr Cys Thr Thr Cys Ala Ala Ala Thr Ala Thr Thr Thr Thr Thr
385                 390                 395                 400

Cys Cys Cys Thr Gly Cys Cys Ala Gly Cys Cys Thr Cys Gly Thr Cys
                405                 410                 415

Gly Thr Ala Gly Thr Thr Thr Thr Ala Thr Cys Ala Thr Gly Gly Ala
            420                 425                 430

Thr Cys Thr Cys Ala Thr Thr Cys Thr Gly Gly Ala Thr Cys Ala Ala
        435                 440                 445

Thr Cys Gly Thr Gly Ala Cys Thr Cys Gly Gly Cys Gly Cys Cys Thr
    450                 455                 460

Thr Cys Gly Cys Gly Ala Ala Cys Cys Cys Thr Ala Ala Thr Cys Gly
465                 470                 475                 480

Gly Thr Ala Cys Gly Ala Thr Gly Ala Cys Gly Gly Thr Gly Cys Thr
                485                 490                 495

Cys Ala Cys Thr Gly Ala Gly Ala Cys Thr Cys Ala Thr Cys Thr Thr
            500                 505                 510

Ala Thr Gly Ala Cys Cys Gly Gly Ala Ala Cys Cys Ala Ala Thr Cys
        515                 520                 525

Gly Ala Cys Gly Thr Cys Thr Thr Cys Cys Ala Cys Cys Ala Gly Thr
    530                 535                 540

Thr Gly Cys Cys Thr Ala Thr Gly Thr Ala Ala Ala Ala Gly Cys Cys
545                 550                 555                 560

Gly Thr Thr Gly Ala Thr Gly Thr Ala Thr Thr Cys Cys Thr Cys Gly
                565                 570                 575

Gly Thr Thr Thr Cys Thr Gly Cys Thr Ala Thr Cys Thr Thr Cys Thr
            580                 585                 590

Gly Gly Thr Thr Ala Thr Ala Cys Thr Gly Gly Cys Gly Thr Thr Gly
        595                 600                 605

Ala Thr Cys Gly Ala Gly Thr Ala Cys Gly Cys Cys Thr Gly Thr Gly
    610                 615                 620

Thr Thr Gly Cys Cys Thr Ala Cys Thr Cys Ala Ala Ala Ala Ala Ala
625                 630                 635                 640

Gly Ala Ala Gly Ala Ala Cys Gly Ala Gly Gly Ala Thr Cys Gly Thr
                645                 650                 655

Cys Gly Gly Ala Gly Ala Ala Gly Ala Gly Ala Gly Ala Ala Gly Ala
            660                 665                 670

Ala Gly Ala Cys Gly Gly Ala Gly Cys Ala Thr Ala Ala Ala Cys Cys
        675                 680                 685

Thr Gly Cys Thr Cys Cys Gly Cys Cys Gly Ala Cys Ala Cys Cys Thr
    690                 695                 700

Gly Ala Thr Ala Thr Thr Cys Thr Thr Cys Ala Cys Gly Ala Cys Gly
705                 710                 715                 720

Thr Cys Cys Gly Cys Cys Thr Thr Gly Cys Cys Gly Ala Ala Thr Gly
                725                 730                 735

Cys Ala Cys Ala Thr Gly Cys Ala Ala Cys Gly Cys Gly Gly Cys Thr
            740                 745                 750

Cys Cys Ala Ala Cys Cys Thr Cys Gly Ala Thr Cys Ala Thr Cys Gly
        755                 760                 765

Cys Cys Gly Thr Cys Ala Thr Cys Ala Ala Gly Cys Ala Gly Thr Cys
    770                 775                 780
```

Gly Ala Ala Thr Cys Gly Ala Thr Cys Thr Gly Thr Gly Thr Cys
785                 790                 795                 800

Ala Gly Thr Cys Ala Cys Ala Gly Thr Cys Ala Cys Ala Thr Thr Gly
                805                 810                 815

Ala Cys Ala Thr Cys Gly Thr Cys Ala Gly Cys Cys Gly Thr Gly Cys
                820                 825                 830

Cys Gly Cys Gly Thr Thr Thr Cys Cys Thr Cys Thr Thr Gly Thr Thr
            835                 840                 845

Thr Thr Cys Ala Thr Cys Thr Thr Gly Thr Thr Cys Ala Ala Cys Ala
        850                 855                 860

Cys Thr Cys Thr Cys Thr Thr Cys Thr Gly Gly Cys Thr Gly Ala Thr
865                 870                 875                 880

Thr Cys Thr Ala Cys Thr Gly Thr Ala Cys Ala Ala Ala Thr Cys Cys
                885                 890                 895

Ala Ala Gly Cys Gly Thr Cys Thr Gly Cys Cys Gly Thr Ala Thr Ala
                900                 905                 910

Thr Thr Ala Gly Thr Gly Ala Ala Cys Ala Cys Gly Ala Gly Gly Gly
            915                 920                 925

Thr Gly Ala Cys Cys Gly Thr Thr Gly Cys Gly Ala Thr Gly Cys Thr
        930                 935                 940

Cys Cys Ala Gly Ala Cys Cys Thr Thr Cys Ala Thr Thr Ala Ala Thr
945                 950                 955                 960

Cys Thr Cys Ala Ala Thr Cys Cys Ala Ala Cys Thr Cys Cys Cys Thr
                965                 970                 975

Cys Ala Thr Cys Ala Thr Thr Thr Thr Cys Cys Ala Thr Thr Thr Cys
                980                 985                 990

Gly Ala Ala Thr Ala Thr Cys Thr Cys Thr Thr Thr Thr Thr Cys Thr
            995                 1000                1005

Thr Gly Cys Ala Cys Ala Gly Ala Ala Gly Cys Cys Thr Thr Thr Thr
        1010                1015                1020

Thr Thr Cys Gly Thr Thr Thr Thr Thr Thr Thr Thr Thr Ala Thr Thr
1025                1030                1035                1040

Gly Ala Thr Thr Thr Ala Thr Thr Thr Thr Thr Ala Cys Gly Gly Ala
                1045                1050                1055

Thr Thr Thr Thr Thr Ala Gly Ala Thr Ala Ala Thr Gly Cys Ala Cys
                1060                1065                1070

Ala Gly Ala Thr Gly Cys Cys Thr Cys Ala Thr Thr Gly Cys Thr Cys
            1075                1080                1085

Ala Ala Ala Thr Ala Ala Ala Thr Thr Thr Ala Thr Thr Thr Thr Ala
        1090                1095                1100

Ala Thr Thr Gly Thr Cys Ala Ala Ala Ala Ala Ala Ala Ala Ala Ala
1105                1110                1115                1120

Ala Ala Ala Ala Ala Ala Ala Ala
                1125

<210> SEQ ID NO 12
<211> LENGTH: 1128
<212> TYPE: DNA
<213> ORGANISM: Caenorhabditis elegans

<400> SEQUENCE: 12 cgttttttttt tttttttgca tttttcaaaa aaaaaaaaaa ttaagctagt agtctgtaat      60
tctgttgctt ttctttctcg tcgtcgttgc ttcctcatca acatagatag attcaacccg     120
cttaacctgt gtcatcatat ccaacccacc aaccatgaag cccaatgtgt tcagatgcgt     180

```
attcgacggc cgaaatcgag tacaaatggt gtacgtcgaa ggagccgaat tgttcgacag    240
cggtcaaggc cgacgcgaac atcgaactgt cgagttataa attcactaaa atctgccaaa    300
aacggacact tgccagcact tcatcgggga cctactctcg tctacgggtt agtttcatat    360
ttgatcgcga cagcggcttc tactttcttc aaatattttt ccctgccagc ctcgtcgtag    420
ttttatcatg gatctcattc tggatcaatc gtgactcggc ccttcgcga accctaatcg     480 gtacgatgac ggtgctcact gagactcatc ttatgaccgg aaccaatcga cgtcttccac    540
cagttgccta tgtaaaagcc gttgatgtat tcctcggttt ctgctatctt ctggttatac    600
tggcgttgat cgagtacgcc tgtgttgcct actcaaaaaa gaagaacgag gatcgtcgga    660
gaagagagaa gaagacggag cataaacctg ctccgccgac acctgatatt cttcacgacg    720
tccgccttgc cgaatgcaca tgcaacgcgg ctccaacctc gatcatcgcc gtcatcaagc    780
agtcgaatcg attctgtgtc agtcacagtc acattgacat cgtcagccgt gccgcgtttc    840
ctcttgtttt catcttgttc aacactctct tctggctgat tctactgtac aaatccaagc    900
gtctgccgta tattagtgaa cacgagggtg accgttgcga tgctccagac cttcattaat    960
ctcaatccaa cttcctcatc attttccatt tcgaatatct cttttcttg cacagaagcc    1020 ttttttcgtt ttttttatt gatttatttt tacggatttt tagataatgc acagatgcct    1080
cattgctcaa ataaatttat tttaattgtc aaaaaaaaa aaaaaaa                  1128
```

<210> SEQ ID NO 13
<211> LENGTH: 487
<212> TYPE: PRT
<213> ORGANISM: Artificial Sequence
<220> FEATURE:
<223> OTHER INFORMATION: UNC-49A
<220> FEATURE:
<223> OTHER INFORMATION: Description of Artificial Sequence =
      Note/Artificial Sequence = synthetic construct

<400> SEQUENCE: 13

```
Met Ala Arg Pro Phe Thr Leu Ile Val Leu Leu Ser Ala His Leu Cys
 1               5                  10                  15

Leu His Val Val Val Thr Gln Asp Glu Asp Ser His Ile Asn Thr Gln
                20                  25                  30

Leu Leu Ser Ser Val Leu Asp Arg Leu Thr Asn Arg Thr Thr Tyr Asp
            35                  40                  45

Lys Arg Leu Arg Pro Arg Tyr Gly Glu Lys Pro Val Asp Val Gly Ile
        50                  55                  60

Thr Ile His Val Ser Ser Ile Ser Ala Val Ser Glu Val Asp Met Asp
 65                  70                  75                  80

Phe Thr Leu Asp Phe Tyr Met Arg Gln Thr Trp Gln Asp Pro Arg Leu
                85                  90                  95

Ala Phe Gly Ser Leu Asp Leu Gly Leu Ser Lys Glu Ile Asp Ser Leu
                100                 105                 110

Thr Val Gly Val Asp Tyr Leu Asp Arg Leu Trp Lys Pro Asp Thr Phe
            115                 120                 125

Phe Pro Asn Glu Lys Lys Ser Phe His Leu Ala Thr Thr His Asn
        130                 135                 140

Ser Phe Leu Arg Ile Glu Gly Asp Gly Thr Val Tyr Thr Ser Gln Arg
145                 150                 155                 160

Leu Thr Val Thr Ala Thr Cys Pro Met Asp Leu Lys Leu Phe Pro Met
                165                 170                 175
```

-continued

```
Asp Ser Gln His Cys Lys Leu Glu Ile Glu Ser Tyr Gly Tyr Ser Ile
            180                 185                 190

Leu Asp Ile Met Tyr Val Ser His Glu Lys Lys Ser Val Ser Thr Glu
            195                 200                 205

Ser Tyr Glu Leu Pro Gln Phe Val Leu Gln Ser Ile Lys Val Val Asn
    210                 215                 220

His Thr Gln Lys Leu Ser Ser Gly Glu Tyr Ser Arg Leu Cys Trp Phe
225                 230                 235                 240

Phe Leu Phe Lys Arg Asn Ile Gly Phe Tyr Ile Ile Gln Ile Tyr Leu
                245                 250                 255

Pro Ser Val Leu Ile Val Val Ile Ser Trp Val Ser Phe Trp Leu Ser
            260                 265                 270

Arg Asp Ala Thr Pro Ala Arg Val Ala Leu Gly Val Thr Thr Val Leu
            275                 280                 285

Thr Met Thr Thr Leu Met Thr Met Thr Asn Ser Ser Met Pro Lys Val
290                 295                 300

Ser Tyr Val Lys Ser Ile Asp Ile Phe Leu Gly Val Cys Phe Met Met
305                 310                 315                 320

Val Phe Cys Ser Leu Leu Glu Tyr Ala Ala Val Gly Tyr Ile Ser Lys
                325                 330                 335

Arg Met Lys Leu Val Arg Ala Arg Lys Glu Ser Arg Met Leu Thr Pro
            340                 345                 350

Leu Pro His Leu Glu Ser Leu Pro Pro Lys Arg Thr Leu Ser Val Pro
            355                 360                 365

Ser Tyr Phe Asn Asn Thr Thr Tyr Arg Pro Phe Tyr Ser Ser Thr Asp
    370                 375                 380

Gln Thr Ser Asn Leu Tyr Ile Pro Glu Ser Gln Arg Thr Thr Ile Phe
385                 390                 395                 400

Ser Asn Glu Asp Ala Val Pro Asn Glu Leu Thr Pro Met Leu Gly Arg
                405                 410                 415

Ser Asn Ser Gln Ala Ser Val Phe Leu Tyr Gln Thr Ala Val Ile Ser
            420                 425                 430

Asp Asp Glu Phe Gly Arg Phe Trp Arg Trp Leu Arg Pro Ser Asn Ile
            435                 440                 445

Asp Lys Tyr Ser Arg Ser Leu Phe Pro Ser Ile Phe Val Leu Phe Asn
    450                 455                 460

Val Gly Tyr Trp Ala Tyr Phe Ile Arg Gln Ser Gln Ile Gln Glu Glu
465                 470                 475                 480

Gln Arg Asn Ser Gln Ile Leu
                485
```

<210> SEQ ID NO 14
<211> LENGTH: 487
<212> TYPE: PRT
<213> ORGANISM: Artificial Sequence
<220> FEATURE:
<223> OTHER INFORMATION: UNC-49B.1
<220> FEATURE:
<223> OTHER INFORMATION: Description of Artificial Sequence =
      Note/Artificial Sequence = synthetic construct

<400> SEQUENCE: 14

```
Met Ala Arg Pro Phe Thr Leu Ile Val Leu Leu Ser Ala His Leu Cys
 1               5                  10                  15

Leu His Val Val Thr Gln Asp Glu Asp Ser His Ile Asn Thr Gln
             20                  25                  30
```

-continued

```
Leu Leu Ser Ser Val Leu Asp Arg Leu Thr Asn Arg Thr Thr Tyr Asp
            35                  40                  45

Lys Arg Leu Arg Pro Arg Tyr Gly Glu Lys Pro Val Asp Val Gly Ile
        50                  55                  60

Thr Ile His Val Ser Ser Ile Ser Ala Val Ser Glu Val Asp Met Asp
65                  70                  75                  80

Phe Thr Leu Asp Phe Tyr Met Arg Gln Thr Trp Gln Asp Pro Arg Leu
                85                  90                  95

Ala Phe Gly Ser Leu Asp Leu Gly Leu Ser Lys Glu Ile Asp Ser Leu
            100                 105                 110

Thr Val Gly Val Asp Tyr Leu Asp Arg Leu Trp Lys Pro Asp Thr Phe
        115                 120                 125

Phe Pro Asn Glu Lys Lys Ser Phe Phe His Leu Ala Thr Thr His Asn
        130                 135                 140

Ser Phe Leu Arg Ile Glu Gly Asp Gly Thr Val Tyr Thr Ser Gln Arg
145                 150                 155                 160

Leu Thr Val Thr Ala Thr Cys Pro Met Asp Leu Lys Leu Phe Pro Met
                165                 170                 175

Asp Ser Gln His Cys Lys Leu Glu Ile Glu Ser Tyr Gly Tyr Glu Thr
            180                 185                 190

Lys Asp Ile Asp Tyr Tyr Trp Gly Lys Lys Arg Thr Asp Leu Glu Ile
        195                 200                 205

Thr Ala Val Lys Phe Asp Thr Phe Gln Leu Pro Gln Phe Gln Pro Thr
    210                 215                 220

Leu Tyr Phe Val Asn Thr Thr Lys Ala Glu Thr Ser Ser Gly Lys Tyr
225                 230                 235                 240

Val Arg Leu Ala Leu Glu Val Ile Leu Val Arg Asn Met Gly Phe Tyr
                245                 250                 255

Thr Met Asn Ile Val Ile Pro Ser Ile Leu Ile Val Thr Ile Ser Trp
                260                 265                 270

Val Ser Phe Trp Leu Asn Arg Glu Ala Ser Pro Ala Arg Val Gly Leu
            275                 280                 285

Gly Val Thr Thr Val Leu Thr Met Thr Thr Leu Ile Thr Thr Thr Asn
        290                 295                 300

Asn Ser Met Pro Lys Val Ser Tyr Val Lys Gly Leu Asp Val Phe Leu
305                 310                 315                 320

Asn Phe Cys Phe Val Met Val Phe Ala Ser Leu Leu Glu Tyr Ala Ile
                325                 330                 335

Val Ser Tyr Met Asn Lys Arg Leu Val Leu Arg Arg Glu Lys Arg Arg
            340                 345                 350

Lys Ala Ala Glu Gln Gln Arg Asn Glu Met Pro Met Phe Asn Ala
        355                 360                 365

Ser Pro Lys Ala Ala Asn Asn Asn Ala Asp Leu Tyr Phe Ala Gly His
    370                 375                 380

Asn Ser Ser Met Asn Pro Leu Met Glu Ile Pro Glu Asn Cys Asp Cys
385                 390                 395                 400

Arg Thr Ile Pro Met Met Gln His Pro Arg Leu Val Thr Asp Gly Ala
                405                 410                 415

His Thr Leu Trp Pro Ala Pro Phe Ala Arg Pro Lys Lys Ala Ser Lys
            420                 425                 430

Thr Cys Cys Gln Arg Trp Thr Pro Ala Lys Ile Asp Lys Leu Ser Arg
        435                 440                 445

Tyr Gly Phe Pro Leu Ser Phe Ser Ile Phe Asn Ile Val Tyr Trp Leu
```

```
            450                 455                 460
Tyr Met Lys Tyr Leu Ser Leu Asn Ser Ser Asp Lys Ile Gln Glu Asn
465                 470                 475                 480

Asp Lys Trp Gln Gln Ile His
                485

<210> SEQ ID NO 15
<211> LENGTH: 506
<212> TYPE: PRT
<213> ORGANISM: Artificial Sequence
<220> FEATURE:
<223> OTHER INFORMATION: UNC-49B.3
<220> FEATURE:
<223> OTHER INFORMATION: Description of Artificial Sequence =
      Note/Artificial Sequence = synthetic construct

<400> SEQUENCE: 15

Met Ala Arg Pro Phe Thr Leu Ile Val Leu Leu Ser Ala His Leu Cys
 1               5                  10                  15

Leu His Val Val Val Thr Gln Asp Glu Asp Ser His Ile Asn Thr Gln
                20                  25                  30

Leu Leu Ser Ser Val Leu Asp Arg Leu Thr Asn Arg Thr Thr Tyr Asp
            35                  40                  45

Lys Arg Leu Arg Pro Arg Tyr Gly Glu Lys Pro Val Asp Val Gly Ile
 50                  55                  60

Thr Ile His Val Ser Ser Ile Ser Ala Val Ser Glu Val Asp Met Asp
 65                  70                  75                  80

Phe Thr Leu Asp Phe Tyr Met Arg Gln Thr Trp Gln Asp Pro Arg Leu
                85                  90                  95

Ala Phe Gly Ser Leu Asp Leu Gly Leu Ser Lys Glu Ile Asp Ser Leu
            100                 105                 110

Thr Val Gly Val Asp Tyr Leu Asp Arg Leu Trp Lys Pro Asp Thr Phe
        115                 120                 125

Phe Pro Asn Glu Lys Lys Ser Phe Phe His Leu Ala Thr Thr His Asn
    130                 135                 140

Ser Phe Leu Arg Ile Glu Gly Asp Gly Thr Val Tyr Thr Ser Gln Arg
145                 150                 155                 160

Leu Thr Val Thr Ala Thr Cys Pro Met Asp Leu Lys Leu Phe Pro Met
                165                 170                 175

Asp Ser Gln His Cys Lys Leu Glu Ile Glu Ser Tyr Gly Tyr Glu Thr
            180                 185                 190

Lys Asp Ile Asp Tyr Tyr Trp Gly Lys Lys Arg Thr Asp Leu Glu Ile
        195                 200                 205

Thr Ala Val Lys Phe Asp Thr Phe Gln Leu Pro Gln Phe Gln Pro Thr
    210                 215                 220

Leu Tyr Phe Val Asn Thr Thr Lys Ala Glu Thr Ser Ser Gly Lys Tyr
225                 230                 235                 240

Val Arg Leu Ala Leu Glu Val Ile Leu Val Arg Asn Met Gly Phe Tyr
                245                 250                 255

Thr Met Asn Ile Val Ile Pro Ser Ile Leu Ile Val Thr Ile Ser Trp
            260                 265                 270

Val Ser Phe Trp Leu Asn Arg Glu Ala Ser Pro Ala Arg Val Gly Leu
        275                 280                 285

Gly Val Thr Thr Val Leu Thr Met Thr Thr Leu Ile Thr Thr Thr Asn
    290                 295                 300

Asn Ser Met Pro Lys Val Ser Tyr Val Lys Gly Leu Asp Val Phe Leu
```

-continued

```
                305                 310                 315                 320
Asn Phe Cys Phe Val Met Val Phe Ala Ser Leu Leu Glu Tyr Ala Ile
                325                 330                 335

Val Ser Tyr Met Asn Lys Arg Leu Val Leu Arg Arg Glu Lys Arg Arg
                340                 345                 350

Lys Ala Ala Glu Gln Gln Arg Asn Glu Met Pro Met Phe Asn Ala
                355                 360                 365

Ser Pro Lys Ala Ala Asn Asn Ser Tyr Glu Met Thr Leu Met Ser
            370                 375                 380

Gln Asn Ser Thr Pro Ala Lys Ser Tyr Val Gln Ala Asp Leu Tyr Phe
385                 390                 395                 400

Ala Gly His Asn Ser Ser Met Asn Pro Leu Met Glu Ile Pro Glu Asn
                405                 410                 415

Cys Asp Cys Arg Thr Ile Pro Met Met Gln His Pro Arg Leu Val Thr
                420                 425                 430

Asp Gly Ala His Thr Leu Trp Pro Ala Pro Phe Ala Arg Pro Lys Lys
                435                 440                 445

Ala Ser Lys Thr Cys Cys Gln Arg Trp Thr Pro Ala Lys Ile Asp Lys
                450                 455                 460

Leu Ser Arg Tyr Gly Phe Pro Leu Ser Phe Ser Ile Phe Asn Ile Val
465                 470                 475                 480

Tyr Trp Leu Tyr Met Lys Tyr Leu Ser Leu Asn Ser Ser Asp Lys Ile
                485                 490                 495

Gln Glu Asn Asp Lys Trp Gln Gln Ile His
                500                 505

<210> SEQ ID NO 16
<211> LENGTH: 475
<212> TYPE: PRT
<213> ORGANISM: Artificial Sequence
<220> FEATURE:
<223> OTHER INFORMATION: UNC-49B.2
<220> FEATURE:
<223> OTHER INFORMATION: Description of Artificial Sequence =
      Note/Artificial Sequence = synthetic construct

<400> SEQUENCE: 16

Met Ala Arg Pro Phe Thr Leu Ile Val Leu Leu Ser Ala His Leu Cys
1               5                   10                  15

Leu His Val Val Thr Gln Asp Glu Asp Ser His Ile Asn Thr Gln
                20                  25                  30

Leu Leu Ser Ser Val Leu Asp Arg Leu Thr Asn Arg Thr Thr Tyr Asp
                35                  40                  45

Lys Arg Leu Arg Pro Arg Tyr Gly Glu Lys Pro Val Asp Val Gly Ile
            50                  55                  60

Thr Ile His Val Ser Ser Ile Ser Ala Val Ser Glu Val Asp Met Asp
65                  70                  75                  80

Phe Thr Leu Asp Phe Tyr Met Arg Gln Thr Trp Gln Asp Pro Arg Leu
                85                  90                  95

Ala Phe Gly Ser Leu Asp Leu Gly Leu Ser Lys Glu Ile Asp Ser Leu
                100                 105                 110

Thr Val Gly Val Asp Tyr Leu Asp Arg Leu Trp Lys Pro Asp Thr Phe
            115                 120                 125

Phe Pro Asn Glu Lys Lys Ser Phe Phe His Leu Ala Thr Thr His Asn
            130                 135                 140

Ser Phe Leu Arg Ile Glu Gly Asp Gly Thr Val Tyr Thr Ser Gln Arg
```

```
                145                 150                 155                 160
Leu Thr Val Thr Ala Thr Cys Pro Met Asp Leu Lys Leu Phe Pro Met
                165                 170                 175
Asp Ser Gln His Cys Lys Leu Glu Ile Glu Ser Tyr Gly Tyr Glu Thr
                180                 185                 190
Lys Asp Ile Asp Tyr Tyr Trp Gly Lys Lys Thr Asp Leu Glu Ile
                195                 200                 205
Thr Ala Val Lys Phe Asp Thr Phe Gln Leu Pro Gln Phe Gln Pro Thr
                210                 215                 220
Leu Tyr Phe Val Asn Thr Thr Lys Ala Glu Thr Ser Ser Gly Lys Tyr
225                 230                 235                 240
Val Arg Leu Ala Leu Glu Val Ile Leu Val Arg Asn Met Gly Phe Tyr
                245                 250                 255
Thr Met Asn Ile Val Ile Pro Ser Ile Leu Ile Val Thr Ile Ser Trp
                260                 265                 270
Val Ser Phe Trp Leu Asn Arg Glu Ala Ser Pro Ala Arg Val Gly Leu
                275                 280                 285
Gly Val Thr Thr Val Leu Thr Met Thr Thr Leu Ile Thr Thr Asn
                290                 295                 300
Asn Ser Met Pro Lys Val Ser Tyr Val Lys Gly Leu Asp Val Phe Leu
305                 310                 315                 320
Asn Phe Cys Phe Val Met Val Phe Ala Ser Leu Leu Glu Tyr Ala Ile
                325                 330                 335
Val Ser Tyr Met Asn Lys Arg Leu Val Leu Arg Arg Glu Lys Arg Arg
                340                 345                 350
Lys Ala Ala Glu Gln Gln Gln Arg Asn Glu Met Pro Met Phe Asn Ala
                355                 360                 365
Ser Pro Lys Ala Ala Asn Asn Asn Pro Leu Met Glu Ile Pro Glu
                370                 375                 380
Asn Cys Asp Cys Arg Thr Ile Pro Met Met Gln His Pro Arg Leu Val
385                 390                 395                 400
Thr Asp Gly Ala His Thr Leu Trp Pro Ala Pro Phe Ala Arg Pro Lys
                405                 410                 415
Lys Ala Ser Lys Thr Cys Cys Gln Arg Trp Thr Pro Ala Lys Ile Asp
                420                 425                 430
Lys Leu Ser Arg Tyr Gly Phe Pro Leu Ser Phe Ser Ile Phe Asn Ile
                435                 440                 445
Val Tyr Trp Leu Tyr Met Lys Tyr Leu Ser Leu Asn Ser Ser Asp Lys
                450                 455                 460
Ile Gln Glu Asn Asp Lys Trp Gln Gln Ile His
465                 470                 475

<210> SEQ ID NO 17
<211> LENGTH: 448
<212> TYPE: PRT
<213> ORGANISM: Artificial Sequence
<220> FEATURE:
<223> OTHER INFORMATION: UNC-49C
<220> FEATURE:
<223> OTHER INFORMATION: Description of Artificial Sequence =
      Note/Artificial Sequence = synthetic construct

<400> SEQUENCE: 17

Met Ala Arg Pro Phe Thr Leu Ile Val Leu Leu Ser Ala His Leu Cys
1               5                   10                  15

Leu His Val Val Val Thr Gln Asp Glu Asp Ser His Ile Asn Thr Gln
```

```
                    20                  25                  30
Leu Leu Ser Ser Val Leu Asp Arg Leu Thr Asn Arg Thr Tyr Asp
                35                  40                  45
Lys Arg Leu Arg Pro Arg Tyr Gly Glu Lys Pro Val Asp Val Gly Ile
    50                  55                  60
Thr Ile His Val Ser Ser Ile Ser Ala Val Ser Glu Val Asp Met Asp
65                  70                  75                  80
Phe Thr Leu Asp Phe Tyr Met Arg Gln Thr Trp Gln Asp Pro Arg Leu
                85                  90                  95
Ala Phe Gly Ser Leu Asp Leu Gly Leu Ser Lys Glu Ile Asp Ser Leu
                100                 105                 110
Thr Val Gly Val Asp Tyr Leu Asp Arg Leu Trp Lys Pro Asp Thr Phe
                115                 120                 125
Phe Pro Asn Glu Lys Lys Ser Phe Phe His Leu Ala Thr His Asn
        130                 135                 140
Ser Phe Leu Arg Ile Glu Gly Asp Gly Thr Val Tyr Thr Ser Gln Arg
145                 150                 155                 160
Leu Thr Val Thr Ala Thr Cys Pro Met Asp Leu Lys Leu Phe Pro Met
                165                 170                 175
Asp Ser Gln His Cys Lys Leu Glu Ile Glu Ser Tyr Ala Tyr Ser Thr
                180                 185                 190
Ala Glu Ile Glu Tyr Lys Trp Cys Thr Ser Lys Glu Pro Asn Cys Ser
                195                 200                 205
Thr Ala Val Lys Ala Asp Ala Asn Ile Glu Leu Ser Ser Tyr Lys Phe
                210                 215                 220
Thr Lys Ile Cys Gln Lys Arg Thr Leu Ala Ser Thr Ser Ser Gly Thr
225                 230                 235                 240
Tyr Ser Arg Leu Arg Val Ser Phe Ile Phe Asp Arg Asp Ser Gly Phe
                245                 250                 255
Tyr Phe Leu Gln Ile Phe Phe Pro Ala Ser Leu Val Val Val Leu Ser
                260                 265                 270
Trp Ile Ser Phe Trp Ile Asn Arg Asp Ser Ala Pro Ser Arg Thr Leu
                275                 280                 285
Ile Gly Thr Met Thr Val Leu Thr Glu Thr His Leu Met Thr Gly Thr
                290                 295                 300
Asn Arg Arg Leu Pro Pro Val Ala Tyr Val Lys Ala Val Asp Val Phe
305                 310                 315                 320
Leu Gly Phe Cys Tyr Leu Leu Val Ile Leu Ala Leu Ile Glu Tyr Ala
                325                 330                 335
Cys Val Ala Tyr Ser Lys Lys Asn Glu Asp Arg Arg Arg Glu
                340                 345                 350
Lys Lys Thr Glu His Lys Pro Ala Pro Pro Thr Pro Asp Ile Leu His
                355                 360                 365
Asp Val Arg Leu Ala Glu Cys Thr Cys Asn Ala Ala Pro Thr Ser Ile
                370                 375                 380
Ile Ala Val Ile Lys Gln Ser Asn Arg Phe Cys Val Ser His Ser His
385                 390                 395                 400
Ile Asp Ile Val Ser Arg Ala Ala Phe Pro Leu Val Phe Ile Leu Phe
                405                 410                 415
Asn Thr Leu Phe Trp Leu Ile Leu Leu Tyr Lys Ser Lys Arg Leu Pro
                420                 425                 430
Tyr Ile Ser Glu His Glu Gly Asp Arg Cys Asp Ala Pro Asp Leu His
                435                 440                 445
```

-continued

```
<210> SEQ ID NO 18
<211> LENGTH: 264
<212> TYPE: PRT
<213> ORGANISM: Artificial Sequence
<220> FEATURE:
<223> OTHER INFORMATION: UNC-49C short
<220> FEATURE:
<223> OTHER INFORMATION: Description of Artificial Sequence =
      Note/Artificial Sequence = synthetic construct

<400> SEQUENCE: 18

Met Cys Ser Asp Ala Tyr Ser Thr Ala Glu Ile Glu Tyr Lys Trp Cys
 1               5                  10                  15

Thr Ser Lys Glu Pro Asn Cys Ser Thr Ala Val Lys Ala Asp Ala Asn
            20                  25                  30

Ile Glu Leu Ser Ser Tyr Lys Phe Thr Lys Ile Cys Gln Lys Arg Thr
        35                  40                  45

Leu Ala Ser Thr Ser Ser Gly Thr Tyr Ser Arg Leu Arg Val Ser Phe
    50                  55                  60

Ile Phe Asp Arg Asp Ser Gly Phe Tyr Phe Leu Gln Ile Phe Phe Pro
65                  70                  75                  80

Ala Ser Leu Val Val Val Leu Ser Trp Ile Ser Phe Trp Ile Asn Arg
                85                  90                  95

Asp Ser Ala Pro Ser Arg Thr Leu Ile Gly Thr Met Thr Val Leu Thr
            100                 105                 110

Glu Thr His Leu Met Thr Gly Thr Asn Arg Arg Leu Pro Pro Val Ala
        115                 120                 125

Tyr Val Lys Ala Val Asp Val Phe Leu Gly Phe Cys Tyr Leu Leu Val
    130                 135                 140

Ile Leu Ala Leu Ile Glu Tyr Ala Cys Val Ala Tyr Ser Lys Lys Lys
145                 150                 155                 160

Asn Glu Asp Arg Arg Arg Glu Lys Lys Thr Glu His Lys Pro Ala
            165                 170                 175

Pro Pro Thr Pro Asp Ile Leu His Asp Val Arg Leu Ala Glu Cys Thr
        180                 185                 190

Cys Asn Ala Ala Pro Thr Ser Ile Ile Ala Val Ile Lys Gln Ser Asn
    195                 200                 205

Arg Phe Cys Val Ser His Ser His Ile Asp Ile Val Ser Arg Ala Ala
210                 215                 220

Phe Pro Leu Val Phe Ile Leu Phe Asn Thr Leu Phe Trp Leu Ile Leu
225                 230                 235                 240

Leu Tyr Lys Ser Lys Arg Leu Pro Tyr Ile Ser Glu His Glu Gly Asp
            245                 250                 255

Arg Cys Asp Ala Pro Asp Leu His
        260
```

NEMATODE NEUROMUSCULAR JUNCTION GABA RECEPTORS AND METHODS RELATED THERETO

This application is a divisional of, and claims the benefit of, application Ser. No. 10/156,240 filed May 24, 2002, which has issued as U.S. Pat. No. 7,038,033, which is a continuation of application Ser. No. 09/436,063, filed on Nov. 8, 1999, which has issued as U.S. Pat. No. 6,407,210, which claims priority to U.S. Provisional Application 60/107,727, filed on Nov. 9, 1998, all of which are hereby incorporated herein in their entireties by reference.

FIELD OF THE INVENTION

The present invention relates to the field of GABA receptor structure and function. In one aspect, the present invention relates to impairment of the gamma-aminobutyric acid (GABA) receptors in parasitic nematodes, for the purpose of crop protection and/or soil treatment. The invention includes mutated nematode GABA receptor subunits, nematode GABA neuromuscular junction receptor complexes, nucleic acids which encode the mutated and functional receptor complexes, antibodies which selectively bind the GABA receptor complexes and/or subunits, and assays for compounds which adversely affect nematode GABA neuromuscular junction receptor function. The present invention therefore relates broadly to recombinant DNA technology, molecular biology tools, and crop protection and/or soil treatment.

The present invention also relates to the fields of GABA neurotransmitter research, particularly with regard to drug discovery. In that regard, the invention includes assays for substances which affect GABA receptors, as well as the tools necessary to conduct such assays, such as nucleic acids, amino acids, antibodies, vectors and cell lines.

BACKGROUND OF THE INVENTION

Nematodes (nema—thread; oides—resembling), which are unsegmented roundworms with elongated, fusiform, or saclike bodies covered with cuticle, are virtually ubiquitous in nature, inhabiting soil, water and plants, and are importantly involved in a wide range of animal and plant parasitic diseases.

Nematodes are Animal Pathogens

The roundworm parasites of mammals belong to the phylum Nemathelminthes. The roundworms include the hookworm (e.g. *Necator americanus* and *Ancylostoma duodenale*), roundworm (e.g. the common roundworm *Ascaris lumbricoides*), whipworm (e.g. *Trichuris trichiura*), and the pinworm or threadworm (e.g. *Enterobius vermicularus*), as well as *Strongyloides stercoralis, Trichinella spiralis* and the filarial worm *Wuchereria bancrofti*. Other important roundworm parasites include *Ancylostoma caninum* (infections of man), *Strongylus vulgaris* (infections of horses), *Trichostrongylus colubriformis, Ostertagia circumcincta* (infections of sheep and goats), *Haemonchus contortus* (infections of sheep and goats), *Ostertagia ostertagi, Haemonchus placei* (infections of cattle), *Ascaris suum* (infections of pigs), *Toxascaris leonina* or *Uncinaria stenocephala* (infections of dogs), *Toxocara* spp (circulatory infections of man) and *Dirofilaria immitis* (circulatory infections of cats and dogs).

Even when symptom-free, parasitic worm infections are harmful to the host animal for a number of reasons; e.g. they deprive the host of food, injure organs or obstruct ducts, may elaborate substances toxic to the host, and provide a port of entry for other organisms. In other cases, the host may be a species raised for food and the parasite may be transmitted upon eating to infect the ingesting animal. It is highly desirable to eliminate such parasites as soon as they have been discovered.

More commonly, such infections are not symptom-free. Helminth infections of mammals, particularly by parasitic nematodes, are a source of great economic loss, especially of livestock and pets, e.g. sheep, cattle, horses, pigs, goats, dogs, cats, and birds, especially poultry (see CSIRO/BAE Report—"Socio-economic Developments and Trends in the Agricultural Sector: Implications for Future Research"). These animals must be regularly treated with anthelminthic chemicals in order to keep such infections under control, or else the disease may result in anaemia, diarrhoea, dehydration, loss of appetite, and even death.

The only currently available means for controlling helminth infections is with the use of anthelminthic chemicals, but these are only effective against resident worms present at the time of treatment. Therefore, treatment must be continuous since the animals are constantly exposed to infection; e.g. anthelminthic treatment with diethylcarbamazine is required every day or every other day most of the year to control *Dirofilaria immitis* or the dog heartworm. This is an expensive and labour intensive procedure. Due to the widespread use of anthelminthic chemicals, the worms may develop resistance and so new and more potent classes of chemicals must be developed. An alternative approach is clearly desirable.

The accepted methodology for pharmaceutical control of nematodes has centered around the use of the drug benzimidazole and its congeners. The use of these drugs on a wide scale has led to many instances of resistance among nematode populations (Prichard et al., 1980; Coles, 1986). There are more than 100,000 described species of nematodes.

Other options for a drug treatment include employing an avermectin, pyrantel, morantel, closantel, praziquantel etc. Benzimidazole(s) or benzimidazole prodrug treatments include oxfendazole, thiabendazole, albendazole, cambenazole, fenbendazole, flubendazole, mebendazole, oxibendazole, parbendazole, thiophanate, febantel and netobimin.

Nematodes are Plant Pathogens

Nematodes thrive in virtually all environments throughout the world and are one of the largest and most diverse groups of multicellular organisms. Many species are parasites of agronomic crops, but other species are beneficial to agriculture. Nematodes that parasitize plants cause an estimated $8 billion annual loss (12%) to U.S. growers and nearly $78 billion loss globally. For example, the soybean cyst nematode causes annual losses in the North Central Region of the U.S. amounting to $267 million.

Traditional nematode reduction methods usually rely on a combination of petroleum byproduct soil treatments and crop rotation. Stricter environmental regulations are forecasted to limit the use of petroleum by-products, and threaten to impact agriculture if no safer alternatives are found or invented. A review of the impact of nematodes on crops can be found in: Hussey, R. Plant & Soil Nematodes: Societal Impact and Focus for the Future and can be obtained by writing to Department of Plant Pathology, University of Georgia, Athens, Ga. USA 30602-7274.

GABA Receptors

The gamma-aminobutyric acid receptors (GABA receptors) are the most abundant inhibitory receptor in the mammalian brain. They are comprised of a heteropolymeric structure that form a chloride ion channel, and contain multiple recognition sites for the binding of molecules. The binding of GABA to its specific recognition site on the a GABA receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA receptor (Puia, G. et al. Molecular Pharm. 1991, 39, 691).

Many clinical conditions are thought to arise, in part, from the imbalance between neurotransmission of GABA and those of other neurotransmitters. These conditions include Huntington's chorea, Parkinson's disease, spasticity, epilepsy, schizophrenia and tardive dyskinesia. Decreased GABA activity appears to contribute to the pathogenesis of these diseases. In addition, analgesia and satiety are thought to be regulated by GABA activity. Methods of modifying GABAergic neurotransmission are therefore desirable in order to modify these conditions.

The so-called benzodiazepine (BZD) receptor is a site for such allosteric modulators on one class of the GABA receptor, the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. J. Med. Chem. 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, antiinebriant, and anxiogenic activities, produced by inverse agonists ("negative"). (A further understanding of this area can be gleaned from: Mohler, H. Arzneim.-Forsch./Drug Res. 1992, 42 (2a), 211; Haefely, W. et al., Advances in Drug Research, Academic Press, vol. 14, 1985, pp. 165-322; Skolnick, P. et al., GABA and Benzodiazepine Receptors, Squires, R., Ed., 1987, pp. 99-102 and references cited therein.)

The fourth edition of the Diagnostic and Statistical Manual of Mental Disorders (DSM-IV.TM.), published in 1994 by the American Psychiatric Association, Washington, D.C., defines anxiety and related disorders. These are panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Anxiety disorders are generally treated by counseling or with drugs. Classes of drugs which are widely prescribed for the treatment of anxiety disorders include the benzodiazepines (such as diazepam) and buspirone hydrochloride.

Several animal models have been developed which are recognized in the art as being predictive of anxiolytic activity. These include the fear-potentiated startle model, described by Davis in Psychopharmacology 62:1; 1979, Behav. Neurosci. 100:814;1986 and TiPS, January 1992 Vol. 13, 35-41, the elevated plus model described by Lister in Psychopharmacol. 92:180-185; 1987, and the well-known punished—responding (conflict) model, described, for example, in "Psychopharmacology of Anxiolytics and Antidepressants", edited by S. E. File, pp. 131-153, Raven Press, New York, 1991.

Citation of the above documents is not intended as an admission that any of the foregoing is prior art. All statements as to the date or representation as to the contents of these documents is based on subjective characterization of information available to the applicant, and does not constitute any admission as to the accuracy of the dates or contents of the documents.

SUMMARY OF THE INVENTION

The present invention therefore provides nematode neuromuscular junction GABA receptor complexes of the formula I $$A\text{-}B \qquad \text{Formula I}$$

wherein A an amino acid sequence selected from the group consisting of:
 (a) an amino acid sequence which is encoded by a nucleic acid sequence which has at least 80% identity to SEQ ID NO 2; wherein said identity can be determined using the DNAsis computer program and default parameters; and
 (b) an amino acid sequence which has at least 80% identity to SEQ ID NO 1; wherein said identity can be determined using the DNAsis computer program and default parameters; and wherein B is an amino acid sequence selected from the group consisting of:
 (a) an amino acid sequence which is encoded by a nucleic acid sequence which has at least 80% identity to SEQ ID NO 4; wherein said identity can be determined using the DNAsis computer program and default parameters; and
 (b) an amino acid sequence which has at least 80% identity to SEQ ID NO 3; wherein said identity can be determined using the DNAsis computer program and default parameters; and wherein A-B is a heteropentamer which comprises 1 to 4 A amino acid sequences and 1 to 4 B amino acid sequences.

Also provided are homopentamer nematode neuromuscular junction GABA receptor complexes of the formula II $$B_5 \qquad \text{Formula II}$$

wherein B is an amino acid sequence selected from the group consisting of:
 (a) an amino acid sequence which is encoded by a nucleic acid sequence which has at least 80% identity to SEQ ID NO 4; wherein said identity can be determined using the DNAsis computer program and default parameters; and (b) an amino acid sequence which has at least 80% identity to SEQ ID NO 3; wherein said identity can be determined using the DNAsis computer program and default parameters.

Also provided are nematode neuromuscular junction GABA receptor complex subunits, comprising an amino acid sequence selected from the group consisting of:
(a) an amino acid sequence which is encoded by a nucleic acid sequence which has at least 80% identity to SEQ ID NO 2; wherein said identity can be determined using the DNAsis computer program and default parameters; and
(b) an amino acid sequence which has at least 80% identity to SEQ ID NO 1; wherein said identity can be determined using the DNAsis computer program and default parameters.

Also provided are nematode neuromuscular junction GABA receptor complex subunits, comprising an amino acid sequence selected from the group consisting of:
(a) an amino acid sequence which is encoded by a nucleic acid sequence which has at least 80% identity to SEQ ID NO 4; wherein said identity can be determined using the DNAsis computer program and default parameters; and
(b) an amino acid sequence which has at least 80% identity to SEQ ID NO 3; wherein said identity can be determined using the DNAsis computer program and default parameters.

Also provided are nucleic acid compound which encodes a nematode neuromuscular junction GABA receptor complex subunits, comprising:
(a) a nucleic acid sequence which has at least 80% identity to SEQ ID NO 2; wherein said identity can be determined using the DNAsis computer program and default parameters;
(b) a nucleic acid which encodes an amino acid sequence which has at least 80% identity to SEQ ID NO 1; wherein said identity can be determined using the DNAsis computer program and default parameters;
(c) a nucleic acid sequence which is an allelic variant of SEQ ID NO 2; and
(d) a nucleic acid sequence fully complementary to a nucleic acid sequence selected from the group consisting of: a nucleic acid sequence of (a); a nucleic acid sequence of (b); and a nucleic acid sequence of (c).

Also provided are nucleic acid compounds which encode a nematode neuromuscular junction GABA receptor complex subunit, comprising a nucleic acid sequence selected from the group consisting of:
(a) a nucleic acid sequence which has at least 80% identity to SEQ ID NO 4; wherein said identity can be determined using the DNAsis computer program and default parameters;
(b) a nucleic acid which encodes an amino acid sequence which has at least 80% identity to SEQ ID NO 3; wherein said identity can be determined using the DNAsis computer program and default parameters;
(c) a nucleic acid sequence which is an allelic variant of SEQ ID NO 4; and
(d) a nucleic acid sequence fully complementary to a nucleic acid sequence selected from the group consisting of: a nucleic acid sequence of (a); a nucleic acid sequence of (b); and a nucleic acid sequence of (c).

Also provided are nucleic acid compounds which encode a nematode neuromuscular junction GABA receptor complex, comprising a first and second nucleic acid sequence, wherein said first nucleic acid sequence is selected from the group consisting of:
(a) a nucleic acid sequence which has at least 80% identity to SEQ ID NO 2; wherein said identity can be determined using the DNAsis computer program and default parameters;
(b) a nucleic acid which encodes an amino acid sequence which has at least 80% identity to SEQ ID NO 1; wherein said identity can be determined using the DNAsis computer program and default parameters;
(c) a nucleic acid sequence which is an allelic variant of SEQ ID NO 2; and
(d) a nucleic acid sequence which has at least 80% identity to SEQ ID NO 4; wherein said identity can be determined using the DNAsis computer program and default parameters;
(e) a nucleic acid which encodes an amino acid sequence which has at least 80% identity to SEQ ID NO 3; wherein said identity can be determined using the DNAsis computer program and default parameters;
(f) a nucleic acid sequence which is an allelic variant of SEQ ID NO 4; and wherein said second nucleic acid sequence is selected from the group consisting of:
(a) a nucleic acid sequence which has at least 80% identity to SEQ ID NO 4; wherein said identity can be determined using the DNAsis computer program and default parameters;
(b) a nucleic acid which encodes an amino acid sequence which has at least 80% identity to SEQ ID NO 3; wherein said identity can be determined using the DNAsis computer program and default parameters;
(c) a nucleic acid sequence which is an allelic variant of SEQ ID NO 4.

Moreover, there are provided isolated antibodies selective for a GABA receptor complexes of the present invention.

In addition, there are provided methods to determine a test substance's ability to interact with a nematode neuromuscular junction GABA receptor complex, comprising contacting a receptor complex of the present invention with a test substance and determining whether said test substance and said receptor complex interact.

Other methods include those to detect GABA receptors in a test sample, comprising: (a) immobilizing a test sample on a substrate; (b) contacting the test sample with an antibody of the present invention under conditions suitable for formation of a GABA receptor:antibody complex bound to the substrate; (c) removing non-bound material from the substrate under conditions that retain GABA:antibody complex binding to the substrate; and (d) detecting the presence of the GABA receptor:antibody complex.

Preferred isolated nucleic acid compounds of the present invention are those which comprise a nucleic acid sequence selected from the group consisting of: SEQ ID NO 2; SEQ ID NO 4; SEQ ID NO 6; SEQ ID NO 8; SEQ ID NO 10; and SEQ ID NO 12.

Preferred isolated amino acid compound of the present invention are those which comprise a nucleic acid sequence selected from the group consisting of: SEQ ID NO 1; SEQ ID NO 3, SEQ ID NO 5; SEQ ID NO 7; SEQ ID NO 9; SEQ ID NO 11.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

The genetic and physical map in the unc-49 region of chromosome III, and the structure of cosmid T21C12.

Figure 2A:
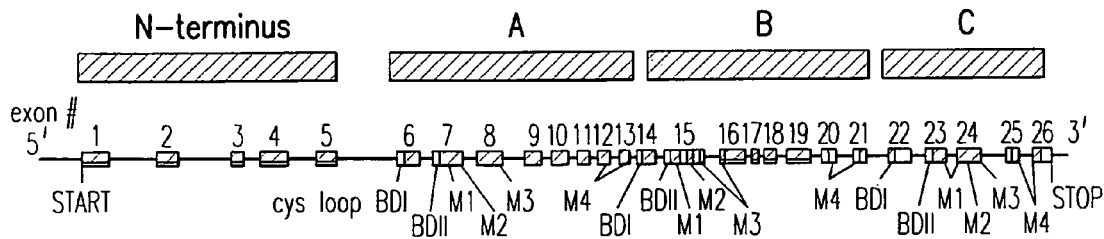
Figure 2B:
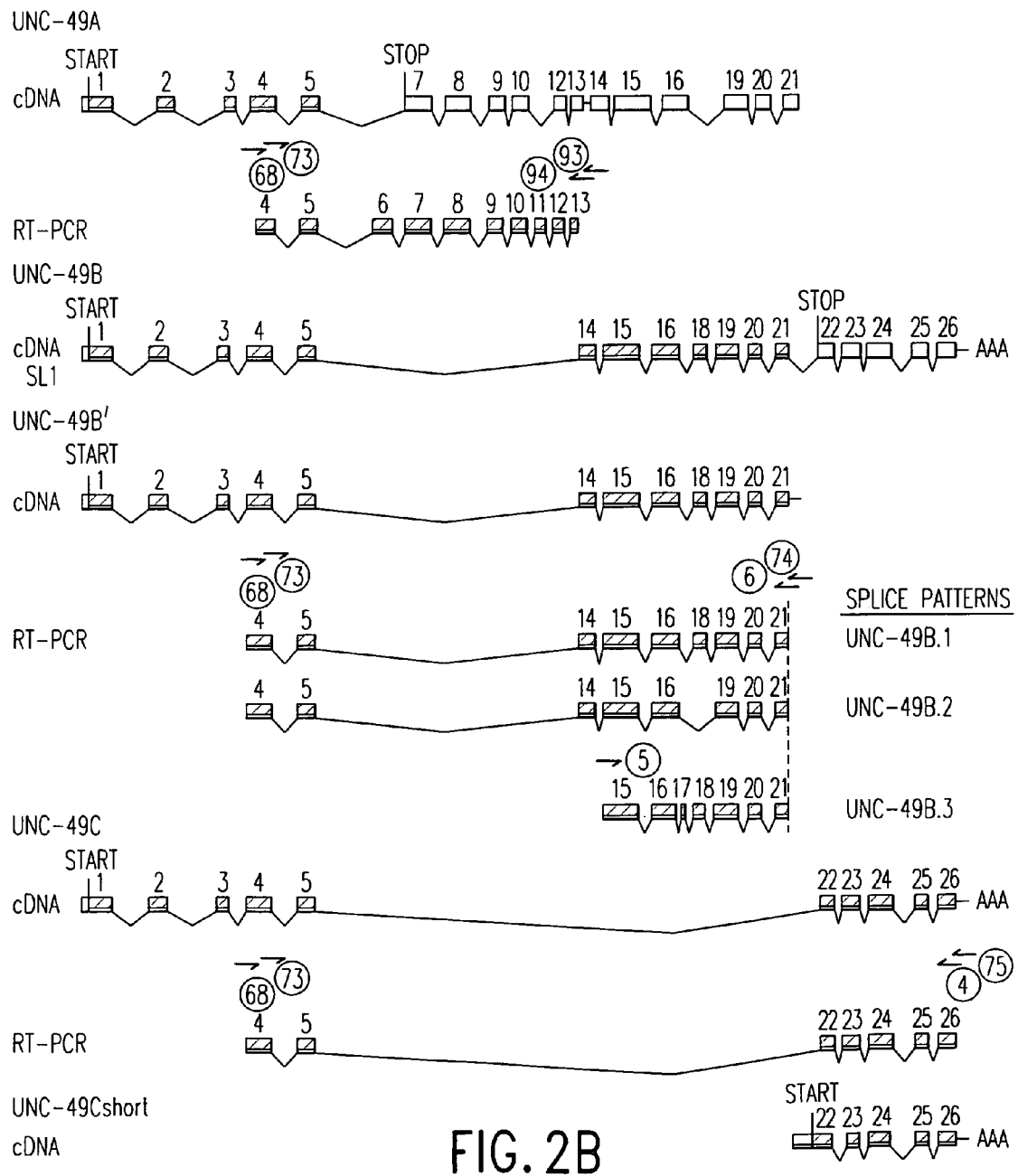
Figure 2C:
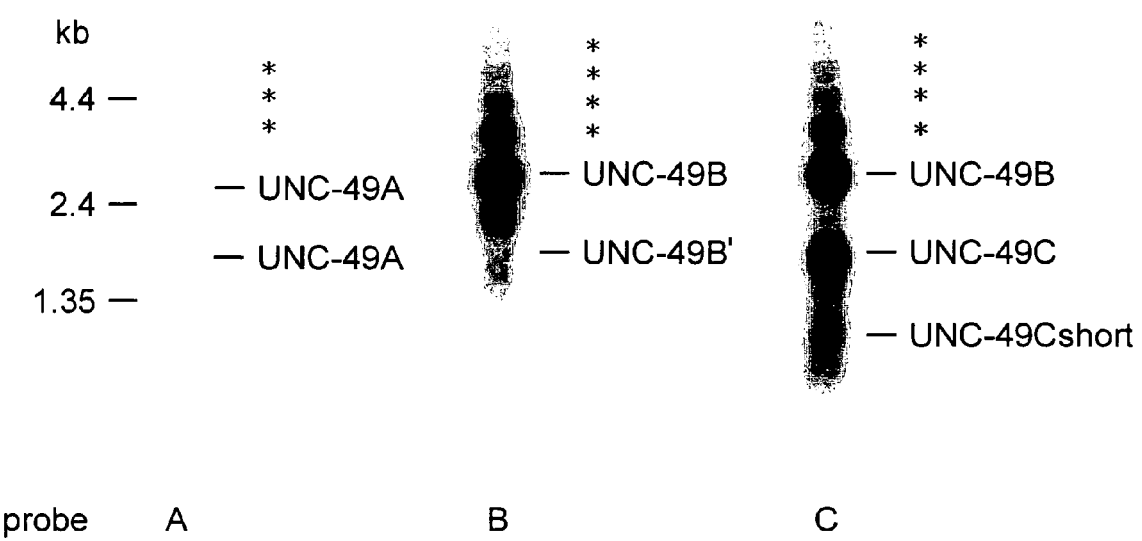

FIGS. 2A-C. unc-49 Produces Three Distinct GABA Receptor Subunits

A) Structure of the unc-49 locus showing the positions of conserved GABA receptor structural motifs. Domain structure of the locus is indicated by bars at top (see text). B) unc-49 mRNA structure. Transcripts were isolated both from cDNA libraries and from RT-PCT experiments. The short arrows and circled numbers represent PCR primers. Two superimposed primers (for example 68 and 73) represent a set of nested PCR primers. The shaded boxes represent coding exons and the open boxes represent untranslated regions. The SL1 splice leader was found at the 5' ends of the mRNA species where indicated. C) Northern analysis. The probes, indicated below each lane, correspond to the carboxy-terminal repeats. Labels to the right of each lane indicate the probable identity of each band. In the UNC-49C lane, the UNC-49B mRNA is visible because it contains the UNC-49C open reading frame in its 3' UTR. Asterisks indicate higher molecular weight bands which may correspond to partially-spliced unc-49 pre-mRNA. All lanes were exposed for the same length of time.

Figure 3:
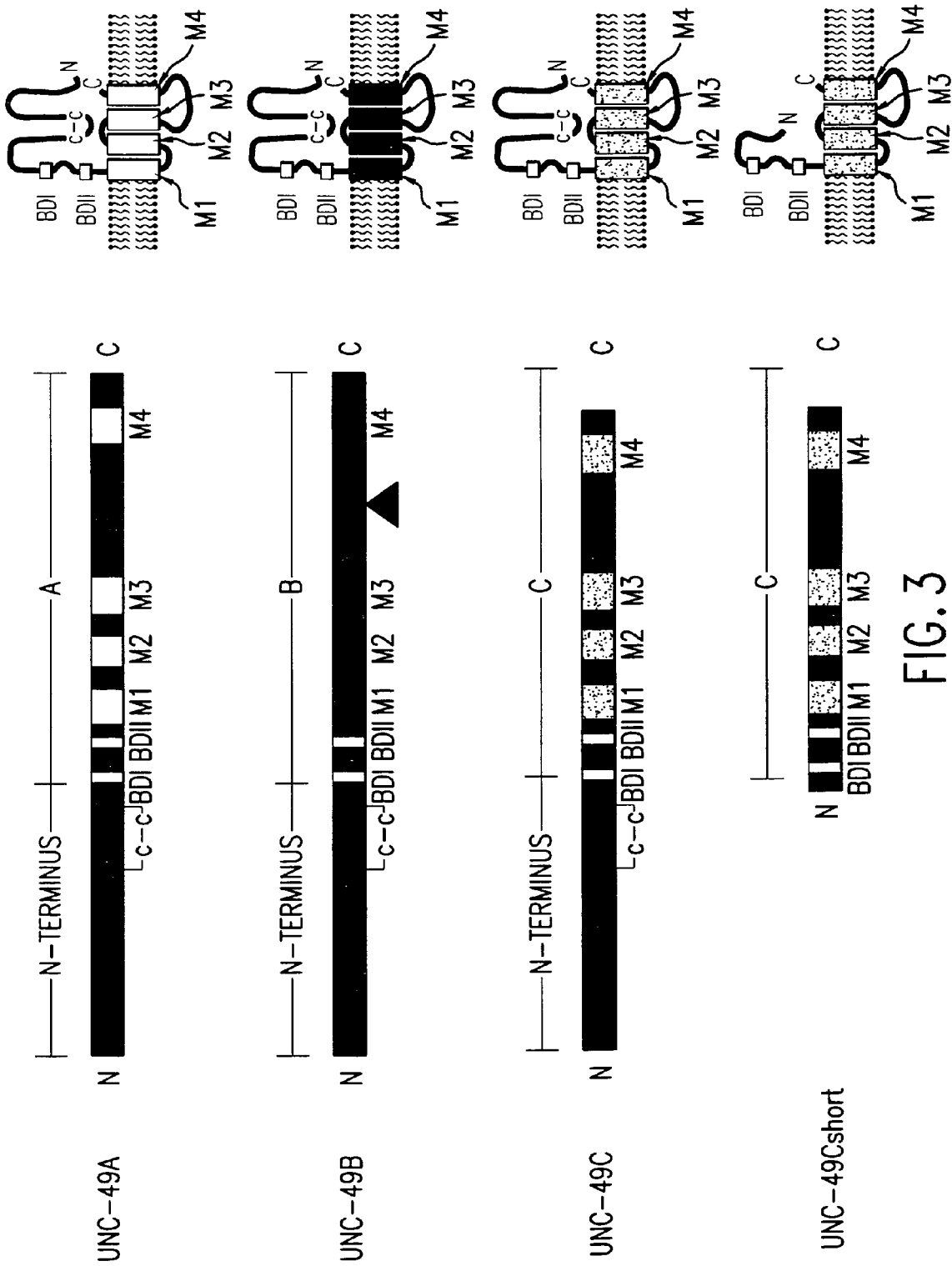

FIG. 3. Structural Overlap Among unc-49 Subunits

UNC-49A, UNC-49B, and UNC-49C are identical over the amino-terminal 40% of their length, but contain different putative GABA binding domains and transmembrane domains. Left panel shows an alignment of each subunit mRNA (bar at top indicates origin of exons encoding each portion). Triangle indicates the position of the alternative splice site in UNC-49B. Note that the UNC-49Cshort is identical to the unique carboxy-terminal portion of UNC49C, but lacks the entire amino terminus common to the other subunits; in its place are four unique N-terminal amino acids (gray box). Right panel depicts the predicted unc-49 subunit proteins. Also indicated is the genomic origin of the exons encoding each segment (see FIG. 2).

Figure 4A:
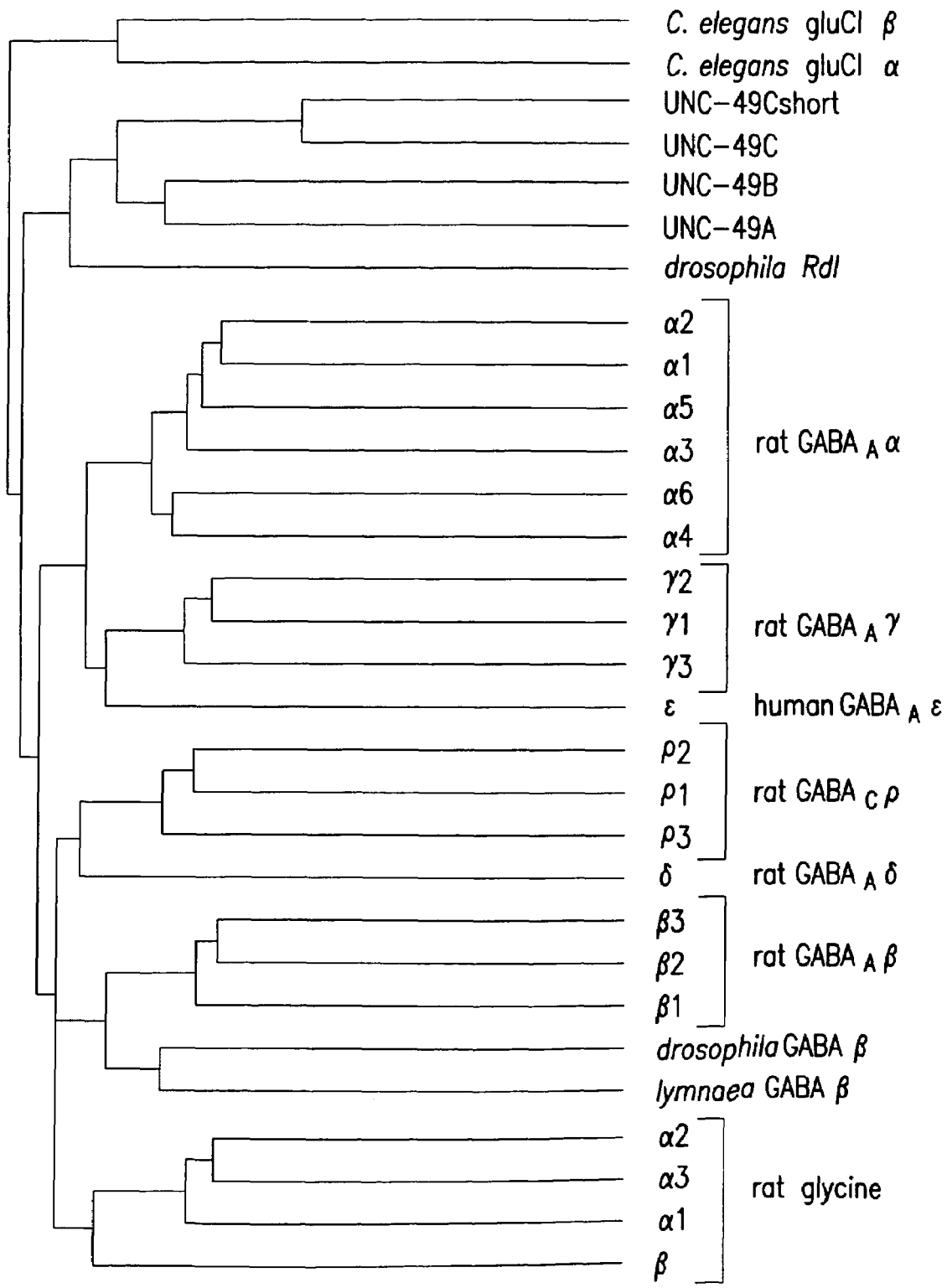

FIGS. 4A-C. GABA Receptor Family

A) Dendogram of GABA receptor subunits. The three unc-49 subunits do not correspond to any of the vertebrate classes of $GABA_A$ receptor subunits. Alignments were performed using the Pileup program in the Genetics Computer Group analysis package. B) Sequence alignment of unc-49 subunits. Residues in black boxes are conserved in all members of a set of seven representative non-C.elegans GABA receptor subunits, and residues in gray boxes are conserved in six out of seven members of this set (see Experimental Procedures). The rat $\beta 2$ $GABA_A$ and Drosophila RDL receptor subunits are included for comparison. Residues conserved in all members of the ligand-gated ion channel superfamily are indicated by asterisks. Dashed line indicates the disulfide bonded loop motif ($CX_{13}C$) conserved in all ligand-gated ion channel subunits. Bars labeled BDI and BDII indicate putative GABA binding domains and bars labeled M1-M4 indicate membrane-spanning domains. Residues in BDI and BDII which are functionally important in the ρ and β GABA receptor subunits, but are divergent in the C. elegans subunits, are denoted by # and $, respectively. Glutamic acid residue in UNC-49C M2 is denoted by @. Arrowheads indicate predicted sites of signal peptide cleavage for UNC-49B and UNC-49C and the rat β32 subunit. Residues are numbered from the predicted start of translation except for the rat β32 subunit, which is numbered from the predicted signal peptide cleavage site according to convention. UNC-49B is numbered according to the UNC-49B.1 sequence. C) Residues comprising the M3-M4 intraceullular loops of the unc-49 encoded subunits. Sequences of the three UNC-49B isoforms are also shown. Intraceullular loop sequences have not been aligned. Symbols above each intracellular loop indicate potential regulatory phosphorylation sites (A indicates a PKA site, C indicates a PKC site, and * indicates a CKII site).

Figure 5A:
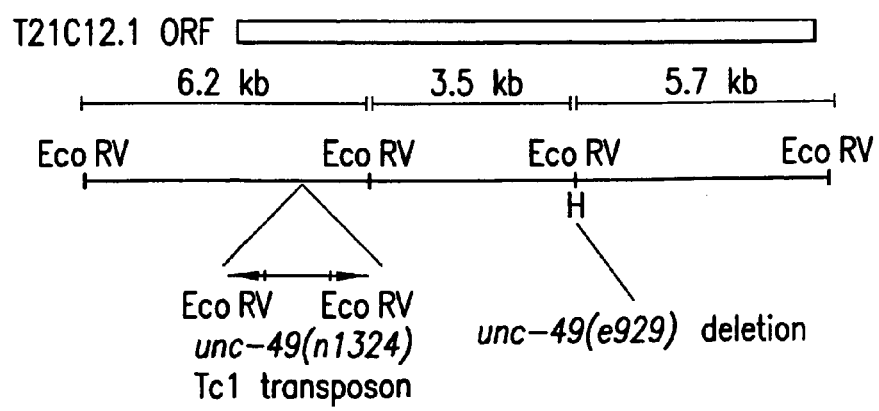

FIGS. 5A-C. All unc-49 Mutations Affect UNC-49B

A) Upper panel, Southern blot of EcoRV-digested genomic DNA probed with T21C12 insert DNA. Numbers at right indicate the positions of DNA size standards. Lower panel, a restriction map of the genomic DNA encompassing unc-49. Positions of the polymorphisms observed in unc-49 (n1324) and unc-49(e929) are shown beneath the restriction map. Shaded bar indicates the T21C12.1 open reading frame. B) Positions of mutations in the unc-49 alleles are shown. E-382, e-468, e641, and e929 affect only UNC-49B whereas e407, n1324, and n2392 affect UNC-49A, UNC-49B and UNC-49C. Bars at top represent unc-49 domains. C) Summary of unc-49 mutations.

Figure 6B:
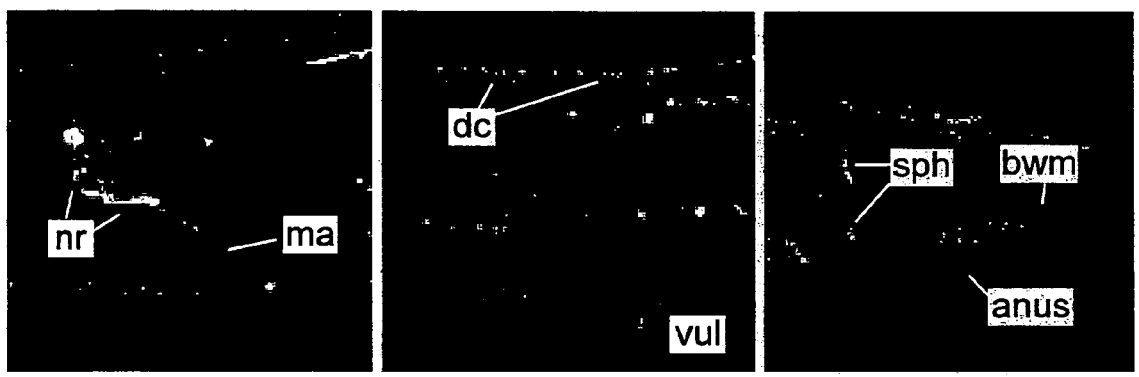
Figure 6C:
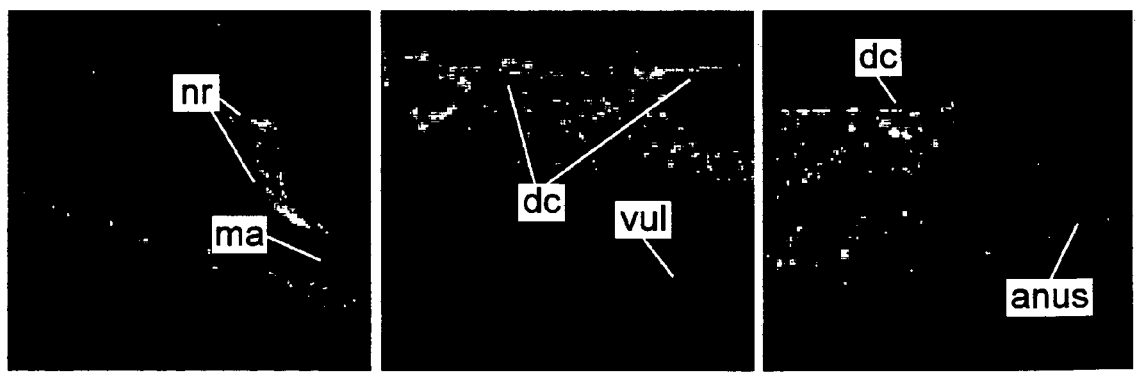

FIGS. 6A-C. UNC-49B and UNC-49C are Co-localized

A) Structure of UNC-49::GFP transgenes. The left panel shows the site at which GFP was inserted, in frame, into the unc-49 rescuing fragment. Vertical bars represent transmembrane domains. Right panel shows the subunits which are produced by the transgene. 'GFP' indicates subunits tagged with GFP, + indicates wild-type subunits, − indicates inactivated subunits. B, C) Confocal images of UNC-49B::GFP and UNC-49C::GFP transgenic worms. In the head (left panels), both constructs produce GFP fluorescence in the nerve ring (nr) and head muscle arms (ma). In the vicinity of the vulva (vul, middle panels), both constructs produce bright fluorescence in the dorsal nerve cord (dc). Fluorescence in the ventral nerve cord was not clearly visible in these specimens because of their orientation on the miscoscope slide. Bright spots in the middle of the animal are autofluorescent gut granules. In the tail, the UNC-49B::GFP construct produces fluorescence in the sphincter muscle (sph) while the UNC-49C:GFP construct does not (right panels). This individual showed some GFP fluorescence in the body wall muscles in the tail (bwm).

Figure 7A:
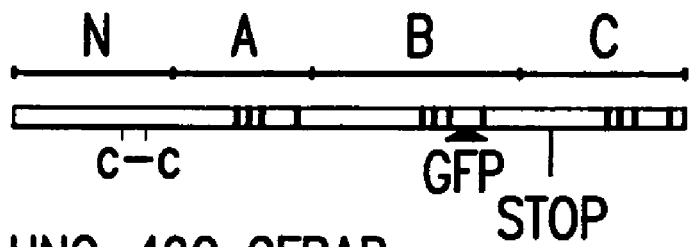
Figure 7A:
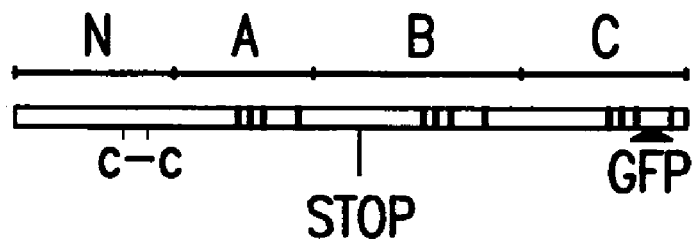
Figure 7B:
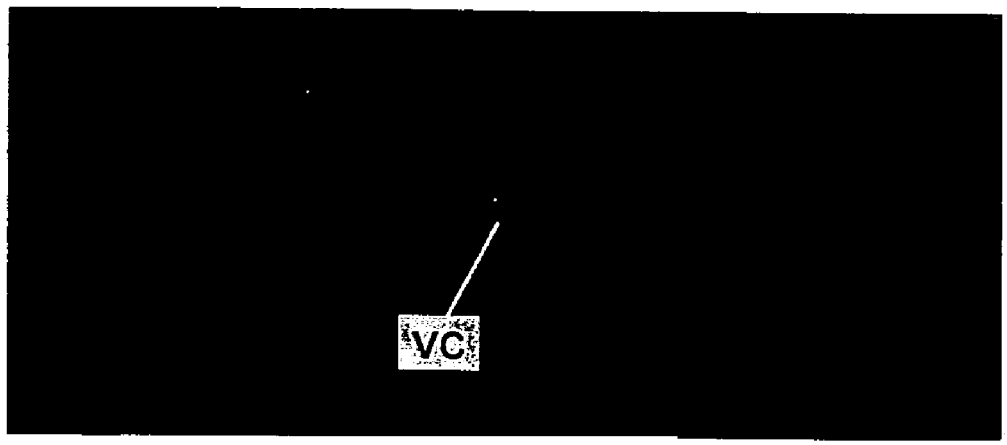
Figure 7C:

FIGS. 7A-C. UNC-49B and UNC-49C Associate at the Neuromuscular Junction

A) Structure of the modified UNC-49::GFP transgenes. Left panel shows transgene structure and right panel shows the subunits produced by each transgene, as in FIG. 6. B) Epifluorescent image of UNC-49B::GFP expressed in the absence of UNC-49C. Fluorescence was visible along the ventral nerve cord (vc), suggesting proper synaptic localization of UNC-49B::GFP. C) UNC-49C::GFP expressed in the absence of UNC-49B. Muscle membranes and muscle arms (MA) are fluorescent, but no enrichment of fluorescence is observed in the ventral nerve cord (vc) indicating that UNC-49C:GFP is not synaptically localized.

Figure 8A:
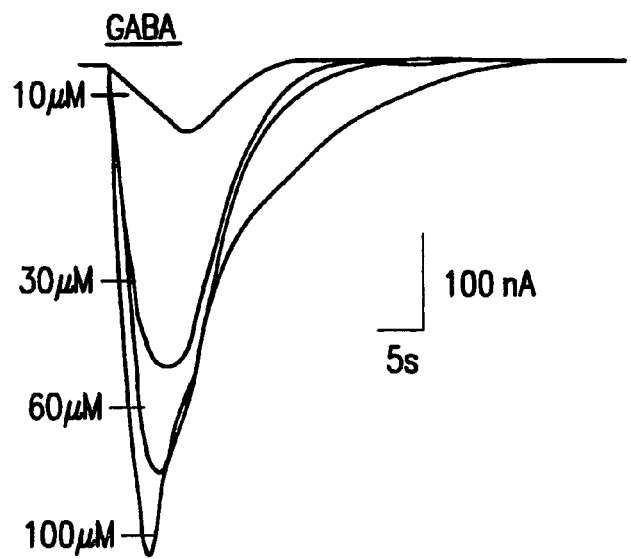
Figure 8B:
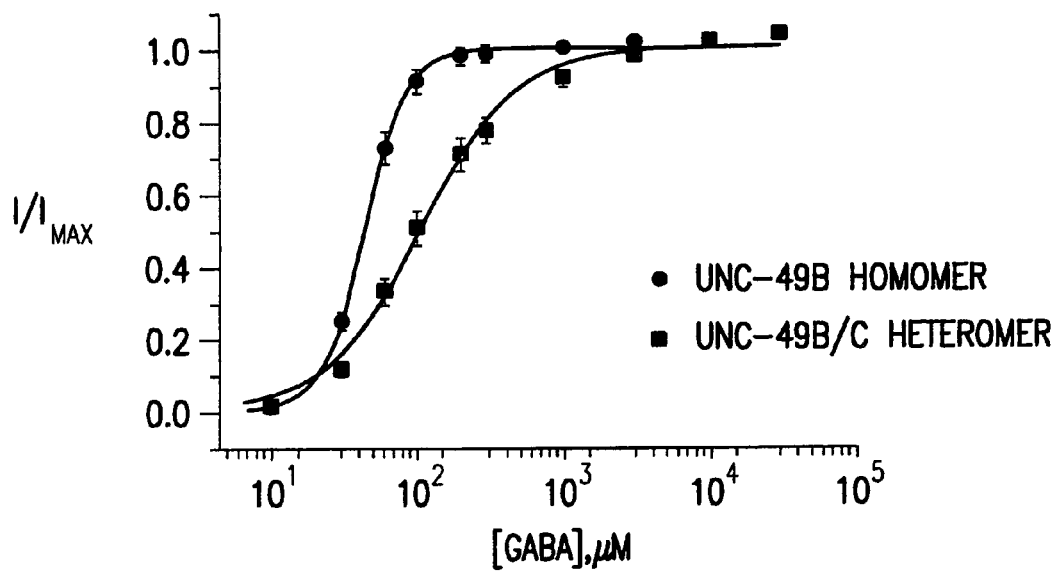
Figure 8C:
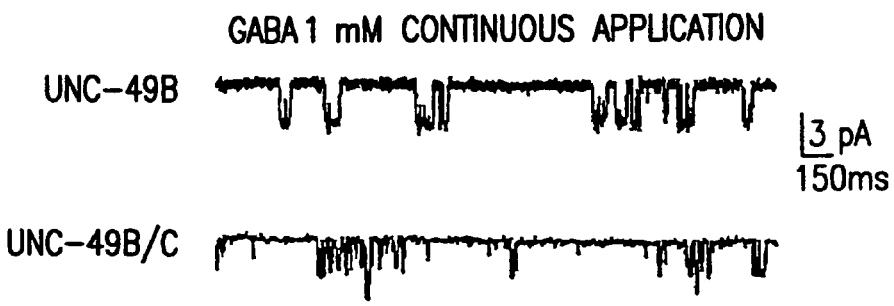

FIGS. 8A-C. UNC-49B and UNC-49C Co-assemble in Heterologous Cells

A) Response of a representative UNC-49B.1-injected oocyte to 10 sec pulses of GABA at 10 µM, 30 µM, 60 µM and 100 µM. B) GABA dose response curves obtained from *Xenopus* oocytes injected with UNC-49B (circles) or UNC-49B+UNC-49C (squares). Error bars represent standard error of the mean. C) Signle-channel recordings from HEK-293 cells expressing UNC-49B alone (top trace) or UNC-49B+UNC-49C (bottom trace).

Figure 9:
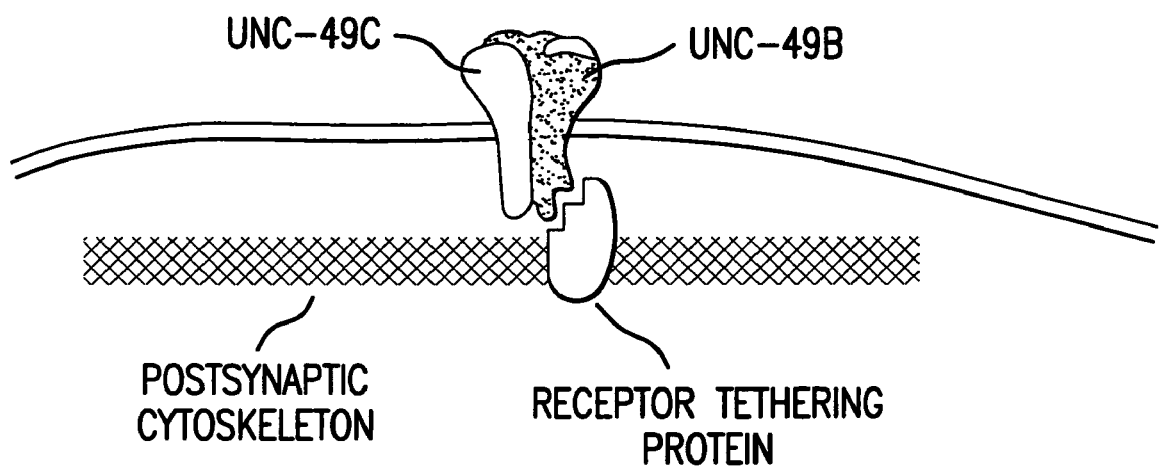

FIG. 9. Proposed Interaction of UNC-49B and UNC-49C at the Synapse

UNC-49B and UNC-49C form a heteromeric GABA receptor which is tethered at the synapse by the binding of UNC-49B with a cytoskeletal component of the postsynaptic specialization.

BRIEF DESCRIPTION OF THE SEQUENCE LISTING

| SEQ ID NO | Sequence Description |
|---|---|
| 1 | unc 49-C amino acid sequence |
| 2 | unc 49-C DNA sequence |
| 3 | unc 49-B amino acid sequence |
| 4 | unc 49-B DNA sequence |
| 5 | unc 49-A amino acid sequence |
| 6 | unc 49-A DNA sequence |
| 7 | unc 49-B2 amino acid sequence |
| 8 | unc 49-B2 DNA sequence |
| 9 | unc 49-B3 amino acid sequence |
| 10 | unc 49-B3 DNA sequence |
| 11 | unc 49-Cshort amino acid sequence |
| 12 | unc 49-Cshort DNA sequence |

DETAILED DESCRIPTION OF THE INVENTION

The present invention therefore provides nematode neuromuscular junction GABA receptor complexes of the formula I $$A\text{-}B \qquad \text{Formula I}$$

wherein A an amino acid sequence selected from the group consisting of:
(a) an amino acid sequence which is encoded by a nucleic acid sequence which has at least 80% identity to SEQ ID NO 2; wherein said identity can be determined using the DNAsis computer program and default parameters; and
(b) an amino acid sequence which has at least 80% identity to SEQ ID NO 1; wherein said identity can be determined using the DNAsis computer program and default parameters; and wherein B is an amino acid sequence selected from the group consisting of:
(a) an amino acid sequence which is encoded by a nucleic acid sequence which has at least 80% identity to SEQ ID NO 4; wherein said identity can be determined using the DNAsis computer program and default parameters; and
(b) an amino acid sequence which has at least 80% identity to SEQ ID NO 3; wherein said identity can be determined using the DNAsis computer program and default parameters; and wherein A-B is a heteropentamer which comprises 1 to 4 A amino acid sequences and 1 to 4 B amino acid sequences. For instance, A-B may comprise 4 A amino acid sequences, and 1 B amino acid sequence, or A-B may comprise 3 A amino acid sequences, and 2 B amino acid sequences, or A-B may comprise 2 A amino acid sequences, and 3 B amino acid sequences, or A-B may comprise 1 A amino acid sequence, and 4 B amino acid sequences. So long as the amino acid sequences form a heteropentamer receptor complex which, given the proper conditions, will allow chloride ion conductance, the complex is within the scope of the present invention.

Also provided are homopentamer nematode neuromuscular junction GABA receptor complexes of the formula II $$B_5 \qquad \text{Formula II}$$

wherein B is an amino acid sequence selected from the group consisting of:
(a) an amino acid sequence which is encoded by a nucleic acid sequence which has at least 80% identity to SEQ ID NO 4; wherein said identity can be determined using the DNAsis computer program and default parameters; and
(b) an amino acid sequence which has at least 80% identity to SEQ ID NO 3; wherein said identity can be determined using the DNAsis computer program and default parameters.

Also provided are nematode neuromuscular junction GABA receptor complex subunits, comprising an amino acid sequence selected from the group consisting of:
(a) an amino acid sequence which is encoded by a nucleic acid sequence which has at least 80% identity to SEQ ID NO 2; wherein said identity can be determined using the DNAsis computer program and default parameters; and
(b) an amino acid sequence which has at least 80% identity to SEQ ID NO 1; wherein said identity can be determined using the DNAsis computer program and default parameters.

Also provided are nematode neuromuscular junction GABA receptor complex subunits, comprising an amino acid sequence selected from the group consisting of:
(a) an amino acid sequence which is encoded by a nucleic acid sequence which has at least 80% identity to SEQ ID NO 4; wherein said identity can be determined using the DNAsis computer program and default parameters; and
(b) an amino acid sequence which has at least 80% identity to SEQ ID NO 3; wherein said identity can be determined using the DNAsis computer program and default parameters.

Preferred isolated amino acid compound of the present invention are those which comprise a nucleic acid sequence selected from the group consisting of: SEQ ID NO 1; SEQ ID NO 3, SEQ ID NO 5; SEQ ID NO 7; SEQ ID NO 9; and SEQ ID NO 11.

Fragments that are preferred are those which are binding sites of the proteins or protein complexes. For example, the following are preferred: drug modulatory sites which have been mapped to M1, M2, M2-M3 loop, and M3, and the amino terminal sequences.

Proteins which would result from expression of the nucleic acid molecules herein disclosed are preferred, with the proteins which would result from expression of the exemplified compounds being most preferred. It is understood that proteins which would result from expression of allelic variants of the exemplified sequences, as well as proteins which would result from the expression of nucleic acid molecules which hybridize under stringent hybridization conditions to the nucleic acid molecules exemplified are within the scope of the present invention as well.

More preferred proteins of the present invention include proteins comprising amino acid sequences that are at least about 70%, even more preferably at least about 75%, even more preferably at least about 80%, even more preferably at least about 85%, even more preferably at least about 90%, and even more preferably at least about 95%, identical to amino acid sequence exemplified herein. Percent identity can be determined use of well-known methods.

There are also provided recombinant cells comprising the proteins herein described.

Also provided are protein homologs of the present invention. Protein homologs can be the result of natural allelic variation or natural mutation. Protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

One embodiment of the present invention is a fusion protein that includes a protein domain attached to one or more fusion segments. Suitable fusion segments for use with the present invention include, but are not limited to, segments that can: enhance a protein's stability and/or assist purification (e.g., by affinity chromatography). A suitable fusion segment can be a domain of any size that has the desired function (e.g., imparts increased stability, imparts increased immunogenicity to a protein, and/or simplifies purification of a protein). Fusion proteins are preferably produced by culturing a recombinant cell transformed with a fusion nucleic acid molecule that encodes a protein including the fusion segment attached to either the carboxyl and/or amino terminal end. Preferred fusion segments include a metal binding domain (e.g., a poly-histidine segment); an immunoglobulin binding domain (e.g., Protein A; Protein G; T cell; B cell; complement protein antibody-binding domains); a sugar binding domain (e.g., a maltose binding domain); a "tag" domain (e.g., at least a portion of β-galactosidase, a strep tag peptide, other domains that can be purified using compounds that bind to the domain, such as monoclonal antibodies); and/or a linker and enzyme domain (e.g., alkaline phosphatase domain connected to a protein by a linker). More preferred fusion segments include metal binding domains, such as a poly-histidine segment; a maltose binding domain; a strep tag peptide; and a phage T7 S10 peptide.

In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit few impurities.

In addition, recombinant protein can be separated from other cellular proteins by use of an immunoaffinity column made with monoclonal or polyclonal antibodies specific for herein protein, or polypeptide fragments of herein protein.

Also provided are nucleic acid compound which encodes a nematode neuromuscular junction GABA receptor complex subunits, comprising:
(a) a nucleic acid sequence which has at least 80% identity to SEQ ID NO 2; wherein said identity can be determined using the DNAsis computer program and default parameters;
(b) a nucleic acid which encodes an amino acid sequence which has at least 80% identity to SEQ ID NO 1; wherein said identity can be determined using the DNAsis computer program and default parameters;
(c) a nucleic acid sequence which is an allelic variant of SEQ ID NO 2; and
(d) a nucleic acid sequence fully complementary to a nucleic acid sequence selected from the group consisting of: a nucleic acid sequence of (a); a nucleic acid sequence of (b); and a nucleic acid sequence of (c).

Also provided are nucleic acid compounds which encode a nematode neuromuscular junction GABA receptor complex subunit, comprising a nucleic acid sequence selected from the group consisting of:
(a) a nucleic acid sequence which has at least 80% identity to SEQ ID NO 4; wherein said identity can be determined using the DNAsis computer program and default parameters;
(b) a nucleic acid which encodes an amino acid sequence which has at least 80% identity to SEQ ID NO 3; wherein said identity can be determined using the DNAsis computer program and default parameters;
(c) a nucleic acid sequence which is an allelic variant of SEQ ID NO 4; and
(d) a nucleic acid sequence fully complementary to a nucleic acid sequence selected from the group consisting of: a nucleic acid sequence of (a); a nucleic acid sequence of (b); and a nucleic acid sequence of (c).

Also provided are nucleic acid compounds which encode a nematode neuromuscular junction GABA receptor complex, comprising a first and second nucleic acid sequence, wherein said first nucleic acid sequence is selected from the group consisting of:

(a) a nucleic acid sequence which has at least 80% identity to SEQ ID NO 2; wherein said identity can be determined using the DNAsis computer program and default parameters;
(b) a nucleic acid which encodes an amino acid sequence which has at least 80% identity to SEQ ID NO 1; wherein said identity can be determined using the DNAsis computer program and default parameters;
(c) a nucleic acid sequence which is an allelic variant of SEQ ID NO 2; and
(d) a nucleic acid sequence which has at least 80% identity to SEQ ID NO 4; wherein said identity can be determined using the DNAsis computer program and default parameters;
(e) a nucleic acid which encodes an amino acid sequence which has at least 80% identity to SEQ ID NO 3; wherein said identity can be determined using the DNAsis computer program and default parameters;
(f) a nucleic acid sequence which is an allelic variant of SEQ ID NO 4; and wherein said second nucleic acid sequence is selected from the group consisting of:

(a) a nucleic acid sequence which has at least 80% identity to SEQ ID NO 4; wherein said identity can be determined using the DNAsis computer program and default parameters;
(b) a nucleic acid which encodes an amino acid sequence which has at least 80% identity to SEQ ID NO 3; wherein said identity can be determined using the DNAsis computer program and default parameters;
(c) a nucleic acid sequence which is an allelic variant of SEQ ID NO 4.

Preferred isolated nucleic acid compound of the present invention are those which comprise a nucleic acid sequence selected from the group consisting of: SEQ ID NO 2; SEQ ID NO 4; and SEQ ID NO 6; SEQ ID NO 8; SEQ ID NO 10; SEQ ID NO 12.

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNA-SIS™ (available from Hitachi Software, San Bruno, Calif.) and MACVECTOR™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters. A nucleic acid sequence of the present invention may have at least 75%, preferably 80%, and most preferably 95% sequence identity with a nucleic acid molecule in the sequence listing.

Additional preferred nucleic acid molecules of the present invention include an isolated nucleic acid molecule which is at least about 50 nucleotides, or at least about 150 nucleotides, comprising a nucleic acid sequence that is preferably at least about 45% identical, more preferably about 50% identical, more preferably about 55% identical, more preferably about 60% identical, more preferably about 65% identical, more preferably about 70% identical, more preferably about 75% identical, more preferably about 80% identical, more preferably about 85% identical, more preferably about 90% identical and even more preferably about 95% identical to a nucleic acid sequence selected from the exemplified sequences. Also preferred are fragments of any of such nucleic acid molecules. Percent identity may be determined using the Compare function by maximum matching within the program DNAsis Version 2.1 using default parameters.

The present invention also comprises expression vectors and recombinant cells comprising the present nucleic acid molecules. Also provided are fusion proteins constructed using the present nucleic acid compounds.

Included within the scope of the present invention, with particular regard to the nucleic acids above, are allelic variants, degenerate sequences and homologues. Allelic variants are well known to those skilled in the art and would be expected to be found within a given diploid organism and/or among a group of organisms. The present invention also includes variants due to laboratory manipulation, such as, but not limited to, variants produced during polymerase chain reaction amplification or site-directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide.

Knowing the nucleic acid sequences of certain nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain nucleic acid molecules from other species. Such nucleic acid molecules can be obtained in a variety of ways including screening appropriate expression libraries with antibodies of the present invention; traditional cloning techniques using oligonucleotide probes of the present invention to screen appropriate libraries of DNA; and PCR amplification of appropriate libraries or DNA using oligonucleotide primers of the present invention. Preferred libraries to screen or from which to amplify nucleic acid molecules include protozoal or mycoplasma libraries as well as genomic DNA libraries. Similarly, preferred DNA sources to screen or from which to amplify nucleic acid molecules include adult cDNA and genomic DNA. Techniques to clone and amplify genes are disclosed, for example, in Sambrook et al., ibid.

The translation of the RNA into a peptide or a protein will result in the production of at least a portion of the protein which can be identified, for example, by the activity of protein or by immunological reactivity with an anti-protein antibody. In this method, pools of mRNA isolated from protein-producing cells can be analyzed for the presence of an RNA which encodes at least a portion of the protein. Further fractionation of the RNA pool can be done to purify the herein protein RNA from non-protein RNA. The peptide or protein produced by this method may be analyzed to provide amino acid sequences which in turn are used to provide primers for production of cDNA, or the RNA used for translation can be analyzed to provide nucleotide sequences encoding herein proteins and produce probes for the production of cDNA. These methods are known in the art and can be found in, for example, Sambrook, J., Fritsch, E. F., Maniatis, T. in *Molecular Cloning: A Laboratory Manual, Second Edition*, Cold Spring Harbor Laboratory Press, Cold Spring Harbor, N.Y. 1989.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is, nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of the nucleic acid molecules of the present invention.

One type of recombinant vector, referred to herein as a recombinant molecule, comprises a nucleic acid molecule of the present invention operatively linked to an expression vector. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally-occurring transcription control sequences naturally associated with humans. The present invention also comprises expression vectors comprising a nucleic acid molecule described herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Also provided by the present invention are recombinant cells transformed with a nucleic acid described herein.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacterial, yeast, parasite, insect and mammalian cells.

A recombinant cell is preferably produced by transforming a host cell with one or more recombinant molecules, each comprising one or more nucleic acid molecules of the present invention operatively linked to an expression vector containing one or more transcription control sequences. The phrase "operatively linked" refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein.

Moreover, there are provided isolated antibodies selective for a GABA receptor complexes of the present invention.

The present invention also includes isolated (i.e., removed from their natural milieu) antibodies that selectively bind to a portion of the protein of the present invention or a mimeotope thereof. Binding can be measured using a variety of methods standard in the art including enzyme immunoassays (e.g., ELISA), immunoblot assays, etc.; see, for example, Sambrook et al., ibid. An anti-herein protein antibody preferably selectively binds to herein protein in such a way as to reduce the activity of that protein. These antibodies may be admixed or conjugated with additional materials, such as cytotic agents or other antibody fragments.

Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce proteins of the present invention.

In another embodiment, therapeutic compositions such as the herein described antibodies, nucleic acid compounds and/or the amino acid compounds (preferably for immunotherapy/vaccines) can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresols, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

Administration of the compounds can be by a variety of routes known to those skilled in the art including, but not limited to, subcutaneous, intradermal, intravenous, intranasal, oral, transdermal, intramuscular routes and other parenteral routes.

In one embodiment of the present methods, a therapeutic composition can include an adjuvant. Adjuvants are agents that are capable of increasing the immune response of an animal to a specific antigen. Protein adjuvants of the present invention can be delivered in the form of the protein themselves or of nucleic acid molecules encoding such proteins using the methods described herein.

In another embodiment of the present methods, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

Another embodiment of the present methods is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels in the animal. The therapeutic composition is preferably released over a period of time ranging from about 1 day to about 12 months, and include release over a 2, 3, 4, 5, 6, 7 day through a 30 day time period.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting (i.e., preventing or treating) an animal from disease when administered one or more times over a suitable time period. The need for additional administrations of a therapeutic composition can be determined by one of skill in the art in accordance with the given condition of a patient.

Pharmaceutically useful compositions comprising herein proteins, may be formulated according to known methods such as by the admixture of a pharmaceutically acceptable carrier, or by modification with additional chemical moieties so as to form a chemical derivative. Examples of such carriers, modifications and methods of formulation may be found in Remington's Pharmaceutical Sciences. To form a pharmaceutically acceptable composition suitable for effective administration, such compositions will contain an effective amount of the protein or DNA.

The present invention also has the objective of providing suitable topical, oral, systemic and parenteral formulations of the pharmaceutical compounds herein provided. The formulations can be administered in a wide variety of therapeutic dosage forms in conventional vehicles for administration. For example, the compounds can be formulated for oral administration in the form of tablets, capsules (each including timed release and sustained release formulations), pills, powders, granules, elixirs, tinctures, solutions, suspensions, syrups and emulsions, or by injection. Likewise, they may also be administered intravenously (both bolus and infusion), during angioplasty/catheterization, intraperitoneally, subcutaneously, topically with or without occlusion, or intramuscularly, all using forms well known to those of ordinary skill in the pharmaceutical arts.

A molecule can be combined with a buffer in which the molecule is solubilized, and/or with a carrier. Suitable buffers and carriers are known to those skilled in the art. Examples of suitable buffers include any buffer in which a molecule can function to inhibit its target enzyme(s), such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin.

For instance, for oral administration in the form of a tablet or capsule, the active drug component can be combined with an oral, non-toxic pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions formulations. The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

In addition, there are provided methods to determine a test substance's ability to interact with a nematode neuromuscular junction GABA receptor complex, comprising contacting a receptor complex of the present invention with a test substance and determining whether said test substance and said receptor complex interact.

Other methods include those to detect GABA receptors in a test sample, comprising: (a) immobilizing a test sample on a substrate; (b) contacting the test sample with an antibody of the present invention under conditions suitable for formation of a GABA receptor:antibody complex bound to the substrate; (c) removing non-bound material from the substrate under conditions that retain GABA:antibody complex binding to the substrate; and (d) detecting the presence of the GABA receptor:antibody complex.

As used herein, the term "contacting" refers to combining or mixing ingredients, as all of those terms are known in the art. Conditions suitable to form a complex; such conditions (e.g., appropriate concentrations, buffers, temperatures, reaction times) as well as methods to optimize such conditions are known to those skilled in the art, and examples are disclosed herein. Complex formation conditions are also disclosed in the Examples.

In one embodiment, a test substance of the present method includes a biological sample from an animal. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, milk and feces.

Detection can be accomplished in a variety of ways including, but not limited to use of one or more of the following assays: an enzyme-linked immunoassay, a radioimmunoassay, a fluorescence immunoassay, a chemiluminescent assay, a lateral flow assay, an agglutination assay, a particulate-based assay (e.g., using particulates such as, but not limited to, magnetic particles or plastic polymers, such as latex or polystyrene beads), an immunoprecipitation assay, a BioCore™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. In other assays, conjugation (i.e., attachment) of a detectable marker or to a reagent that selectively binds to the protein or nucleic acid or to the molecule being detected (described in more detail below) aids in detection. Examples of detectable markers include, but are not limited to, a radioactive label, an enzyme, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin available from Pierce, Rockford, Ill.). According to the present invention, a detectable marker can be connected to a molecule using, for example, chemical conjugation or recombinant DNA technology (e.g., connection of a fusion segment such as that described herein for a metal binding domain; an immunoglobulin binding; a sugar binding domain; and a "tag" domain).

In one embodiment, the method can be accomplished in solution. In another embodiment, one or or more ingredients are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker.

A preferred method to detect is via generation or inhibition of an electrical, preferably a chloride ion, current in a frog oocyte assay. The examples, as well as many journal articles and textbooks, describe frog oocyte assays of this nature.

The following examples illustrate the present invention without, however, limiting it. It is to be noted that the Examples include a number of molecular biology, microbiology, immunology and biochemistry techniques considered to be known to those skilled in the art. Disclosure of such techniques can be found, for example, in Sambrook et al., ibid., and related references.

EXAMPLE 1

Experimental Procedures

C. elegans Strains unc-49 strains and corresponding alleles used in this study are as follows: CB382: unc-49(e382), CB407: unc-49 (e407), EG1232: unc-49(e468), CB641: unc-49(e641), CB929: unc-49(e929), MT2976: unc-49(n1324), MT3123: unc-49(n1324n1345), MT6224: unc-49(n2392). MT6225: unc-49(n2393) is likely to be a re-isolate of n2392 since the mutations are identical. The n1324 allele was isolated from MT2879, in which Tc1 transposons are active. The above list represents all unc-49 alleles isolated to date.

C. elegans Transformation

Transformation was performed by microinjection of plasmid and cosmid DNA into the C. elegans germline according to Mello, C. C., Kramer, J. M., Stinchcomb, D., and Ambros, V. (1991). Efficient gene transfer in C. elegans: extrachromosomal maintenance and integration of transforming sequences. EMBO J. 10, 3959-3970. T21C12 and T21C12ΔMlu were injected at 80 ng/μl into unc-49(e382); lin-15(n765ts). pEK1, a plasmid that contains the wild-type lin-15 gene (S. G. Clark and X. Lu, personal communication; Clark, S. G., Lu, X., and Horvitz, H. R. (1994). The Caenorhabditis elegans locus lin-15, a negative regulator of a tyrosine kinase signaling pathway, encodes two different proteins. Genetics 137, 987-997), was co-injected at 80 ng/μl as a co-transformation marker. Progeny of injected animals were raised at the restrictive temperature for lin-15 (n765ts), and successfully transformed animals were recognized by their nonMuv phenotype.

T21C12 and T21C12ΔMlu only contain 290 base pairs upstream of the start codon. These plasmids were able to rescue the strong shrinker phenotype of unc-49, but they were incapable of complete rescue. Transformed animals could not move in a straight line. Instead, they curved dorsally, suggesting overexpression of GABA receptors on the ventral side relative to the dorsal side. Complete rescue was obtained by co-injecting two overlapping linear DNA fragments which recombined in the germline to form the complete unc-49 locus with an additional 4 kb of 5' flanking DNA. One fragment was a genomic PCR fragment containing the 4 kb 5' flanking DNA and 4 kb of the 5' end of the T21C12 insert (amplified with primers 40 and 110). The other fragment was a gel-purified Spe I-Mlu I fragment of T21C12. The overlap between these two fragments was 970 bases. Fragments were injected at roughly 10 ng/μl each, along with 40 ng/μl pEK1 and 40 ng/μl 1 kb ladder (Gibco/BRL). Transformed animals from these injections were fully-rescued. This method was employed because constructs containing the 4 kb of 5' flanking DNA were unstable and could not be maintained in bacterial hosts. This method was also used to demonstrate that fragments lacking the UNC-49A or UNC-49C open reading frames were also capable of unc-49 rescue. The UNC-49A open reading frame was eliminated by Klenow-filling the Nde I site near the UNC-49A M3 domain, and the UNC-49C open reading frame was eliminated by deleting a fragment between two Nru I sites, which included all of the UNC-49C M1 domain.

cDNA Analysis

This section is an overview of the experiments that led to the isolation of UNC-49A, UNC-49B, UNC-49C and UNC-49Cshort cDNA clones. Details of individual experimental procedures are presented in subsequent sections.

UNC-49A: The first UNC-49A cDNA clones were isolated from the cDNA library supplied by P. Okkema, probed with a mixture of labeled PCR fragments generated using primers 7 (corresponding to the conserved disulfide-bonded loop) and 8 (corresponding to repeat A, M4), and primers 5 (repeat B, M1) and 6 (repeat B, M4). Four partially-spliced UNC-49A cDNA clones were isolated. We then performed an RT-PCR experiment to isolate additional UNC-49A clones. We used first-strand cDNA prepared using polyA-selected C. elegans RNA (see 'Preparation of first strand cDNA' section). PCR was performed in two rounds. In the first round, primer 68 (conserved amino-terminal domain) was paired with primer 93 (repeat A, M4). This reaction produced a product of about 1 kb that was cloned using the TA cloning kit (Invitrogen). One µl of this reaction was re-amplified using the nested primers 73 and 94. This reaction produced an abundant 1 kb product that was likewise TA-cloned. Colonies from both ligations were analyzed by colony hybridization using the partial UNC-49A cDNA isolated above, and 96 positive colonies were picked and analyzed by double-digestion with Rsa I and Not I restriction enzymes (GIBCO/BRL). Based on unique restriction patterns, 14 clones were sequenced and five of these corresponded to fully-spliced UNC-49A mRNA. Six of the remaining clones contained unspliced introns or aberrant splice patterns that interrupted the UNC-49A open reading frame, two clones contained internal deletions, and one clone contained non-unc-49 sequences.

UNC-49B: Three UNC-49B cDNA clones were isolated from the cDNA library provided by R. Barstead. Two of these clones were identical and therefore probably not independent. Additional UNC-49B cDNA clones were isolated in two RT-PCR experiments. In the first, first-strand cDNA prepared from total *C. elegans* RNA amplified as described for UNC-49A, using primers 5 (repeat B, M1) and 6 (repeat B, M4). Seventeen clones with inserts were further analyzed by double-digesting with Rsa I and Not I restriction enzymes (GIBCO/BRL). Using these enzymes, we were able to discriminate between the three UNC-49B isoforms. This analysis showed that 7 out of 17 corresponded to UNC-49B.1; 9/17 corresponded to UNC-49B.2; and 1/17 corresponded to UNC-49B.3. In the second RT-PCR experiment, first-strand cDNA prepared using polyA-selected *C. elegans* RNA was amplified using primers 68 and 74 (repeat B, M4), SL1/74, and SL2/74 (see FIG. 2). Next, 1 µl of each reaction was re-amplified in a second round of PCR reactions using the nested primer pairs 73/6, SL1/6, and SL2/6. Each of these reactions produced plainly visible bands when analyzed by agarose gel electrophoresis, and reaction products were cloned using the TA CLONING kit (Invitrogen). Transformations were analyzed by colony hybridization (according to Ausubel, F. M., Brent, R., Kingston, R. E., Moore, D. D., Seidman, J. G., Smith, J. A., and Struhl, K. (1995). Current Protocols in Molecular Biology, K. Janssen, ed.: John Wiley and Sons, Inc.) using DURALON nylon filters (Stratagene). An UNC-49B cDNA fragment was used as a probe after it had been gel-purified away from vector sequences using the QIAQUICK Gel Extraction Kit (Qiagen), and labeled by random priming (specific activity>$1\times10^8$ cpm/µg). Positive colonies were identified using a Phosphorimager (Applied Biosystems) and 9-10 positive colonies were picked from each plate (The SL2/6 PCR reaction was performed twice, and a total of 9 positive colonies were picked from these two trials). Each clone was then subjected to double-digestion with Rsa I and Not I restriction enzymes, and clones with unique restriction patterns were identified. Clones with unique restriction patterns were sequenced. We isolated two UNC-49B.1 and one UNC-49B.2 cDNA clones.

UNC-49C: The isolation of UNC-49C and UNC-49B cDNA clones was performed simultaneously. Only details specific to the isolation of UNC-49C clones are noted here. Two independent UNC-49C cDNA clones were isolated from the library supplied by R. Barstead. RT-PCR analysis of total *C. elegans* RNA was performed using primers 1 (N-terminus of repeat C) and 4 (repeat C, M4). Fourteen clones contained inserts which represented a single size class. One of these was sequenced, and found to correspond to the UNC-49C splicing pattern. RT-PCR of polyA-selected *C. elegans* RNA was performed as described for UNC-49B using primers 75 (repeat C, M4) and 4. We sequenced two UNC-49C cDNA clones isolated in this experiment.

UNC-49Cshort: Nine UNC-49Cshort clones were isolated from the cDNA library supplied by R. Barstead. The RT-PCR analysis of polyA-selected *C. elegans* RNA described above should have detected UNC-49Cshort mRNA had it contained trans-spliced SL1 or SL2 leader sequences. We did not isolate SL-spliced UNC-49Cshort cDNA clones. However, we isolated other cDNA clones in which SL1 or SL2 sequences were spliced to internal introns. Because such splices are likely to be rare splicing errors, our protocols appear to be very sensitive. Thus the absence of SL1 or SL2 product indicates that these are not normally produced.

Summary Statistics: Twenty-seven cDNA clones were isolated from the library supplied by R. Barstead. Twenty-three of these corresponded to unc-49 sequences, and 14 were of sufficient length that they could be grouped into either the UNC-49B, UNC-49C or UNC-49Cshort class. Ninety-six clones were isolated in the RT-PCR analysis of total *C. elegans* RNA, and 175 clones were isolated in the RT-PCR analysis of polyA-selected *C. elegans* RNA. Ninety-six of these were generated by UNC-49A-specific primers, and 79 were generated by primers specific for UNC-49B and UNC-49C. Eighteen of these 79 clones were sequenced.

Polymerase Chain Reaction

Reactions were carried out using the PTC-100 or PTC-200 thermal cyclers (MJ Research). We used either Taq DNA polymerase (GIBCO/BRL) or the Expand Long Template PCR system (Boehringer). Reaction conditions matched those suggested by the enzyme manufacturers, unless otherwise noted. Details of individual PCR experiments are as follows. 1) Reactions containing primer pairs 7/8, 5/6 or 1/4 using either reverse-transcribed *C. elegans* total RNA (see 'Preparation of first-strand cDNA' section) or purified T21C12 cosmid DNA as template were cycled with the following parameters: 94° C., 30"; 55° C., 30"; 72° C., 1'30"; for 30 cycles, followed by a 7' incubation at 72° C. Taq polymerase was used for these reactions. 2) For PCR analysis of bacterial colonies, bacterial cells were transferred to 50 µl of LB broth containing 50 µg/ml ampicillin. 25 µl of this culture was diluted 1:4 with $H_2O$ and boiled in a PCR reaction tube for 5 minutes using a thermal cycler set at 100° C. 10 µl of boiled cell suspension was used for subsequent PCR reactions in a 50 µl volume using Taq polymerase and cycling parameters described for (1) above, for 25 cycles. Taq polymerase was used for these reactions as well. 3) PCR reactions on lambda phage cDNA clones was performed as follows: Phage supernatants were incubated for 5' at 100° C. PCR with Taq polymerase was then performed as described for (1) above except that an extension time of 7' was used, for 35 cycles. After 20 cycles of this program had been completed, an additional 0.5 µl of Taq polymerase was added to each reaction and the reaction was allowed to proceed for the remaining 15 cycles. 4) PCR reactions using reverse-transcribed polyA-selected RNA (see 'Preparation of first-strand cDNA' section) or purified genomic DNA for sequencing (see 'Genomic Sequencing') were performed as follows: Following an initial 94° C., 2' denaturation, samples were subjected to 10 cycles of 94° C. 10"; 55° C., 30"; 68° C., 2'; followed by 20-25 cycles of 94° C., 10"; 55° C., 30"; 68° C., 2'20" plus 20 additional seconds each cycle. The final step was a 7' incubation at 68° C. The Expand Long Template PCR System was used for these reactions, and in experiments using reverse-transcribed poly-A+ RNA as the template, the Mg2+ concentration was increased to 2.5 mM.

The sequence of all PCR primers is shown in the table below:

| Primer Name | Sequence | Sequence Identifier |
|---|---|---|
| 1 | atg tgt tca gat gcg tat tcg | SEQ ID NO: 21 |
| 5 | ctg atc gtc acc ata tct tgg | SEQ ID NO: 22 |
| 7 | tgt cca atg gac ctg aag ctg | SEQ ID NO: 23 |
| 19 | tgg agc ccg tca gta tcg gcg | SEQ ID NO: 24 |
| 37 | atc ccc agc gcc tcc ccg tta | SEQ ID NO: 25 |
| 39 | ata gtc ata aat gga ccc gcg | SEQ ID NO: 26 |
| 41 | ttc aca cat ggt gca tcg aag | SEQ ID NO: 27 |
| 45 | cga ttt tct cag tat gca cgg | SEQ ID NO: 28 |
| 47 | tat gtc gca aaa ttc gac gcc | SEQ ID NO: 29 |
| 68 | cac att aga ctt cta cat gcg | SEQ ID NO: 30 |
| 74 | cca gta gac tat att gaa gat | SEQ ID NO: 31 |
| 83 | ata cca tca tga agc aga cac | SEQ ID NO: 32 |
| 94 | gta gcc gac gtt gaa gag cac | SEQ ID NO: 33 |
| SL1 | ggt tta att acc caa gtt tga g | SEQ ID NO: 34 |
| M13F | cgc cag ggt ttt ccc agt cac gac | SEQ ID NO: 35 |
| 4 | gat gaa aac aag agg aaa gcg | SEQ ID NO: 36 |
| 6 | aag aca atg gga aac cgt atc | SEQ ID NO: 37 |
| 8 | cgg cgt att cta gaa gtg aac | SEQ ID NO: 38 |
| 20 | gta gcg acc ggc gct cag ctg | SEQ ID NO: 39 |
| 38 | ttt ttg cct gtt ttt gtc gcc | SEQ ID NO: 40 |
| 40 | ctc gga aat aat gtg cat gaa | SEQ ID NO: 41 |
| 42 | gct agt gtg ata agt gct gtg | SEQ ID NO: 42 |
| 46 | att ttc gca cca cac ctt ctc | SEQ ID NO: 43 |
| 48 | gat gaa gtg ctg gca agt gtc | SEQ ID NO: 44 |
| 73 | aaa cgt ggc aag acc ctc gac | SEQ ID NO: 45 |
| 75 | agc cag aag aga gtg ttg aac | SEQ ID NO: 46 |
| 93 | atg aag tag gcc cag tag ccg | SEQ ID NO: 47 |
| 110 | atg gtg gtt ttg ttc ccc tcc | SEQ ID NO: 48 |
| SL2 | ggt ttt aac cca gtt act caa g | SEQ ID NO: 49 |
| M13R | tca cac agg aaa cag cta tga c | SEQ ID NO: 50 |

Library Screening

Two different cDNA libraries were screened. The first, prepared using poly-A+ C. elegans RNA and the Lambda Zap vector (Stratagene), was a kind gift of Dr. R. Barstead (Barstead, R. J., and Waterston, R. H. (1989). The basal component of the nematode dense-body is vinculin. J. Biol. Chem. 264, 10177-10185). This library (350,000 plaques) was screened using DURALON nylon filters (Stratagene) according to the manufacturer's instructions using three PCR products roughly corresponding to the transmembrane domains of C-terminal repeat A, B and C as probes. These fragments were generated using primer pairs 7/8, 5/6, 1/4 respectively. Probes were labeled to greater than $1 \times 10^8$ cpm/µg by random priming and combined in equal amounts in the hybridization mixture. Inserts from positive clones were excised using the ExAssist helper phage/SOLR strain system (Stratagene).

The second library, prepared from oligo U-selected C. elegans mRNA and the lambda GT11 vector, was kindly supplied by Dr. P. Okkema (Okkema, P. G., and Fire, A. (1994). The Caenorhabditis elegans NK-2 class homeoprotein CEH-22 is involved in combinatorial activation of gene expression in pharyngeal muscle. Development 120, 2175-2186). This library (400,000 plaques) was screened as described above, except that the C-terminal repeat C probe was omitted. Inserts from positive clones were PCR amplified using primers 19 and 20 and cloned using the TA Cloning kit (Invitrogen). Growing and plating of recombinant phage, and identification of positive plaques was performed according to standard techniques as described in Ausubel, F. M., Brent, R., Kingston, R. E., Moore, D. D., Seidman, J. G., Smith, J. A., and Struhl, K. (1995). Current Protocols in Molecular Biology, K. Janssen, ed.: John Wiley and Sons, Inc.).

Preparation of First-strand cDNA

First-strand cDNA was prepared in two different ways. First, total C. elegans RNA (D. P. Morse) was reverse-transcribed using oligo-dT primers (12-18 nucleotides in length) and SUPERSCRIPT II reverse transcriptase (GIBCO/BRL), according to the protocol supplied with the enzyme. Second, C. elegans RNA (D. P. Morse) was first polyA selected, and then reverse transcribed. 30 µg of RNA was dissolved in 10 µl $H_2O$ and 20 µl TE/KCl (10 mM tris, 1 mM EDTA, 1M KCl, pH7) was added. Then, 100 µl DYNABEADS oligo(dT)$_{25}$ (Dynal) was placed in a separate tube, and liquid was removed after magnetic beads were immobilized using the MPC-1 magnet (Dynal). Beads were resuspended in 100 µl TE/KCl, liquid was removed, and the RNA solution was added. These components were then heated to 70° C. and slowly cooled to room temperature over 10 minutes using a thermal cycler. Beads were immobilized with the magnet and the supernatant was removed. Beads were then resuspended in 50 µl reverse transcriptase reaction mix. This mix contained the following: 2.5 µl 200 mM Tris-HCl, pH 8.3, 1.0M KCl; 2.5 µl 30 mM $MgCl_2$, 15 mM $MnSO_4$; 20 µl dNTP solution (2.5 mM dATP, dCTP, dGTP, dTTP; Pharmacia); 1.0 µl 40 U/µl RNAsin (Boeringer); 2.0 µl 200 U/µl SUPERSCRIPT II (GIBCO/BRL); 5.0 µl 1 U/µl RETROTHERM RT (Epicentre Technologies); 17 µl $H_2O$. Reaction was carried out at 40° C. for 30 minutes, followed by 70° C. for one hour. Beads were then immobilized with the magnet, liquid was removed, beads were washed with 100 µl TE (10 mM tris, 1 mM EDTA pH 7), liquid was removed, and beads were resuspended in 100 µl TE. One µl of suspended beads was used as template in subsequent PCR experiments.

Northern Analysis

N2 worms were grown on NGM plates containing 2% agarose (FMC) instead of agar, seeded with HB101 bacteria. Worms were harvested in M9 buffer before the plates starved out. RNA was isolated using the direct phenol extraction method, except that one chloroform extraction was used in place of the three ether extractions. PolyA+ RNA was purified from total RNA (75 µg per lane) using Oligo-dT Dynabeads (Dynal) according to manufacturer's instructions. RNA was eluted from beads directly into Northern loading buffer. Samples were run on a 1.2% formaldehyde-containing MOPS/EDTA agarose gel and transferred to Zeta-probe nylon membranes (Bio-Rad) by capillary transfer using standard techniques. Blots were probed with labeled cDNA fragments ($10^8$ cpm/µg), which specifically hybridized to the UNC-49A (Rsa I-Eco RI fragment of the 7/8 PCR fragment), UNC-49B (5/6 PCR fragment) and UNC-49C (1/4 PCR fragment) mRNAs. Blots were reprobed with an act-1 probe (M. Horner) to normalize unc-49 signals for variations in RNA loading and transfer. Band intensity was quantified using a Phosphorimager (Applied Biosystems).

Computer Sequence Analysis

Multiple sequence alignments were performed using the Pileup program in the Genetics Computer Group software package, version 9.0. Sequences used in the alignment, and their accession numbers, are listed below. Rat $GABA_A$ receptor subunits $\alpha1$ (SwissProt: p18504), $\alpha2$ (SwissProt: p23576), $\alpha3$ (SwissProt: p20236), $\alpha4$ (SwissProt: p28471), $\alpha5$ (SwissProt: p19969), $\alpha6$ (SwissProt: p30191), $\beta1$ (SwissProt: p15431), $\beta2$ (SwissProt: p15432), $\beta3$ (SwissProt: p15433), $\gamma1$ (SwissProt: p23574), $\gamma2$ (SwissProt: p18508), $\gamma3$ (SwissProt: p28473), $\delta$ (SwissProt: p18506); Rat $GABA_C$ receptor subunits $\rho1$ (SwissProt: p50572), $\rho2$ (SwissProt: p47742), $\rho3$ (SwissProt: p50573); Rat glycine receptor subunits $\alpha1$ (SwissProt: p07727), $\alpha2$ (SwissProt: p22771), $\alpha3$ (SwissProt: p24524), $\beta$ (SwissProt: p20781); Human $GABA_A$ receptor $\epsilon$ subunit (gb:U66661), *Drosophila melanogaster* rdl gene product (SwissProt: p25123), *Drosophila* GABA receptor $\beta$ subunit (SwissProt: q08832); *lymnaea stagnalis* GABA receptor $\beta$ subunit (SwissProt: p26714); and avermectin-sensitive glutamate-gated chloride channel $\alpha$ subunit (pir2:s50864), $\beta$ subunit (gb:u14525). Alignments were performed with full-length subunits. Alignments of representative GABA receptor subunits used to establish conservation shown in FIG. 4B were performed using the Clustal alignment method within the MEGALIGN program of the DNAstar sequence analysis package (DNASTAR). The rat $\alpha1$, $\beta1$, $\gamma1$, $\delta$, and $\rho1$ GABA receptor subunits, the human $\epsilon1$ GABA receptor subunit, and *drososphila* rdl protein were used for this alignment. Signal peptide cleavage sites were predicted using the PSORT program (K. Nakai, Osaka University). Consensus phosphorylation sites were identified using the ppsearch program (EMBL data library).

Genomic Southern Blot Analysis

Preparation of genomic DNA and Southern blot analysis were performed according to standard techniques using Zeta-probe nylon membranes (Bio-Rad). Blots were probed with a mixture of three labeled fragments: (1) an Eco RI fragment which includes bases 1043 to 2983 of T21C12, (2) a genomic PCR product (see 'Polymerase Chain Reaction' section in Experimental Procedures) generated using primers 7 and 8 (FIG. 2A), (3) a second Eco RI fragment which includes bases 8968 to 12054 of T21C12. Each fragment was labeled by random priming to a specific activity of $>10^8$ cpm/µg. Prehybridization, hybridization and washing (high stringency) were performed according to manufacturer's instructions. Blots were visualized by autoradiography or by using a Phosphorimager (Applied Biosystems).

DNA Sequencing

Sequencing of cDNA clones was carried out using an ABI automated DNA sequencing apparatus at the Sequencing Core Facility, University of Utah. Genomic sequencing was performed on genomic PCR fragments corresponding to UNC-49B using the THERMOSEQUENASE cycle sequencing kit (Amersham).

GFP Constructs

The S65C variant of GFP containing 3 introns (1997 Fire vector kit) was cloned into the T21C12ΔMlu construct such that GFP was inserted, in frame, into the large intracellular loop of one subunit, while the other subunits were wild-type. UNC-49A was tagged by inserting a Klenow-filled Eco RV to Xba I fragment of pPD103.87 into a T4 DNA-polymerase-treated Bsm I site. UNC-49B was tagged by inserting a Klenow-filled Cla I to Bam HI fragment of pPD102.33 into a Bsa BI site. UNC-49C was tagged by inserting a Klenow-filled Cla I to Not I fragment of pPD103.87 into a T4 DNA-polymerase-treated Bsm I site. To specifically tag the putative UNC-49Cshort subunit, the Spe I site within the common amino terminus was Klenow-filled in the UNC-49C-tagged construct. To generate transgenic lines expressing the GFP-tagged subunits, unc-49(e382);lin-15(n765ts) worms were injected with linear fragments of the GFP-tagged constructs and genomic PCR fragments containing 5' flanking DNA as described above. A slight variation was used to generate UNC-49B::GFP and UNC-49Cshort::GFP lines: Instead of co-injecting a Spe I-Mlu I unc-49 fragment with a 110/40 genomic PCR product, we co-injected an Afl II-Mlu I unc-49 fragment with a 110/38 genomic PCR fragment. This pair of fragments contained 450 base pairs of overlapping DNA. As a control, the Afl II-Mlu I fragment of the unmodified T21C12 cosmid was injected with, and without, the 5' genomic fragment: Rescue of unc-49 required the 5' genomic fragment. UNC-49B::GFPΔC was constructed by Klenow-filling a Bgl II site near UNC-49C M1, and UNC-49C::GFPΔB was constructed by Klenow-filling a Bsi WI site near UNC-49B M1. These constructs were injected into unc-49(e382);lin-15(n765ts) mutants as circular cosmids, as described for the original injections of T21C12 and T21C12ΔMlu. Fluorescence in transformed animals was strong in the ventral cord but weak or absent in the dorsal cord, suggesting that elements required for dorsal expression are contained within the 4 kb of 5' flanking DNA. We confirmed this observation by injecting the intact UNC-49B::GFP and UNC-49C::GFP constructs as circular cosmids, in the absence of the 4 kb of 5' flanking DNA. Transformants from these injections also showed much stronger GFP fluorescence in the ventral cord than in the dorsal cord.

Electrophysiology

Oocytes were removed from *Xenopus laevis* frogs anesthetized by immersion in 0.2% tricaine for 15-30 minutes. Harvested ovarian lobes were defolliculated by incubation in 2 mg/ml of collagenase (Type IA, Sigma) for 2 hours at room temperature on an orbital shaker in calcium-free ND-96 solution containing in mM: 96 NaCl, 2 KCl, 1 $MgCl_2$, and 5 HEPES (pH=7.6). The oocytes were rinsed 5-6 times with a Barth's solution that contained (in mM): 88 NaCl, 1 KCl, 0.41 $CaCl_2$, 0.33 $Ca(NO_3)_2$, 1 $MgSO_4$, 2.4 $NaHCO_3$ and 10 HEPES (pH=7.4), and selected stage V-VI oocytes were stored at 18C in Barth's solution supplemented with 1 mM Na-Pyruvate, 0.01 mg/ml gentamycin and an antibiotic-antimycotic solution containing 100 units/ml of penicillin, 100 µg/ml streptomycin and 0.25 µg/ml of Amphotericin B (Gibco BRL).

Oocytes were injected with cRNA (prepared using the mMessage mMachine kit, Ambion) into the cytoplasm 24 hours later. Glass capillary tubes (World Precision Instruments) were pulled to a fine tip on a vertical micropipette puller (David Kopf) and broken back to an outside diameter of 21 µm. RNA stocks were diluted to a final concentration of 0.75 µg/µl and injected into the oocytes (32 nl) with a microinjector (World Precision Instruments).

Electrophysiological recordings were performed 3-7 days following injection and were carried out at room temperature in a control Ringers solution containing in mM: 115 NaCl, 2.5 KCl, 1.0 BaCL$_2$, and 10 HEPES (pH=7.4). Two electrode voltage clamp recordings were obtained with a Geneclamp amplifier (Axon Instruments) using 3 mM KCl-filled microelectrodes (1-5 M). Recordings were carried out at a holding potential of −60 mV. Concentration-effect data were fit to the logistic equation:

$$I=I_{max}/\{1+(EC_{50}/[\text{agonist}])^{nH}\},$$

where $I_{max}$ is the maximal current, [agonist] is the concentration, $EC_{50}$ is the concentration of agonist resulting in half maximal activation and nH is an empirical parameter describing the steepness of fit and having the same meaning as the Hill coefficient. NFIT (Island Products) was used for non-linear curve fitting. Data are presented as the mean S.E.M.; n is the number of oocytes tested. All combinations of subunits were tested in parallel in at least two independent experiments (at least 4 oocytes for each combination of mRNAs per experiment). The effect of incorporating the UNC-49C subunit was consistent from one experiment to another. Single channel recordings were performed as described in except that 1 mM GABA was applied continuously. Single channel conductance was determined by fitting Gaussian curves to all points histograms.

EXAMPLE 2

Results

Structure of the unc-49 Locus

Figure 1:
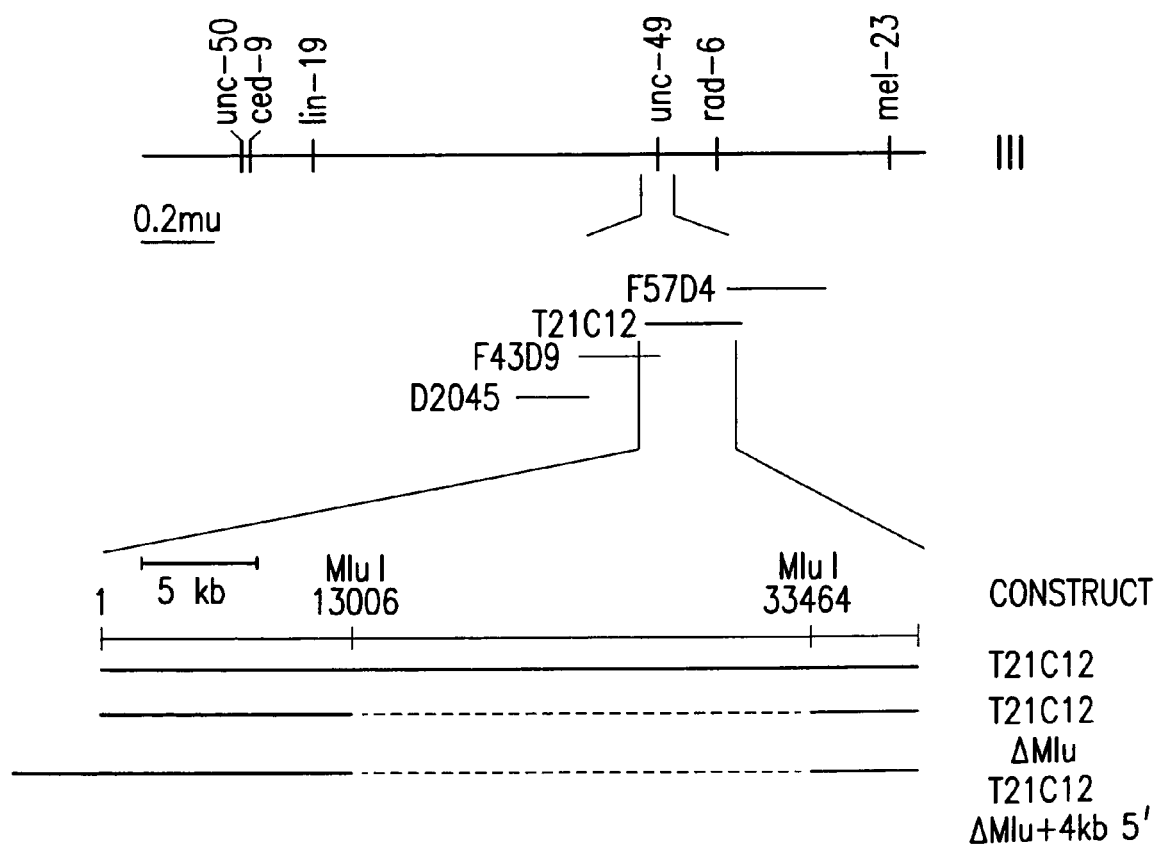
FIG. 1. Cloning and Genomic Structure of unc-49

We cloned unc-49 using standard microinjection-rescue techniques described by Mello, C. C., Kramer, J. M., Stinchcomb, D., and Ambros, V. (1991), Efficient gene transfer in C. elegans: extrachromosomal maintenance and integration of transforming sequences. EMBO J. 10, 3959-3970. Genetic map data indicated that unc-49 was located on chromosome III, between lin-19 and mel-23. One cosmid in this region, T21C12, contained a predicted 12 kb open reading frame (T21C12.1) with significant similarity to GABA$_A$ receptor subunits as described in Wilson, R. Et al. (1994). 2.2 Mb of contiguous nucleotide sequence from chromosome III of C. elegans. Nature 368, 32-38. This cosmid was injected into unc-49(e382) animals, and two stable lines were established which rescued the unc-49 shrinker phenotype. A construct containing only the T21C12.1 open reading frame (T21C12ΔMlu) also rescued the unc-49 shrinker phenotype (FIG. 1) although complete rescue required the addition of 4 kb of 5' flanking DNA (see Materials and Methods). We confirmed that the T21C12.1 open reading frame corresponded to the unc-49 gene by demonstrating that all unc-49 mutations were contained within T21C12.1 (see below).

The structure of the unc-49 locus is very different from a typical ligand-gated ion channel subunit gene. At its 5' end, unc-49 contains a single region encoding the amino terminal half of a GABA receptor subunit. The rest of the locus is made up of three repeated regions, designated A, B and C, each encoding the carboxy-terminal half of a subunit (FIG. 2A). The amino-terminal region encodes most of the extracellular residues, including two of the four loops thought to form the ligand-binding site, and the absolutely-conserved disulfide-bonded loop. The three repeats encode the other two putative ligand-binding loops, corresponding to the BDI and BDII GABA binding domains identified by Amin, J., and Weiss, D. S. (1994). Homomeric rho 1 GABA channels: activation properties and domains. Receptors and Channels 2, 227-236, and all four membrane-spanning domains.

The unc-49 Locus Encodes Three Distinct Subunits

We analyzed the structures of the mRNAs produced from unc-49 and demonstrated that unc-49 is a compound locus which produces multiple receptor subunits. Three full-length subunits, UNC-49A, UNC-49B and UNC-49C, are generated by splicing the exons encoding the amino-terminal half of a subunit to the exons encoding the carboxy-terminal repeats A, B, and C, respectively (FIG. 2B). In addition, multiple isoforms of UNC-49B and UNC-49C mRNAs were isolated. One UNC-49B isoform contains the UNC-49C exons in its 3' untranslated region. The other, UNC-49B', appears to end within the intron immediately following the UNC-49B stop codon. Alternative splicing within the UNC-49B coding region generates three additional isoforms (UNC-49B.1-3) which differ in the intracellular loop between M3 and M4 (See Materials and Methods). Two isoforms of UNC-49C were isolated. One encodes a normal, full-length subunit while the other, UNC-49Cshort, encodes an unusual subunit truncated at its amino terminus (FIG. 2B). Northern blot analysis of mRNA isolated from C. elegans hermaphrodites confirmed that each of the major classes of unc-49 mRNA is produced (FIG. 2C). Bands corresponding to the UNC-49B, UNC-49B', UNC-49C, and UNC-49Cshort mRNA species were easily-detected. UNC-49A-specific bands were also detected, although at much lower levels. In addition, a number of large RNAs were identified which may represent splicing intermediates (see asterisks). Quantitative analysis of this Northern blot revealed that UNC-49B and UNC-49C mRNA are present at roughly equal levels, while the UNC-49Cshort mRNA is two-fold less abundant, and the UNC-49A mRNA is 35-fold less abundant (see Materials and Methods).

The mRNA species encoding the UNC-49A, UNC-49B and UNC-49C subunits share considerable structural overlap. The 5' ends of the longest respective cDNA clones are within 90 nucleotides of one another. Thus, transcription of all three full-length subunits initiates at about the same place, suggesting that they are all under the control of the same promoter. Moreover, the subunits encoded by these mRNA species share a stretch of 188 identical amino terminal residues at their amino termini (FIG. 3). However, the remaining parts, which contain most of the known determinants of subunit function, are encoded by different sets of exons. UNC-49Cshort, by contrast, shares no sequence identity with UNC-49A or UNC-49B. However, UNC-49Cshort overlaps completely with the carboxy-terminal portion of repeat C, with the exception of four amino acids at the UNC-49Cshort amino terminus (FIG. 3).

Structural Features of the GABA Receptor Subunits Encoded by unc-49

The existence of three full-length subunits within the unc-49 locus led us to speculate that the UNC-49 subunits may functionally correspond to the α, β and γ subunits of vertebrate GABA$_A$ receptors. To evaluate whether the UNC-49 subunits are closely-related to the vertebrate subunits, we performed phylogenetic comparisons using a comprehensive set of ligand-gated chloride channel subunits. This analysis demonstrated that the UNC-49 subunits are not orthologous to any of the vertebrate GABA$_A$ receptor subunit classes, but more closely resemble the *Drosophila melanogaster* rdl gene product (FIG. 4A). Because the UNC-49 proteins share a common amino terminus, they are grouped into a closely-related family. To eliminate this bias from our analysis, we aligned only the carboxy-terminal segments of the ligand-gated chloride channels. The results (not shown) were largely the same as those using full-length subunits except that UNC-49C, which is very divergent, forms a unique subunit class.

Sequence comparisons showed strong conservation between the UNC-49 subunits and other ligand-gated chloride channels, however sequence differences are seen in the GABA binding domains and pore regions. Two putative GABA binding domains, BDI and BDII, have been defined by structure-function studies of the vertebrate β and ρ GABA receptor subunits. Within BDI, UNC-49A and UNC-49C contain a serine residue, and UNC-49B contains a glutamic acid residue at a position where the vertebrate β and ρ subunits and *Drosophila* rdl contain a threonine residue (marked with a # symbol in FIG. 4B). In BDII, all unc-49 subunits contain a serine residue at a position where the β, ρ and rdl subunits contain a threonine residue (marked with a $ symbol in FIG. 5B). Mutating the threonine residues in BDI or in BDII to serine in the β and ρ subunits results in significantly-decreased GABA responsiveness . These differences suggest that the unc-49-encoded receptor should be relatively insensitive to GABA, however this prediction is not fully borne out in physiological studies (see below). In the pore domain, UNC-49A and UNC-49B show a high degree of sequence conservation with the vertebrate GABA$_A$ receptor subunits but UNC-49C is highly divergent (FIG. 4B). One of the divergent residues in the UNC-49C pore domain is a glutamic acid residue (marked with @, FIG. 4B). Negatively-charged residues are generally not found in the pore domains of ligand-gated chloride channels. One exception is the β subunit of the vertebrate glycine receptor. This residue causes reduced single channel conductance in heteromeric glycine receptors containing the β subunit, and physiological studies (see below) demonstrate that UNC-49C subunits confer similarly reduced single-channel conductance. Despite its divergent sequence, UNC-49C is not expected to display altered ion selectivity because residues within M2 known to affect ion selectivity are conserved.

Finally, the intracellular loops of the UNC-49 subunits contain several potential protein kinase A, protein kinase C and casein kinase II phosphorylation sites (FIG. 4C). Surprisingly, none of the consensus phosphorylation sites within the UNC-49B intracellular loop are affected by the alternative splicing within this domain (FIG. 4C). This finding was unexpected because the number of phosphorylation sites in the vertebrate β2 and γ2 GABA$_A$ receptor subunits is regulated by alternative splicing.

All unc-49 Mutations Affect UNC-49B

Although unc-49 encodes multiple subunits, an analysis of unc-49 mutations indicated that only mutations which affect UNC-49B eliminate receptor function. First, inter se crosses determined that there is only a single complementation group within the unc-49 locus. Second, all alleles disrupt the UNC-49B subunit. The unc-49(n1324) insertion (FIG. 5A), and the point mutations in the e407 and n2392 alleles affect the common amino terminus shared by the three full-length subunits (FIG. 5B, C). By contrast, the unc-49(e929) polymorphism (FIG. 5A), and the point mutations in the e382, e468 and e641 alleles disrupt UNC-49B specifically. These three alleles each contain a missense mutation which substitutes a charged residue for the highly-conserved glycine residue found in the BDI motif of UNC-49B (FIG. 5B, C). The presence of a charged residue in the mutant subunits probably disrupts secondary structure within the ligand binding pocket because the glycine at this position is thought to be required for the formation of a hairpin turn. Third, we demonstrated that the UNC-49B open reading frame was sufficient for rescue. Specifically, rescuing fragments lacking UNC-49A or UNC-49C were capable of rescuing unc-49(e382) while a rescuing fragment lacking UNC-49B was not (not shown). Thus, loss of UNC-49B alone is sufficient to cause the shrinker phenotype.

UNC-49B and UNC-49C are Co-localized at the Neuromuscular Junction.

Because of its operon-like structure, we hypothesized that unc-49 may encode a heteromeric GABA receptor by producing multiple co-assembling GABA receptor subunits. This hypothesis predicts that the UNC-49 subunits will be co-expressed and co-localized within postsynaptic cells. We tested subunit co-localization by inserting the green fluorescent protein (GFP) into the large intracellular loop of each subunit in a plasmid encompassing the entire locus. The resulting constructs, UNC-49A::GFP, UNC-49B::GFP and UNC-49C::GFP, each produce all of the UNC-49 subunits, one of which is tagged with GFP (A, B or C, respectively; FIG. 6A). These constructs were able to rescue the shrinker phenotype of unc-49(e382) mutants. In addition, we introduced a stop codon into the common amino-terminal region of the UNC-49C::GFP construct to create an UNC-49Cshort::GFP construct (FIG. 6A). This construct did not encode any full-length UNC-49 subunits, and did not rescue the shrinker phenotype.

Using these constructs, we demonstrated that UNC-49B and UNC-49C are co-localized to the neuromuscular junction. The UNC-49A::GFP and UNC-49Cshort::GFP constructs did not produce detectable GFP fluorescence. Based on the low levels of UNC-49A mRNA detected by Northern analysis, the lack of UNC-49A::GFP expression was not surprising, but the lack of UNC-49Cshort fluorescence was unexpected. We conclude that the UNC-49Cshort mRNA is not efficiently translated in *C. elegans* hermaphrodites. By contrast, transgenic worms carrying the UNC-49B::GFP and UNC-49C::GFP constructs produced very similar patterns of GFP fluorescence (FIG. 6B, C). In both cases, fluorescence was detected mainly in the head and body wall muscles on both the dorsal and ventral sides. Within these cells, the GFP fluorescence was brightest where the nerves and muscles make contact, suggesting that both GFP-tagged subunits are efficiently localized to the neuromuscular junctions. The only consistent difference between the two expression patterns was that strong GFP fluorescence was observed in the sphincter muscle in UNC-49B::GFP animals but not in UNC-49C::GFP animals (right panel, FIG. 6B, C). We conclude that the expression patterns of UNC-49B::GFP and UNC-49C::GFP are consistent with the hypothesis that these two subunits function as a heteromeric GABA receptor.

UNC-49B and UNC-49C Physically Interact at the Neuromuscular Junction

As further evidence that UNC-49B and UNC-49C interact, we demonstrated that the localization of UNC-49C to the neuromuscular junction requires UNC-49B expression. We expressed GFP-tagged UNC-49B in the absence of UNC-49C by inactivating the UNC-49C open reading frame in the UNC-49B::GFP construct (FIG. 7A). This modified UNC-49B::GFP construct was injected into unc-49(e407)

animals, which lack all full-length unc-49 subunits because of a nonsense mutation in the common amino-terminal region. The resulting transgenic lines showed punctate fluorescence at neuromuscular junctions (FIG. 7B) which was indistinguishable from the pattern observed when UNC-49C was present. We also performed the reciprocal experiment: GFP-tagged UNC-49C was expressed in the absence of UNC-49B by inactivating the UNC-49B open reading frame in the UNC-49C::GFP construct. This construct was also injected into unc-49(e407) animals. GFP fluorescence was clearly visible on muscle membranes, but not at the neuromuscular junction (FIG. 7C, compare with FIG. 6D). Thus, synaptic localization of UNC-49C depends on the presence of UNC-49B.

UNC-49B and UNC-49C Co-assemble in Heterologous Cells

We confirmed that UNC-49B and UNC-49C co-assemble to form a heteromultimer by demonstrating that co-expression of UNC-49B and UNC-49C in heterologous cells resulted in a functionally-distinct GABA receptor. UNC-49B formed a homomeric GABA receptor in *Xenopus* oocytes. Oocytes injected with UNC-49B.1 mRNA were analyzed using the two-electrode voltage clamp technique. These cells displayed a robust, desensitizing, dose-dependent current when exposed to GABA (FIG. 8A). In a representative experiment, the GABA concentration required to produce half-maximal channel activity ($EC_{50}$) was 43.7 µM, and the Hill coefficient was 2.94, suggesting that a minimum of three GABA molecules are required to open the channel (FIG. 8B, Table 1). The reversal potential for this current was −30 mV (not shown), which is consistent with a chloride conductance. UNC-49B receptors are highly GABA selective. UNC-49B-expressing oocytes did not respond to either glutamate or glycine applied at 1 mM or 10 mM. Applications of 10 mM β-alanine produced currents that were only slightly greater than baseline noise (n=4, not shown). By contrast, UNC-49C was not able to form a homomeric GABA receptor. *Xenopus* oocytes injected with UNC-49C RNA failed to respond to GABA at any concentration, and were equally unresponsive to glutamate, glycine and β-alanine. UNC-49A, and UNC-49Cshort were also unable to form homomeric GABA receptors. When UNC-49B and UNC-49C subunits were co-expressed, a functionally distinct receptor was formed. *Xenopus* oocytes were injected with equal amounts of UNC-49B and UNC-49C RNA. The $EC_{50}$ value for GABA on these oocytes was 107.5 µM, and the Hill coefficient was 1.33 (FIG. 8B, Table 1). The GABA dose-response curves were accurately fit with a single Hill equation, which suggests that only a single population of receptors is present. This result argues UNC-49B and UNC-49C co-assemble very efficiently, such that the homomeric assembly of UNC-49B is eliminated or greatly reduced.

We confirmed that the UNC-49C subunit co-assembles efficiently with the UNC-49B subunit by co-expressing these subunits in HEK-293 fibroblast cells and performing single channel recordings. In cells expressing UNC-49B alone, we observed a single main conductance state of 37.5 pS. In cells transfected with the UNC-49B and UNC-49C, we observed a single main conductance state of 30.9 pS (FIG. 8C, Table 1). We did not observe significant numbers of channel openings corresponding to UNC-49B homomers in cells expressing both UNC-49B and UNC-49C. Although about 10% of channel openings in these cells were larger than the 30.9 pS main conductance, their conductance was roughly twice as large as the main conductance, suggesting that they corresponded to two UNC-49B/C heteromeric channels opening simultaneously. Thus in HEK-293 cells, like in *Xenopus* oocytes, UNC-49B and UNC-49C co-assemble, and the presence of UNC-49C effectively suppresses the homomeric assembly of UNC-49B, suggesting that co-assembly is efficient.

EXAMPLE 3

Discussion

We have cloned the *C. elegans* unc-49 gene and demonstrated that it is a compound locus encoding three GABA receptor subunits, UNC-49A, UNC-49B and UNC-49C, by splicing a common amino terminus to one of three alternative carboxy termini. Complex loci in *C. elegans* often produce proteins which function within the same genetic pathway. A simple hypothesis for how the UNC-49 subunits could function together is that they form a heteromeric GABA receptor.

To test this hypothesis, we first determined whether the UNC-49 subunits were co-localized. The UNC-49A and the UNC-49Cshort isoform were not expressed at significant levels in adult hermaphrodites. However, we demonstrated that UNC-49B and UNC-49C were both expressed at high levels in muscle cells, and were localized to the neuromuscular junctions. Furthermore, we demonstrated an interaction between the UNC-49B and UNC-49C subunits by showing that the synaptic localization of UNC-49C required the presence of an intact UNC-49B subunit. The simplest interpretation of this result is that UNC-49B binds to a protein required for proper receptor localization, such as a receptor tethering protein, and UNC-49C binds to UNC-49B (FIG. 9). These data provide the first direct evidence for the physical interaction of two ligand-gated ion channel subunits at an intact synapse. Previous studies have shown that ligand-gated ion channel subunits, and specifically GABA receptor subunits can be co-immunoprecipitated from brain extracts, however these results do not demonstrate that subunits are physically associated at synapses. As a final test of the hypothesis, we demonstrated that UNC-49B and UNC-49C form heteromeric GABA receptors when co-expressed in heterologous cells. Moreover, this co-assembly appeared to be very efficient because the formation of UNC-49B/C heteromers was strongly preferred over the assembly of UNC-49B homomers even though UNC-49B homomer formation occurred readily in the absence of UNC-49C. Taken together, our data make a compelling argument that UNC-49B co-assembles with UNC-49C to form a heteromeric GABA receptor at the *C. elegans* neuromuscular junction.

These results establish a novel mechanism to regulate the co-expression of subunits which assemble into heteromeric ion channels. In vertebrates, heteromers are assembled from subunits encoded by separate genes. The promoters of these genes share functional similarities, resulting in overlapping subunit expression patterns. By contrast, unc-49 achieves coordinate regulation of co-assembled subunits by driving their expression from a single promoter. Regulation may also occur at the level of mRNA splicing because the UNC-49A, UNC-49B and UNC-49C expression patterns are not identical. Thus, the unc-49 gene organization could permit the production of several different GABA receptor isoforms. A similar gene organization has been observed for other subunit genes in *C. elegans*, and the related nematode *Haemonchus contortus*. Thus nematodes in general may encode heteromeric ligand-gated ion channels using this type of compound locus. The differences in genomic organization between vertebrates and nematodes suggest that heteromultimeric receptor structure may not share a common evolutionary antecedent, but instead arose independently in the two lineages. In support of this view, the UNC-49 subunits are clearly not orthologous to the $GABA_A$ receptor subunits, which are known to form heteromeric receptors.

The addition of UNC-49C subunits to the UNC-49B GABA receptor resulted in reduced GABA sensitivity, reduced chloride conductance, and reduced cooperativity of channel gating. Examination of the UNC-49C sequence suggests a structural basis for some of its modulatory functions. Reduced GABA sensitivity may be caused by a serine residue within the BDI domain of UNC-49C. Typically, GABA receptor subunits contain a threonine residue at this position. Substitution of serine for this threonine in vertebrate β and ρ GABA receptor subunits has been shown to greatly reduce GABA sensitivity. Thus, UNC-49C is a naturally-occurring subunit variant which confirms the importance of the BDI sequence for efficient channel gating by GABA as suggested by site-directed mutagenesis experiments. Reduced chloride conductance probably results from the presence of a negatively-charged glutamic acid residue within the pore-lining M2 domain. Of the 35 ligand-gated chloride channels examined, only UNC-49C and the glycine receptor β subunit contain a negatively-charged residue within M2. This glutamic acid residue in the glycine receptor β subunit was demonstrated to cause reduced single channel conductance in glycine α/β heteromers compared to glycine α homomers. Thus, the glutamic acid residue in UNC-49C is likely to cause the reduced single channel conductance in UNC-49B/C heteromers compared to UNC-49B homomers, presumably by acting as an electrostatic impediment to the passage of negatively-charged chloride ions through the channel pore.

This study of unc-49 represents a complete vertical analysis of a neurotransmitter receptor. Analysis of a mutant lacking GABA neurotransmission led to the isolation of the unc-49 gene. Molecular characterization of unc-49 demonstrated that it encodes multiple GABA receptor subunits in an operon-like arrangement. Expression studies in vivo demonstrated that two of the subunits are co-localized to neuromuscular junctions where they co-assemble to form a heteromeric receptor. Finally, electrophysiological studies confirmed that the heteromeric receptor functions as a GABA-gated chloride channel, and demonstrated that one subunit is absolutely required for receptor function, while the other plays a modulatory role. Moreover, a specific structural basis for the function of the modulatory subunit was suggested by the sequence of its GABA-binding and pore-lining domains. The demonstration that GFP-tagged UNC-49 subunits are properly co-assembled into receptors and localized to synapses is of particular significance for future studies. Mechanisms for the assembly and localization of ligand-gated ion channels have been difficult to study in intact nervous systems. *C. elegans* offers a genetic approach to the study of these processes in the context of the functioning synapse.

The invention claimed is:

1. An isolated nematode neuromuscular junction GABA receptor complex of the formula I A-B    Formula wherein A is an amino acid sequence selected from the group consisting of:
(a) an amino acid sequence which is encoded by a nucleic acid sequence which has at least 95% identity to SEQ ID NO 2; and
(b) an amino acid sequence which has at least 95% identity to SEQ ID NO 1; and wherein B is an amino acid sequence selected from the group consisting of:
(a) an amino acid sequence which is encoded by a nucleic acid sequence which has at least 95% identity to SEQ ID NO 4; and
(b) an amino acid sequence which has at least 95% identity to SEQ ID NO 3; and wherein A-B is a heteropentamer which comprises 1 to 4 A amino acid sequences and 1 to 4 B amino acid sequences.

2. An isolated homopentamer nematode neuromuscular junction GABA receptor complex of the formula II $$B_5 \quad \text{Formula II}$$

wherein B is an amino acid sequence selected from the group consisting of:
- (a) an amino acid sequence which is encoded by a nucleic acid sequence which has at least 95% identity to SEQ ID NO 4; and
- (b) an amino acid sequence which has at least 95% identity to SEQ ID NO 3.

3. An isolated nematode neuromuscular junction GABA receptor complex subunit, comprising an amino acid sequence selected from the group consisting of:
- (a) an amino acid sequence which is encoded by a nucleic acid sequence which has at least 95% identity to SEQ ID NO 2; and
- (b) an amino acid sequence which has at least 95% identity to SEQ ID NO 1.

4. An isolated nematode neuromuscular junction GABA receptor complex subunit, comprising an amino acid sequence selected from the group consisting of:
- (a) an amino acid sequence which is encoded by a nucleic acid sequence which has at least 95% identity to SEQ ID NO 4; and
- (b) an amino acid sequence which has at least 95% identity to SEQ ID NO 3.

5. A method to determine a test substance's ability to interact with a nematode neuromuscular junction GABA receptor complex, comprising contacting a receptor complex of claim 1 with a test substance and determining whether said test substance and said receptor complex interact.

6. A method to determine a test substance's ability to interact with a nematode neuromuscular junction GABA receptor complex, comprising contacting a receptor complex of claim 2 with a test substance and determining whether said test substance and said receptor complex interact.

7. A method to determine a test substance's ability to interact with a nematode neuromuscular junction GABA receptor complex subunit, comprising contacting a receptor complex subunit of claim 3 with a test substance and determining whether said test substance and said receptor complex subunit interact.

8. A method to determine a test substance's ability to interact with a nematode neuromuscular junction GABA receptor complex subunit, comprising contacting a receptor complex subunit of claim 4 with a test substance and determining whether said test substance and said receptor complex subunit interact.

9. An isolated amino acid compound of claim 3 which comprises a nucleic acid sequence selected from the group consisting of: SEQ ID NO 1 and SEQ ID NO 3.

\* \* \* \* \*